(12) United States Patent
Rohlff et al.

(10) Patent No.: US 8,084,034 B2
(45) Date of Patent: Dec. 27, 2011

(54) PROTEINS

(75) Inventors: Christian Rohlff, Oxford (GB); Alasdair Stamps, Abingdon (GB)

(73) Assignee: Oxford BioTherapeutics Ltd., Abingdon (GB)

( * ) Notice: Subject to any disclaimer, the term of this patent is extended or adjusted under 35 U.S.C. 154(b) by 0 days.

(21) Appl. No.: 12/547,789

(22) Filed: Aug. 26, 2009

(65) Prior Publication Data

US 2010/0284908 A1 Nov. 11, 2010

Related U.S. Application Data

(63) Continuation of application No. PCT/GB2008/050126, filed on Feb. 25, 2008.

(60) Provisional application No. 60/903,462, filed on Feb. 26, 2007.

(51) Int. Cl.
*A61K 39/00* (2006.01)

(52) U.S. Cl. .................. 424/178.1; 424/181.1

(58) Field of Classification Search .......... None
See application file for complete search history.

(56) References Cited

U.S. PATENT DOCUMENTS

| | | | |
|---|---|---|---|
| 2005/0123982 A1* | 6/2005 | Zhu et al. ........... | 435/6 |
| 2005/0255114 A1 | 11/2005 | Labat et al. | |

FOREIGN PATENT DOCUMENTS

| | | |
|---|---|---|
| WO | 03042661 | 5/2003 |
| WO | 2004009622 | 1/2004 |

OTHER PUBLICATIONS

Stancovski et al (PNAS, 1991, 88:8691-8695).*
Afar, D et al, "Cancer/angiogenesis/fibrosis-related polypeptide, SEQ ID No. C301" XP002480379 retrieved from EBI—Database Accession No. ADN39931.
Afar, D et al, "Cancer/angiogenesis/fibrosis-related nucleic acid, SEQ ID No. C86" XP002480380 retrieved from EBI—Database Accession No. ADN39714.
Labat, I., et al, "Human placental protein, SEQ ID No. 1168" XP002480382 retrieved from EBI—Database Accession No. AED74340.
Labat, I., et al, "Human placental protein encoding cDNA SEQ ID No. 316" XP002480383 retrieved from EBI—Database Accession No. AED73488.
Labat, I., et al, "Large neutral amino acid transporter small unit for anti-cancer complex," XP002480381 retrieved from EBI—Database Accession No. ADJ66651.

* cited by examiner

*Primary Examiner* — Laura B Goddard
(74) *Attorney, Agent, or Firm* — Klauber & Jackson LLC

(57) ABSTRACT

The present invention provides new polypeptides. Said polypeptides are of use in the screening, diagnosis and prognosis of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer, in monitoring the effectiveness of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer treatment, and in drug development. Also provided are antibodies (and other affinity reagents such as Affibodies) which interact with or modulate the expression or activity of the polypeptides.

10 Claims, 20 Drawing Sheets

FIGURE 1

OGTA014 (SEQ ID No: 1)

Peptide Source: 1D-GE, Acute T-cell leukaemia

RRAARTLLAGPRLPGVPGPAGAQSMAGAGPKRRALAAPAAEEKEEAREKMLAAKSADGSAPAGEGEGVTLQRNIT
LLNGVAIIVGTIIGSGIFVTPTGVLKEAGSPGLALVVWAACGVFSIVGALCYAELGTTISKSGGDYAYMLEVYGS
LPAFLKLWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHRKPELE
RPIKVNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    LFFVGSR [44]
    RRALAAPAAEEK [63]
    SADGSAPAGEGEGVTLQR [65]

Tandem Peptides (underline):
    SADGSAPAGEGEGVTLQR [65]

Peptide Source: 1D-GE, B-cell non-Hodgkin's lymphoma

RRAARTLLAGPRLPGVPGPAGAQSMAGAGPKRRALAAPAAEEKEEAREKMLAAKSADGSAPAGEGEGVTLQRNIT
LLNGVAIIVGTIIGSGIFVTPTGVLKEAGSPGLALVVWAACGVFSIVGALCYAELGTTISKSGGDYAYMLEVYGS
LPAFLKLWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHRKPELE
RPIKVNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    GDVSNLDPNFSFEGTK [30]
    KPELERPIK [42]
    MAGAGPKRR [50]
    RRALAAPAAEEK [63]
    SADGSAPAGEGEGVTLQR [65]

Tandem Peptides (underline):
    GDVSNLDPNFSFEGTK [30]
    SADGSAPAGEGEGVTLQR [65]

Peptide Source: 1D-GE, Breast cancer

RRAARTLLAGPRLPGVPGPAGAQSMAGAGPKRRALAAPAAEEKEEAREKMLAAKSADGSAPAGEGEGVTLQRNIT
LLNGVAIIVGTIIGSGIFVTPTGVLKEAGSPGLALVVWAACGVFSIVGALCYAELGTTISKSGGDYAYMLEVYGS
LPAFLKLWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHRKPELE

FIGURE 1 (CONT.)

RPIKVNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    ALAAPAAEEK [8]
    DPLTIQWAR [21]
    DPLTIQWARR [22]
    GDVSNLDPNFSFEGTK [30]
    KPELERPIK [42]
    LFFVGSR [44]
    LPGVPGPAGAQSMAGAGPK [46]
    LPGVPGPAGAQSMAGAGPKRR [47]
    MAGAGPKR [49]
    MAGAGPKRR [50]
    NLMNSLGTQDQMSVSLA [52]
    SADGSAPAGEGEGVTLQR [65]
    VQDAFAAAK [81]

Tandem Peptides (underline):
    ALAAPAAEEK [8]
    SADGSAPAGEGEGVTLQR [65]

Peptide Source: 1D-GE, Colorectal cancer

RRAARTLLAGPRLPGVPGPAGAQSMAGAGPKRRALAAPAAEEKEEAREKMLAAK<u>SADGSAPAGEGEGVTLQR</u>NIT
LLNGVAIIVGTIIGSGIFVTPTGVLKEAGSPGLALVVWAACGVFSIVGALCYAELGTTISKSGGDYAYMLEVYGS
LPAFLKLWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHR**KPELE
RPIK**VNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    KPELERPIK [42]
    MAGAGPKRR [50]
    SADGSAPAGEGEGVTLQR [65]

Tandem Peptides (underline):
    SADGSAPAGEGEGVTLQR [65]

Peptide Source: 1D-GE, Hepatocellular carcinoma

RRAARTLLAGPRLPGVPGPAGAQSMAGAGPKRR<u>ALAAPAAEEK</u>EEAREKMLAAKSADGSAPAGEGEGVTLQRNIT
LLNGVAIIVGTIIGSGIFVTPTGVLKEAGSPGLALVVWAACGVFSIVGALCYAELGTTISK**SGGDYAYMLEVYGS
LPAFLK**LWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHRKPELE
RPIKVNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

FIGURE 1 (CONT.)

Mass Match Peptides (bold):
    NLMNSLGTQDQMSVSLA [52]
    RNLMNSLGTQDQMSVSLA [61]
    SADGSAPAGEGEGVTLQR [65]
    SGGDYAYMLEVYGSLPAFLK [66]

Tandem Peptides (underline):
    ALAAPAAEEK [8]
    SADGSAPAGEGEGVTLQR [65]

Peptide Source: 1D-GE, Lung cancer

RRAARTLLAGPRLPGVPGPAGAQSMAGAGPKRR<u>ALAAPAAEEK</u>EEAREKMLAAK<u>SADGSAPAGEGEGVTLQR</u>NIT
LLNGVAIIVGTIIGSGIFVTPTGVLKEAGSPGLALVVWAACGVFSIVGALCYAELGTTISKSGGDYAYMLEVYGS
LPAFLKLWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSR**LFF
VGSREGHLPSILSMIHPQLLTPVPSLVFTCVMTLLYAFSKDIFSVINFFSFFNWLCVALAIIGMIWLRHRKPELE
RPIK**VNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    ALAAPAAEEK [8]
    GDVSNLDPNFSFEGTK [30]
    KPELERPIK [42]
    LFFVGSR [44]
    MAGAGPKRR [50]
    RRALAAPAAEEK [63]
    SADGSAPAGEGEGVTLQR [65]

Tandem Peptides (underline):
    ALAAPAAEEK [8]
    SADGSAPAGEGEGVTLQR [65]

Peptide Source: 1D-GE, Lymphoid leukaemia, unspecified

RRAARTLLAGPRLPGVPGPAGAQSMAGAGPKRRALAAPAAEEKEEAREKMLAAK<u>SADGSAPAGEGEGVTLQR</u>NIT
LLNGVAIIVGTIIGSGIFVTPTGVLKEAGSPGLALVVWAACGVFSIVGALCYAELGTTISKSGGDYAYMLEVYGS
LPAFLKLWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHR**KPELE
RPIK**VNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    KPELERPIK [42]
    SADGSAPAGEGEGVTLQR [65]

Tandem Peptides (underline):
    SADGSAPAGEGEGVTLQR [65]

FIGURE 1 (CONT.)

Peptide Source: 1D-GE, Melanoma

RRAARTLLAGPRLPGVPGPAGAQSMAGAGPKRRALAAPAAEEKEEAREKMLAAKSADGSAPAGEGEGVTLQRNIT
LLNGVAIIVGTIIGSGIFVTPTGVLKEAGSPGLALVVWAACGVFSIVGALCYAELGTTISK**SGGDYAYMLEVYGS
LPAFLK**LWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHRKPELE
RPIKVNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    GDVSNLDPNFSFEGTK [30]
    SADGSAPAGEGEGVTLQR [65]
    SGGDYAYMLEVYGSLPAFLK [66]

Tandem Peptides (underline):
    SADGSAPAGEGEGVTLQR [65]

Peptide Source: 1D-GE, Osteosarcoma

RRAARTLLAGPRLPGVPGPAGAQSMAGAGPKRRALAAPAAEEKEEAREKMLAAKSADGSAPAGEGEGVTLQRNIT
LLNGVAIIVGTIIGSGIFVTPTGVLKEAGSPGLALVVWAACGVFSIVGALCYAELGTTISKSGGDYAYMLEVYGS
LPAFLKLWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHRKPELE
RPIKVNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    SADGSAPAGEGEGVTLQR [65]

Tandem Peptides (underline):
    SADGSAPAGEGEGVTLQR [65]

Peptide Source: 1D-GE, Ovarian cancer

RRAARTLLAGPRLPGVPGPAGAQSMAGAGPKRRALAAPAAEEKEEAREKMLAAKSADGSAPAGEGEGVTLQRNIT
LLNGVAIIVGTIIGSGIFVTPTGVLKEAGSPGLALVVWAACGVFSIVGALCYAELGTTISK**SGGDYAYMLEVYGS
LPAFLK**LWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHRKPELE
RPIKVNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    GDVSNLDPNFSFEGTK [30]
    SADGSAPAGEGEGVTLQR [65]
    SGGDYAYMLEVYGSLPAFLK [66]

FIGURE 1 (CONT.)

Tandem Peptides (underline):
    GDVSNLDPNFSFEGTK [30]
    SADGSAPAGEGEGVTLQR [65]

Peptide Source: 1D-GE, Pancreatic cancer

RRAARTLLAGPRLPGVPGPAGAQSMAGAGPKRRALAAPAAEEKEEAREKMLAAKSADGSAPAGEGEGVTLQRNIT
LLNGVAIIVGTIIGSGIFVTPTGVLKEAGSPGLALVVWAACGVFSIVGALCYAELGTTISKSGGDYAYMLEVYGS
LPAFLKLWIELLIIRPSSQYIVALVFATYLLKPLFPTCPVPEEAAKLVACLCVLLLTAVNCYSVKAATR**VQDAFA
AAKLLALALIILLGFVQIGK<u>GDVSNLDPNFSFEGTK**</u>LDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHR**KPELE
RPIK**VNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    ALAAPAAEEK [8]
    GDVSNLDPNFSFEGTK [30]
    KPELERPIK [42]
    MAGAGPKRR [50]
    RRALAAPAAEEK [63]
    SADGSAPAGEGEGVTLQR [65]
    VQDAFAAAK [81]

Tandem Peptides (underline):
    GDVSNLDPNFSFEGTK [30]
    SADGSAPAGEGEGVTLQR [65]

Peptide Source: 1D-GE, Renal cell cancer

RRAARTLLAGPRLPGVPGPAGAQSMAGAGPKRR<u>ALAAPAAEEK</u>EEAREKMLAAKSADGSAPAGEGEGVTLQRNIT
LLNGVAIIVGTIIGSGIFVTPTGVLKEAGSPGLALVVWAACGVFSIVGALCYAELGTTISK**SGGDYAYMLEVYGS
LPAFLK**LWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHR**KPELE
RPIK**VNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    KPELERPIK [42]
    MAGAGPKRR [50]
    SADGSAPAGEGEGVTLQR [65]
    SGGDYAYMLEVYGSLPAFLK [66]

Tandem Peptides (underline):
    ALAAPAAEEK [8]
    SADGSAPAGEGEGVTLQR [65]

Peptide Source: iTRAQ, Colorectal cancer

FIGURE 1 (CONT.)

RRAARTLLAGPRLPGVPGPAGAQSMAGAGPKRRALAAPAAEEKEEAREKMLAAKSADGSAPAGEGEGVTLQRNIT
LLNGVAIIVGTIIGSGIFVTPTGVLKEAGSPGLALVVWAACGVFSIVGALCYAELGTTISKSGGDYAYMLEVYGS
LPAFLKLWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHRKPELE
RPIKVNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    SADGSAPAGEGEGVTLQR [65]

Tandem Peptides (underline):
    SADGSAPAGEGEGVTLQR [65]

Peptide Source: iTRAQ, Non-small cell lung cancer

RRAARTLLAGPRLPGVPGPAGAQSMAGAGPKRRALAAPAAEEKEEAREKMLAAKSADGSAPAGEGEGVTLQRNIT
LLNGVAIIVGTIIGSGIFVTPTGVLKEAGSPGLALVVWAACGVFSIVGALCYAELGTTISKSGGDYAYMLEVYGS
LPAFLKLWIELLIIRPSSQYIVALVFATYLLKPLFPTCPVPEEAAKLVACLCVLLLTAVNCYSVKAATRVQDAFA
AAKLLALALIILLGFVQIGKGDVSNLDPNFSFEGTKLDVGNIVLALYSGLFAYGGWNYLNFVTEEMINPYRNLPL
AIIISLPIVTLVYVLTNLAYFTTLSTEQMLSSEAVAVDFGNYHLGVMSWIIPVFVGLSCFGSVNGSLFTSSRLFF
VGSREGHLPSILSMIHPQLLTPVPSLVFTCVMTLLYAFSKDIFSVINFFSFFNWLCVALAIIGMIWLRHRKPELE
RPIKVNLALPVFFILACLFLIAVSFWKTPVECGIGFTIILSGLPVYFFGVWWKNKPKWLLQGIWIRHTAQHQLIS
QDEGFRKTRLLLPSNKILLAATSGHSRLTQKGRKRQRQADHLSQRWSQVVQRHSSAQLWLEELACGTALSVPSRE
PTKPDTASLTSGCSSRKLSASAQWSLPPPPGHRDPLTIQWARRNLMNSLGTQDQMSVSLA

Mass Match Peptides (bold):
    MLAAKSADGSAPAGEGEGVTLQR
    [92]
    SADGSAPAGEGEGVTLQR [65]

Tandem Peptides (underline):
    MLAAKSADGSAPAGEGEGVTLQR
    [92]
    SADGSAPAGEGEGVTLQR [65]

DNA Sequence (SEQ ID No: 86)

CGGCGGGCGGCGCGCACACTGCTCGCTGGGCCGCGGCTCCCGGGTGTCCCAGGCCCGGCCGGTGCGCAGAGCATG
GCGGGTGCGGGCCCGAAGCGGCGCGCGCTAGCGGCGCCGGCGGCCGAGGAGAAGGAAGAGGCGCGGGAGAAGATG
CTGGCCGCCAAGAGCGCGGACGGCTCGGCGCCGGCAGGCGAGGGCGAGGGCGTGACCCTGCAGCGGAACATCACG
CTGCTCAACGGCGTGGCCATCATCGTGGGGACCATTATCGGCTCGGGCATCTTCGTGACGCCCACGGGCGTGCTC
AAGGAGGCAGGCTCGCCGGGGCTGGCGCTGGTGGTGTGGGCCGCGTGCGGCGTCTTCTCCATCGTGGGCGCGCTC
TGCTACGCGGAGCTCGGCACCACCATCTCCAAATCGGCGGCGACTACGCCTACATGCTGGAGGTCTACGGCTCG
CTGCCCGCCTTCCTCAAGCTCTGGATCGAGCTGCTCATCATCCGGCCTTCATCGCAGTACATCGTGGCCCTGGTC
TTCGCCACCTACCTGCTCAAGCCGCTCTTCCCCACCTGCCCGGTGCCCGAGGAGGCAGCCAAGCTCGTGGCCTGC
CTCTGCGTGCTGCTGCTCACGGCCGTGAACTGCTACAGCGTGAAGGCCGCCACCCGGGTCCAGGATGCCTTTGCC
GCCGCCAAGCTCCTGGCCCTGGCCCTGATCATCCTGCTGGGCTTCGTCCAGATCGGGAAGGGTGATGTGTCCAAT
CTAGATCCCAACTTCTCATTTGAAGGCACCAAACTGGATGTGGGGAACATTGTGCTGGCATTATACAGCGGCCTC
TTTGCCTATGGAGGATGGAATTACTTGAATTTCGTCACAGAGGAAATGATCAACCCCTACAGAAACCTGCCCCTG
GCCATCATCATCTCCCTGCCCATCGTGACGCTGGTGTACGTGCTGACCAACCTGGCCTACTTCACCACCCTGTCC
ACCGAGCAGATGCTGTCGTCCGAGGCCGTGGCCGTGGACTTCGGGAACTATCACCTGGGCGTCATGTCCTGGATC
ATCCCCGTCTTCGTGGGCCTGTCCTGCTTCGGCTCCGTCAATGGGTCCCTGTTCACATCCTCCAGGCTCTTCTTC
GTGGGGTCCCGGGAAGGCCACCTGCCCTCCATCCTCTCCATGATCCACCCACAGCTCCTCACCCCCGTGCCGTCC

FIGURE 1 (CONT.)

```
CTCGTGTTCACGTGTGTGATGACGCTGCTCTACGCCTTCTCCAAGGACATCTTCTCCGTCATCAACTTCTTCAGC
TTCTTCAACTGGCTCTGCGTGGCCCTGGCCATCATCGGCATGATCTGGCTGCGCCACAGAAAGCCTGAGCTTGAG
CGGCCCATCAAGGTGAACCTGGCCCTGCCTGTGTTCTTCATCCTGGCCTGCCTCTTCCTGATCGCCGTCTCCTTC
TGGAAGACACCCGTGGAGTGTGGCATCGGCTTCACCATCATCCTCAGCGGGCTGCCCGTCTACTTCTTCGGGGTC
TGGTGGAAAAACAAGCCCAAGTGGCTCCTCCAGGGCATCTGGATAAGACACACAGCGCAGCACCAGCTAATCTCT
CAGGACGAGGGATTCCGGAAAACCAGGCTACTGCTGCCAAGTAACAAAATCCTGCTGGCTGCCACCAGCGGACAC
AGCAGACTTACCCAGAAAGGCAGAAGAGGCAGAGGCAGGCGGATCACTTGAGCCAGAGGTGGAGCCAAGTGGTC
CAGCGTCACTCCAGTGCTCAGCTGTGGCTGGAGGAGCTGGCCTGTGGCACAGCCCTGAGTGTCCCAAGCCGGAG
CCAACGAAGCCGGACACGGCTTCACTGACCAGCGGCTGCTCAAGCCGCAAGCTCTCAGCAAGTGCCCAGTGGAGC
CTGCCGCCCCCGCCTGGGCACCGGGACCCCCTCACCATCCAGTGGGCCCGGAGAAACCTGATGAACAGTTTGGGG
ACTCAGGACCAGATGTCCGTCTCTCTTGCTTGA
```

OGTA020 (SEQ ID No: 2)

Peptide Source: 1D-GE, Colorectal cancer

MRGVWPPPVSALLSALGMSTYKRATLDEEDLVDSLSEGDAYPNGLQVNFHSPRSGQRCWAARTQVEKRLVVLVVL
LAAGLVACLAALGIQYQTRSPSVCLSEACVSVTSSILSSMDPTVDPCHDFFSYACGGWIKANPVPDGHSRWGTFS
NLWEHNQAIIKHLLENSTASVSEAERKAQVYYRACMNETRIEEL<u>RAKPLMELIER</u>LGGWNITGPWAKDNFQDTLQ
VVTAHYRTSPFFSVYVSADSKNSNSNVIQVDQSGLGLPSRDYYLNKTENEKVLTGYLNYMVQLGKLLGGGDEEAI
RPQMQQILDFETALANITIPQEKRRDEELIYHKVTAAELQTLAPAINWLPFLNTIFYPVEINESEPIVVYDKEYL
EQISTLINTTDRCLLNNYMIWNLVRKTSSFLDQRFQDADEKFMEVMYGTKKGTTNSITSSPET<u>QTPEGAER</u>IGGP
QTSGVGWSMTPPMVNAYYSPTKNEIVFPAGILQAPFYTRSSPKALNFGGIGVVVGHELTHAFDDQGREYDKDGNL
RPWWKNSSVEAFKRQTECMVEQYSNYSVNGEPVNGRHTLGENIADNGGLKAAYRAYQNWVKKNGAEHSLPTLGLT
NNQLFFLGFAQVWCSVRTPESSHEGLITDPHSPSRFRVIGSLSNSKEFSEHFRCPPGSPMNPPHKCEVW

Mass Match Peptides (bold):
    AQVYYR [10]
    EFSEHFR [24]
    RQTECMVEQYSNYSVNGEPVNGR [62]
    RRDEELIYHK [64]
    TPESSHEGLITDPHSPSR [72]
    TSSFLDQR [75]

Tandem Peptides (underline):
    AKPLMELIER [7]
    QTPEGAER [58]
    TSSFLDQR [75]

Peptide Source: 1D-GE, Hepatocellular carcinoma

MRGVWPPPVSALLSALGMSTYKRATLDEEDLVDSLSEGDAYPNGLQVNFHSPRSGQRCWAARTQVEKRLVVLVVL
LAAGLVACLAALGIQYQTRSPSVCLSEACVSVTSSILSSMDPTVDPCHDFFSYACGGWIKANPVPDGHSRWGTFS
NLWEHNQAIIKHLLENSTASVSEAERKAQVYYRACMNETRIEELRAKPLMELIERLGGWNITGPWAKDNFQDTLQ
VVTAHYRTSPFFSVYVSADSKNSNSNVIQVDQSGLGLPSRDYYLNKTENEKVLTGYLNYMVQLGKLLGGGDEEAI
RPQMQQILDFETALANITIPQEKRRDEELIYHKVTAAELQTLAPAINWLPFLNTIFYPVEINESEPIVVYDKEYL
EQISTLINTTDRCLLNNYMIWNLVRKTSSFLDQRFQDADEKFMEVMYGTKKGTTNSITSSPETQTPEGAERIGGP
QTSGVGWSMTPPMVNAYYSPTKNEIVFPAGILQAPFYTRSSPKALNFGGIGVVVGHELTHAFDDQGREYDKDGNL
RPWWKNSSVEAFKRQTECMVEQYSNYSVNGEPVNGRHTLGENIADNGGLKAAYRAYQNWVKKNGAEHSLPTLGLT
NNQLFFLGFAQVWCSVRTPESSHEGLITDPHSPSRFRVIGSLSNSKEFSEHFRCPPGSPMNPPHKCEVW

Mass Match Peptides (bold):
    AKPLMELIER [7]
    ANPVPDGHSR [9]
    AYQNWVK [12]

FIGURE 1 (CONT.)

```
CPPGSPMNPPHK [16]
DGNLRPWWK [18]
DNFQDTLQVVTAHYR [20]
EFSEHFR [24]
FMEVMYGTKK [28]
HLLENSTASVSEAERK [36]
KAQVYYR [41]
KTSSFLDQR [43]
RRDEELIYHK [64]
TPESSHEGLITDPHSPSR [72]
TSPFFSVYVSADSK [74]
TSSFLDQR [75]
```

Tandem Peptides (underline):
```
AKPLMELIER [7]
DGNLRPWWK [18]
EFSEHFR [24]
TSSFLDQR [75]
```

Peptide Source: 1D-GE, Lung cancer

MRGVWPPPVSALLSALGMSTYKRATLDEEDLVDSLSEGDAYPNGLQVNFHSPRSGQRCWAARTQVEKRLVVLVVL
LAAGLVACLAALGIQYQTRSPSVCLSEACVSVTSSILSSMDPTVDPCHDFFSYACGGWIKANPVPDGHSRWGTFS
NLWEHNQAIIKHLLENSTASVSEAERKAQVYYRACMNETRIEELRAKPLMELIERLGGWNITGPWAKDNFQDTLQ
VVTAHYRTSPFFSVYVSADSKNSNSNVIQVDQSGLGLPSRDYYLNKTENEKVLTGYLNYMVQLGKLLGGGDEEAI
RPQMQQILDFETALANITIPQEKRRDEELIYHKVTAAELQTLAPAINWLPFLNTIFYPVEINESEPIVVYDKEYL
EQISTLINTTDRCLLNNYMIWNLVRKTSSFLDQRFQDADEKFMEVMYGTKKGTTNSITSSPETQTPEGAERIGGP
QTSGVGWSMTPPMVNAYYSPTKNEIVFPAGILQAPFYTRSSPKALNFGGIGVVVGHELTHAFDDQGREYDKDGNL
RPWWKNSSVEAFKRQTECMVEQYSNYSVNGEPVNGRHTLGENIADNGGLKAAYRAYQNWVKKNGAEHSLPTLGLT
NNQLFFLGFAQVWCSVRTPESSHEGLITDPHSPSRFRVIGSLSNSKEFSEHFRCPPGSPMNPPHKCEVW

Mass Match Peptides (bold):
```
AQVYYR [10]
CLLNNYMIWNLVRK [15]
DNFQDTLQVVTAHYR [20]
EFSEHFR [24]
NEIVFPAGILQAPFYTR [51]
NSSVEAFK [54]
QTECMVEQYSNYSVNGEPVNGR [57]
RQTECMVEQYSNYSVNGEPVNGR [62]
RRDEELIYHK [64]
TPESSHEGLITDPHSPSR [72]
TQVEKR [73]
```

Tandem Peptides (underline):
```
AKPLMELIER [7]
EFSEHFR [24]
```

Peptide Source: 1D-GE, Melanoma

MRGVWPPPVSALLSALGMSTYKRATLDEEDLVDSLSEGDAYPNGLQVNFHSPRSGQRCWAARTQVEKRLVVLVVL
LAAGLVACLAALGIQYQTRSPSVCLSEACVSVTSSILSSMDPTVDPCHDFFSYACGGWIKANPVPDGHSRWGTFS
NLWEHNQAIIKHLLENSTASVSEAERKAQVYYRACMNETRIEELRAKPLMELIERLGGWNITGPWAKDNFQDTLQ
VVTAHYRTSPFFSVYVSADSKNSNSNVIQVDQSGLGLPSRDYYLNKTENEKVLTGYLNYMVQLGKLLGGGDEEAI
RPQMQQILDFETALANITIPQEKRRDEELIYHKVTAAELQTLAPAINWLPFLNTIFYPVEINESEPIVVYDKEYL

FIGURE 1 (CONT.)

EQISTLINTTDRCLLNNYMIWNLVRKTSSFLDQRFQDADEKFMEVMYGTKKGTTNSITSSPETQTPEGAERIGGP
QTSGVGWSMTPPMVNAYYSPTKNEIVFPAGILQAPFYTRSSPKALNFGGIGVVVGHELTHAFDDQGREYDKDGNL
RPWWKNSSVEAFKRQTECMVEQYSNYSVNGEPVNGRHTLGENIADNGGLKAAYRAYQNWVKKNGAEHSLPTLGLT
NNQLFFLGFAQVWCSVRTPESSHEGLITDPHSPSRFRVIGSLSNSK<u>EFSEHFR</u>CPPGSPMNPPHKCEVW

Mass Match Peptides (bold):
DGNLRPWWK [18]
DNFQDTLQVVTAHYR [20]
EFSEHFR [24]
NEIVFPAGILQAPFYTR [51]
RRDEELIYHK [64]

Tandem Peptides (underline):
EFSEHFR [24]

Peptide Source: 1D-GE, Pancreatic cancer

MRGVWPPPVSALLSALGMSTYKRATLDEEDLVDSLSEGDAYPNGLQVNFHSPRSGQRCWAARTQVEKRLVVLVVL
LAAGLVACLAALGIQYQTRSPSVCLSEACVSVTSSILSSMDPTVDPCHDFFSYACGGWIKANPVPDGHSRWGTFS
NLWEHNQAIIKHLLENSTASVSEAERKAQVYYRACMNETRIEELRAKPLMELIERLGGWNITGPWAKDNFQDTLQ
VVTAHYRTSPFFSVYVSADSKNSNSNVIQVDQSGLGLPSRDYYLNKTENEKVLTGYLNYMVQLGKLLGGGDEEAI
RPQMQQILDFETALANITIPQEKRRDEELIYHKVTAAELQTLAPAINWLPFLNTIFYPVEINESEPIVVYDKEYL
EQISTLINTTDRCLLNNYMIWNLVRKTSSFLDQRFQDADEKFMEVMYGTKKGTTNSITSSPETQTPEGAERIGGP
QTSGVGWSMTPPMVNAYYSPTKNEIVFPAGILQAPFYTRSSPKALNFGGIGVVVGHELTHAFDDQGREYDKDGNL
RPWWKNSSVEAFKRQTECMVEQYSNYSVNGEPVNGRHTLGENIADNGGLKAAYRAYQNWVKKNGAEHSLPTLGLT
NNQLFFLGFAQVWCSVRTPESSHEGLITDPHSPSRFRVIGSLSNSK<u>EFSEHFRCPPGSPMNPPHK</u>CEVW

Mass Match Peptides (bold):
AKPLMELIER [7]
ANPVPDGHSR [9]
AQVYYR [10]
AYQNWVK [12]
CLLNNYMIWNLVR [14]
CLLNNYMIWNLVRK [15]
CPPGSPMNPPHK [16]
DGNLRPWWK [18]
DNFQDTLQVVTAHYR [20]
EFSEHFR [24]
FMEVMYGTKK [28]
GVWPPPVSALLSALGMSTYKR [33]
HLLENSTASVSEAER [35]
HLLENSTASVSEAERK [36]
HTLGENIADNGGLK [37]
KTSSFLDQR [43]
NEIVFPAGILQAPFYTR [51]
NSNSNVIQVDQSGLGLPSR [53]
NSSVEAFKR [55]
RDEELIYHK [59]
RQTECMVEQYSNYSVNGEPVNGR [62]
RRDEELIYHK [64]
TPESSHEGLITDPHSPSR [72]
TSPFFSVYVSADSK [74]
TSSFLDQR [75]
WGTFSNLWEHNQAIIK [83]

Tandem Peptides (underline):
AKPLMELIER [7]

FIGURE 1 (CONT.)

```
EFSEHFR [24]
HTLGENIADNGGLK [37]
```

Peptide Source: 1D-GE, Renal cell cancer

MRGVWPPPVSALLSALGMSTYKRATLDEEDLVDSLSEGDAYPNGLQVNFHSPRSGQRCWAARTQVEKRLVVLVVL
LAAGLVACLAALGIQYQTRSPSVCLSEACVSVTSSILSSMDPTVDPCHDFFSYACGGWIKANPVPDGHSRWGTFS
NLWEHNQAIIKHLLENSTASVSEAERKAQVYYRACMNETRIEELR<u>AKPLMELIER</u>LGGWNITGPWAK**DNFQDTLQ
VVTAHYRTSPFFSVYVSADSKNSNSNVIQVDQSGLGLPSRDYYLNKTENEKVLTGYLNYMVQLGK**LLGGGDEEAI
RPQMQQILDFETALANITIPQEKRRDEELIYHKVTAAELQTLAPAINWLPFLNTIFYPVEINESEPIVVYDKEYL
EQISTLINTTDRCLLNNYMIWNLVRK<u>TSSFLDQR</u>FQDADEKFMEVMYGTKKGTTNSITSSPETQTPEGAERIGGP
QTSGVGWSMTPPMVNAYYSPTKNEIVFPAGILQAPFYTRSSPKALNFGGIGVVVGHELTHAFDDQGREYDKDGNL
RPWWKNSSVEAFKRQTECMVEQYSNYSVNGEPVNGRHTLGENIADNGGLKAAYRAYQNWVKKNGAEHSLPTLGLT
NNQLFFLGFAQVWCSVRTPESSHEGLITDPHSPSRFRVIGSLSNSKEFSEHFRCPPGSPMNPPHKCEVW

Mass Match Peptides (bold):
        AKPLMELIER [7]
        ANPVPDGHSR [9]
        AYQNWVKK [13]
        CLLNNYMIWNLVR [14]
        DNFQDTLQVVTAHYR [20]
        EFSEHFR [24]
        FMEVMYGTKK [28]
        FQDADEK [29]
        HLLENSTASVSEAER [35]
        NEIVFPAGILQAPFYTR [51]
        NSNSNVIQVDQSGLGLPSR [53]
        TPESSHEGLITDPHSPSR [72]
        TQVEKR [73]
        TSSFLDQR [75]
        VLTGYLNYMVQLGK [80]

Tandem Peptides (underline):
        AKPLMELIER [7]
        TSSFLDQR [75]

Peptide Source: iTRAQ, Renal cell cancer

MRGVWPPPVSALLSALGMSTYKRATLDEEDLVDSLSEGDAYPNGLQVNFHSPRSGQRCWAARTQVEKRLVVLVVL
LAAGLVACLAALGIQYQTRSPSVCLSEACVSVTSSILSSMDPTVDPCHDFFSYACGGWIKANPVPDGHSRWGTFS
NLWEHNQAIIKHLLENSTASVSEAERKAQVYYRACMNETRIEELRAKPLMELIERLGGWNITGPWAKDNFQDTLQ
VVTAHYRTSPFFSVYVSADSKNSNSNVIQVDQSGLGLPSRDYYLNKTENEKVLTGYLNYMVQLGKLLGGGDEEAI
RPQMQQILDFETALANITIPQEKR<u>RDEELIYHK</u>VTAAELQTLAPAINWLPFLNTIFYPVEINESEPIVVYDKEYL
EQISTLINTTDRCLLNNYMIWNLVRKTSSFLDQRFQDADEKFMEVMYGTKKGTTNSITSSPETQTPEGAERIGGP
QTSGVGWSMTPPMVNAYYSPTKNEIVFPAGILQAPFYTRSSPKALNFGGIGVVVGHELTHAFDDQGREYDKDGNL
RPWWKNSSVEAFKRQTECMVEQYSNYSVNGEPVNGRHTLGENIADNGGLKAAYRAYQNWVKKNGAEHSLPTLGLT
NNQLFFLGFAQVWCSVRTPESSHEGLITDPHSPSRFRVIGSLSNSKEFSEHFRCPPGSPMNPPHKCEVW

Mass Match Peptides (bold):
        RDEELIYHK [95]

Tandem Peptides (underline):
        RDEELIYHK [95]

FIGURE 1 (CONT.)

DNA Sequence (SEQ ID No: 87)

ATGCGGGGCGTGTGGCCGCCCCCGGTGTCCGCCCTGCTGTCGGCGCTGGGGATGTCGACGTACAAGCGGGCCACG
CTGGACGAGGAGGACCTGGTGGACTCGCTCTCCGAGGGCGACGCATACCCCAACGGCCTGCAGGTGAACTTCCAC
AGCCCCCGGAGTGGCCAGAGGTGCTGGGCTGCACGGACCCAGGTGGAGAAGCGGCTGGTGGTGTTGGTGGTACTT
CTGGCGGCAGGACTGGTGGCCTGCTTGGCAGCACTGGGCATCCAGTACCAGACAAGATCCCCCTCTGTGTGCCTG
AGCGAAGCTTGTGTCTCAGTGACCAGCTCCATCTTGAGCTCCATGGACCCCACAGTGGACCCCTGCCATGACTTC
TTCAGCTACGCCTGTGGGGGCTGGATCAAGGCCAACCCAGTCCCTGATGGCCACTCACGCTGGGGGACCTTCAGC
AACCTCTGGGAACACAACCAAGCAATCATCAAGCACCTCCTCGAAAACTCCACGGCCAGCGTGAGCGAGGCAGAG
AGAAAGGCGCAAGTATACTACCGTGCGTGCATGAACGAGACCAGGATCGAGGAGCTCAGGGCCAAACCTCTAATG
GAGTTGATTGAGAGGCTCGGGGGCTGGAACATCACAGGTCCCTGGGCCAAGGACAACTTCCAGGACACCCTGCAG
GTGGTCACCGCCCACTACCGCACCTCACCCTTCTTCTCTGTCTATGTCAGTGCCGATTCCAAGAACTCCAACAGC
AACGTGATCCAGGTGGACCAGTCTGGCCTGGGCTTGCCCTCGAGAGACTATTACCTGAACAAAACTGAAAACGAG
AAGGTGCTGACCGGATATCTGAACTACATGGTCCAGCTGGGGAAGCTGCTGGGCGGCGGGACGAGGAGGCCATC
CGGCCCCAGATGCAGCAGATCTTGGACTTTGAGACGGCACTGGCCAACATCACCATCCCACAGGAGAAGCGCCGT
GATGAGGAGCTCATCTACCACAAAGTGACGGCAGCCGAGCTGCAGACCTTGGCACCCGCCATCAACTGGTTGCCT
TTTCTCAACACCATCTTCTACCCCGTGGAGATCAATGAATCCGAGCCTATTGTGGTCTATGACAAGGAATACCTT
GAGCAGATCTCCACTCTCATCAACACCACCGACAGATGCCTGCTCAACAACTACATGATCTGGAACCTGGTGCGG
AAAACAAGCTCCTTCCTTGACCAGCGCTTTCAGGACGCCGATGAGAAGTTCATGGAAGTCATGTACGGGACCAAG
AAGGGGACCACCAATAGTATTACTTCTTCCCCGGAAACACAGACCCCAGAAGGTGCAGAGAGAATTGGTGGCCCT
CAGACATCAGGGGTGGGGTGGAGCATGACCCCGCCCATGGTGAACGCCTACTACTCGCCCACCAAGAATGAGATT
GTGTTTCCGGCCGGGATCCTGCAGGCACCATTCTACACACGCTCCTCACCCAAGGCCTTAAACTTTGGTGGCATA
GGTGTCGTCGTGGGCCATGAGCTGACTCATGCTTTTGATGATCAAGGACGGGAGTATGACAAGGACGGGAACCTC
CGGCCATGGTGGAAGAACTCATCCGTGGAGGCCTTCAAGCGTCAGACCGAGTGCATGGTAGAGCAGTACAGCAAC
TACAGCGTGAACGGGGAGCCGGTGAACGGGCGGCACACCCTGGGGGAGAACATCGCCGACAACGGGGGTCTCAAG
GCGGCCTATCGGGCTTACCAGAACTGGGTGAAGAAGAACGGGGCTGAGCACTCGCTCCCCACCCTGGGCCTCACC
AATAACCAGCTCTTCTTCCTGGGCTTTGCACAGGTCTGGTGCTCCGTCCGCACACCTGAGAGCTCCCACGAAGGC
CTCATCACCGATCCCCACAGCCCCTCTCGCTTCCGGGTCATCGGCTCCCTCTCCAATTCCAAGGAGTTCTCAGAA
CACTTCCGCTGCCCACCTGGCTCACCCATGAACCCGCCTCACAAGTGCGAAGTCTGGTAAGGACGAAGCGGAGAG
AGCCAAGACGGAGGAGGGGAAGGGGCTGAGGACGAGACCCCATCCAGCCTCCAGGGCATTGCTCAGCCCGCCTTG
GCCACCCGGGGCCCTGCTTCCTCACACTGGCGGGTTTTCAGCCGGAACCGAGCCCATGGTGTTGGCTCTCAACGT
GACCCGCAGTCTGATCCCCTGTGAAGAGCCGGACATCCCAGGCACACGTGTGCGCCACCTTCAGCAGGCATTCGG
GTGCTGGGCTGGTGGCTCATCAGGCCTGGGCCCCACACTGACAAGCGCCAGATACGCCACAAATACCACTGTGTC
AAATGCTTTCAAGATATATTTTTGGGGAAACTATTTTTTAAACACTGTGGAATACACT

OGTA067 (SEQ ID No: 3)

Peptide Source: 1D-GE, Colorectal cancer

VQISEDSPISFLVVKVSATDVDTGVNGEISYSLFQASDEISKTFKVDFLTGEIRLKKQLDFEKFQSYEVNIEARD
AGGFSGKCTVLIQVIDVNDHAPEVTMSAFTSPIPENAPETVVALFSVSDLDSGENGKISCSIQEDLPFLLKSSVG
NFYTLLTETPLDRESRAEYNVTITVTDLGTPRLTTHLNMTVLVSDVNDNAPAFTQTSYTLFVRENNSPALHIGSV
SATDRDSGTNAQVTYSLLPPQDPHLPLASLVSINTDNGHLFALRSLDYEALQAFEFRVGASDRGSPALSSEALVR
VLVLDANDNSPFVLYPLQNGSAPCTELVPRAAEPGYLVTKVVAVDGDSGQNAWLSYQLLKATEPGLFGVWAHNGE
VRTARLLSERDAAKQRLVVLVKDNGEPPCSATATLHLLLVDGFSQPYLPLPEAAPAQGQADSLTVYLVVALASVS
SLFLFSVLLFVAVLLCRRSRAASVGRCSVPEGPFPGHLVDVRGTGSLSQNYHLSGAGAELGSYSVVEETERGSFV
ANLGKDLGLGLTEMSTRKARIISQGNKQHLQLKAQTGDLLINEKLDREELCGPTEPCILHFQVLMENPLEIFQAE
LRVIDINDHSPMFTEKEMILKIPENSPLGTEFPLNHALDLDVGSNNVQNYKISPSSHFRVLIHEFRDGRKYPELV
LDKELDREEEPQLRLTLTALDGGSPPRSGTAQVRIEVVDINDNAPEFEQPIYKVQIPENSPLGSLVATVSARDLD
GGANGKISYTLFQPSEDISKTLEVNPMTGGTPRLKTEHNITVQISDVNDNAPTFTQTSYTLFVRENNSPALHIGS
VSATDRDSGTNAQVTYSLLPPQDPHLPLASLVSINADNGHLFALRSLDYEALREFEFRVSATDRGSPALSSEALV
RVLVLDANDNSPFVLYPLQNGSAPCTELVPRAAEPGYLVTKVVAVDGDSGQNAWLSYQLLKATEPGLFGVWAHNG
EVRTARLLSERDAAKQRLVVLVKDNGEPPRSATATLHVLLVDGFSQPFLPLPEAAPGQTQANSLTVYLVVAISLC
LICISCLLYVKLSFFLDIRPLNKIL

Mass Match Peptides:
Tandem Peptides:

FIGURE 1 (CONT.)

CSVPEGPFPGHLVDVR [17]

Peptide Source: 1D-GE, Ovarian cancer

VQISEDSPISFLVVKVSATDVDTGVNGEISYSLFQASDEISKTFKVDFLTGEIRLKKQLDFEKFQSYEVNIEARD
AGGFSGKCTVLIQVIDVNDHAPEVTMSAFTSPIPENAPETVVALFSVSDLDSGENGKISCSIQEDLPFLLKSSVG
NFYTLLTETPLDRESRAEYNVTITVTDLGTPRLTTHLNMTVLVSDVNDNAPAFTQTSYTLFVRENNSPALHIGSV
SATDRDSGTNAQVTYSLLPPQDPHLPLASLVSINTDNGHLFALRSLDYEALQAFEFRVGASDRGSPALSSEALVR
VLVLDANDNSPFVLYPLQNGSAPCTELVPRAAEPGYLVTKVVAVDGDSGQNAWLSYQLLK**ATEPGLFGVWAHNGE
VR**TARLLSERDAAKQRLVVLVKDNGEPPCSATATLHLLLVDGFSQPYLPLPEAAPAQGQADSLTVYLVVALASVS
SLFLFSVLLFVAVLLCRRSRAASVGRCSVPEGPFPGHLVDVRGTGSLSQNYHLSGAGAELGSYSVVEETERGSFV
ANLGKDLGLGLTEMSTRKARIISQGNKQHLQLKAQTGDLLINEKLDREELCGPTEPCILHFQVLMENPLEIFQAE
LRVIDINDHSPMFTEKEMILKIPENSPLGTEFPLNHALDLDVGSNNVQNYKISPSSHFRVLIHEFRDGRKYPELV
LDKELDREEEPQLRLTLTALDGGSPPRSGTAQVRIEVVDINDNAPEFEQPIYKVQIPENSPLGSLVATVSARDLD
GGANGKISYTLFQPSEDISKTLEVNPMTGGTPRLKTEHNITVQISDVNDNAPTFTQTSYTLFVRENNSPALHIGS
VSATDRDSGTNAQVTYSLLPPQDPHLPLASLVSINADNGHLFALRSLDYEALREFEFRVSATDRGSPALSSEALV
RVLVLDANDNSPFVLYPLQNGSAPCTELVPRAAEPGYLVTKVVAVDGDSGQNAWLSYQLLK**ATEPGLFGVWAHNG
EVR**TARLLSERDAAKQRLVVLVKDNGEPPRSATATLHVLLVDGFSQPFLPLPEAAPGQTQANSLTVYLVVA<u>ISLC
LICISCLLYVK</u>LSFFLDIRPLNKIL

Mass Match Peptides:
    ATEPGLFGVWAHNGEVR [11]
    DLGLGLTEMSTR [19]
    SGTAQVR [67]
Tandem Peptides:
    ISLCLICISCLLYVK [40]

Peptide Source: iTRAQ, Renal cell cancer

VQISEDSPISFLVVKVSATDVDTGVNGEISYSLFQASDEISKTFKVDFLTGEIRLKKQLDFEKFQSYEVNIEARD
AGGFSGKCTVLIQVIDVNDHAPEVTMSAFTSPIPENAPETVVALFSVSDLDSGENGKISCSIQEDLPFLLKSSVG
NFYTLLTETPLDRESRAEYNVTITVTDLGTPRLTTHLNMTVLVSDVNDNAPAFTQTSYTLFVRENNSPALHIGSV
SATDRDSGTNAQVTYSLLPPQDPHLPLASLVSINTDNGHLFALRSLDYEALQAFEFRVGASDRGSPALSSEALVR
VLVLDANDNSPFVLYPLQNGSAPCTELVPRAAEPGYLVTKVVAVDGDSGQNAWLSYQLLKATEPGLFGVWAHNGE
VRTARLLSERDAAKQRLVVLVKDNGEPPCSATATLHLLLVDGFSQPYLPLPEAAPAQGQADSLTVYLVVALASVS
SLFLFSVLLFVAVLLCRRSRAASVGRCSVPEGPFPGHLVDVRGTGSLSQNYHLSGAGAELGSYSVVEETERGSFV
ANLGKDLGLGLTEMSTRKARIISQGNKQHLQLKAQTGDLLINEKLDREELCGPTEPCILHFQVLMENPLEIFQAE
LRVIDINDHSPMFTEKEMILKIPENSPLGTEFPLNHALDLDVGSNNVQNYKISPSSHFRVLIHEFRDGRKYPELV
LDKELDREEEPQLRLTLTALDGGSPPRSGTAQVRIEVVDINDNAPEFEQPIYKVQIPENSPLGSLVATVSARDLD
GGANGKISYTLFQPSEDISKTLEVNPMTGGTPRLKTEHNITVQISDVNDNAPTFTQTSYTLFVRENNSPALHIGS
VSATDRDSGTNAQVTYSLLPPQDPHLPLASLVSINADNGHLFALRSLDYEALREFEFRVSATDRGSPALSSEALV
RVLVLDANDNSPFVLYPLQNGSAPCTELVPRAAEPGYLVTKVVAVDGDSGQNAWLSYQLLKATEPGLFGVWAHNG
EVRTARLLSERDAAKQRLVVLVKDNGEPPRSATATLHVLLVDGFSQPFLPLPEAAPGQTQANSLTVYLVVAISLC
LICISCLLYVKLSFFLDIRPLNKIL

Mass Match Peptides:
    LVVLVK [93]
Tandem Peptides:
    LVVLVK [93]

DNA Sequence (SEQ ID No: 88)

FIGURE 1 (CONT.)

```
GGTGCAGATCTCTGAGGACAGTCCAATAAGCTTCCTGGTTGTGAAGGTCTCTGCCACGGATGTAGACACAGGAGT
CAACGGAGAGATTTCCTATTCACTTTTCCAAGCTTCAGATGAGATAAGCAAAACTTTTAAGGTCGATTTCTTGAC
AGGAGAAATTCGACTAAAGAAACAACTTGATTTCGAAAAATTTCAGTCCTATGAAGTCAATATCGAGGCGAGAGA
TGCTGGAGGCTTTTCTGGAAAATGCACCGTTCTGATTCAAGTGATAGATGTGAACGACCATGCCCCAGAAGTTAC
CATGTCTGCATTTACCAGCCCAATACCTGAGAATGCGCCTGAAACTGTGGTTGCACTTTTCAGTGTTTCAGACCT
TGATTCAGGAGAAAATGGGAAAATAAGTTGCTCCATTCAGGAGGATCTACCCTTCCTCCTGAAATCTTCTGTGGG
GAACTTTTACACCCTACTAACAGAGACACCACTAGCAGAGAAAGCAGAGCCGAGTACAACGTCACTATCACCGT
CACTGACTTAGGGACACCCAGGCTGACAACACATCTCAATATGACCGTGCTGGTGTCGGACGTCAATGACAACGC
CCCCGCCTTCACCCAAACCTCCTACACCCTGTTCGTCCGCGAGAACAACAGCCCCGCCCTGCACATCGGCAGCGT
CAGCGCCACAGACAGAGACTCGGGCACCAACGCCCAGGTCACCTACTCGCTGCTGCCGCCCCAGGATCCGCACCT
GCCCCTCGCCTCCCTGGTCTCCATCAACACAGACAACGGCCACCTGTTCGCCCTCAGGTCGCTGGACTACGAGGC
CCTGCAGGCGTTCGAGTTCCGGGTGGGCGCTTCAGACCGCGGCTCCCCGGCTTTGAGCAGCGAGGCGCTGGTGCG
CGTGCTGGTGCTGGACGCCAACGACAACTCGCCCTTCGTGCTGTACCCGCTGCAGAATGGCTCCGCGCCCTGCAC
CGAGCTGGTGCCCCGGGCGGCCGAGCCGGGCTACCTGGTGACCAAGGTGGTGGCGGTGGACGGCGACTCGGGCCA
GAACGCCTGGCTGTCGTACCAGCTGCTCAAGGCCACGGAGCCCGGGCTGTTCGGTGTGTGGGCGCACAATGGCGA
GGTGCGCACCGCCAGGCTGCTGAGCGAGCGCGACGCGGCCAAGCAGAGGCTGGTGGTGCTGGTCAAGGACAATGG
CGAGCCTCCGTGCTCGGCCACCGCCACGCTGCACTTGCTCCTGGTGGACGGCTTCTCCCAGCCCTACCTGCCGCT
TCCGGAGGCTGCCCCAGCCCAGGGCCAGGCCGACTCTCTCACCGTCTACCTGGTGGTGGCGTTGGCCTCGGTGTC
TTCGCTCTTCCTCTTCTCGGTGCTCCTGTTCGTGGCGGTGCTGCTGTGTAGGAGGAGCAGGGCGGCCTCGGTGGG
TCGCTGCTCAGTGCCTGAGGGCCCCTTTCCAGGGCATCTGGTGGACGTGAGGGGCACCGGGAGCCTGTCTCAGAA
CTATCACTTGTCTGGGGCGGGCGCCGAGTTGGGGTCCTATTCCGTAGTGGAAGAAACGGAGAGAGGCTCTTTTGT
GGCAAATCTAGGAAAAGACCTGGGGTTGGGGTTGACAGAGATGTCCACCCGCAAGGCCAGGATCATTTCCCAGGG
GAACAAACAGCATTTGCAGCTCAAGGCTCAAACTGGGGATTTGCTCATAAATGAGAAGCTAGATCGAGAGGAGCT
ATGCGGTCCCACTGAGCCTTGCATACTACATTTCCAAGTGTTAATGGAAAACCCTTTAGAAATATTTCAGGCTGA
ACTGAGGGTGATAGATATAAATGACCATTCTCCCATGTTCACTGAAAAGGAAATGATTCTAAAAATACCGGAAAA
CAGTCCTCTAGGAACTGAGTTCCCTCTGAATCATGCTTTGGACTTGGACGTAGGAAGCAATAATGTTCAAAACTA
TAAAATCAGCCCAAGCTCTCATTTCCGGGTTCTAATCCATGAATTCAGAGATGGCAGGAAATACCCTGAGCTAGT
GTTGGATAAAGAGCTGGATCGGGAGGAGGAGCCTCAACTAAGATTAACCCTGACAGCGCTGGATGGTGGCTCTCC
ACCGCGATCTGGAACTGCTCAGGTCCGTATTGAAGTGGTGGACATCAATGATAACGCTCCTGAGTTTGAGCAGCC
CATCTACAAAGTGCAGATTCCAGAGAACAGTCCTCTTGGCTCCCTGGTTGCCACCGTCTCCGCCAGGGATTTAGA
CGGCGGAGCCAATGGAAAAATATCATACACACTCTTTCAGCCTTCGGAGGATATTAGTAAAACTTTGGAGGTAAA
TCCTATGACAGGGGGGACTCCAAGGCTGAAAACGGAGCACAACATAACAGTGCAGATATCAGATGTCAATGATAA
CGCCCCCACTTTCACCCAAACCTCCTACACCCTGTTCGTCCGCGAGAACAACAGCCCCGCCCTGCACATCGGCAG
CGTCAGCGCCACAGACAGAGACTCAGGCACCAACGCCCAGGTCACCTACTCGCTGCTGCCGCCCCAGGACCCGCA
CCTGCCCCTCGCCTCCCTGGTCTCCATCAACGCAGACAACGGCCACCTGTTCGCCCTCAGGTCGCTGGACTACGA
GGCCCTGCGGGAGTTCGAGTTCCGCGTGAGCGCCACAGACCGCGGCTCCCCGGCTTTGAGCAGCGAGGCGCTGGT
GCGCGTGCTGGTGCTGGACGCCAACGACAACTCGCCCTTCGTGCTGTACCCGCTGCAGAACGGCTCCGCGCCCTG
CACTGAGCTGGTGCCCCGGGCGGCCGAGCCGGGCTACCTGGTGACCAAGGTGGTGGCGGTGGACGGCGACTCGGG
CCAGAATGCCTGGCTGTCGTACCAGCTGCTCAAGGCCACGGAGCCCGGGCTGTTCGGTGTGTGGGCGCACAATGG
CGAGGTGCGCACCGCCAGGCTGCTGAGCGAGCGCGACGCAGCCAAGCAGAGGCTGGTGGTGCTGGTCAAGGACAA
TGGCGAGCCTCCGCGCTCGGCCACCGCCACGCTGCACGTGCTCCTGGTGGACGGCTTCTCCCAGCCCTTCCTGCC
GCTCCCAGAGGCGGCCCCCGGCCAGACCCAGGCCAACTCGCTCACTGTCTACCTGGTGGTGGCAATATCCCTATG
TTTAATCTGTATTTCTTGCTTATTATATGTAAAGTTGAGCTTCTTTCTAGATATTAGGCCTTTGAATAAAATTCT
AT
```

OGTA116 (SEQ ID No: 4)

Peptide Source: 1D-GE, Gastric cancer

```
PFPGDGGTRQQSRHLAQLEPWGPWGSCAGTWPVSGAALNSNMGCKVLLNIGQQMLRRKVVDCSREETRLSRCLNT
FDLVALGVGSTLGAGVYVLAGAVARENAGPAIVISFLIAALASVLAGLCYGEFGARVPKTGSAYLYSYVTVGELW
AFITGWNLILSYIIGTSSVARAWSATFDELIGRPIGEFSRTHMTLNAPGVLAENPDIFAVIIILILTGLLTLGVK
ESAMVNKIFTCINVLVLGFIMVSGFVKGSVKNWQLTEEDFGNTSGRLCLNNDTKEGKPGVGGFMPFGFSGVLSGA
ATCFYAFVGFDCIATTGEEVKNPQKAIPVGIVASLLICFIAYFGVSAALTLMMPYFCLDNNSPLPDAFKHVGWEG
AKYAVAVGSLCALSASLLGSMFPMPRVIYAMAEDGLLFKFLANVNDRTKTPIIATLASGAVAAVMAFLFDLKDLV
DLMSIGTLLAYSLVAACVLVL
```

Mass Match Peptides (bold):

FIGURE 1 (CONT.)

Tandem Peptides (underline):
    FLANVNDR [27]

Peptide Source: 1D-GE, Hepatocellular carcinoma

<u>PFPGDGGTR</u>QQSRHLAQLEPWGPWGSCAGTWPVSGAALNSNMGCK<u>VLLNIGQQMLR</u>RKVVDCSREETRLSRCLNT
FDLVALGVGSTLGAGVYVLAGAVARENAGPAIVISFLIAALASVLAGLCYGEFGARVPKTGSAYLYSYVTVGELW
AFITGWNLILSYIIGTSSVARAWSATFDELIGRPIGEFSRTHMTLNAPGVLAENPDIFAVIIILILTGLLTLGVK
ESAMVNKIFTCINVLVLGFIMVSGFVKGSVKNWQLTEEDFGNTSGRLCLNNDTKEGKPGVGGFMPFGFSGVLSGA
ATCFYAFVGFDCIATTGEEVKNPQKAIPVGIVASLLICFIAYFGVSAALTLMMPYFCLDNNSPLPDAFKHVGWEG
AKYAVAVGSLCALSASLLGSMFPMPRVIYAMAEDGLLFK<u>FLANVNDR</u>TKTPIIATLASGAVAAVMAFLFDLKDLV
DLMSIGTLLAYSLVAACVLVL

Mass Match Peptides (bold):
    FLANVNDR [27]
    VIYAMAEDGLLFK [78]

Tandem Peptides (underline):
    FLANVNDR [27]
    PFPGDGGTR [56]
    VIYAMAEDGLLFK [78]
    VLLNIGQQMLR [79]

Peptide Source: 1D-GE, Pancreatic cancer

PFPGDGGTRQQSRHLAQLEPWGPWGSCAGTWPVSGAALNSNMGCK<u>VLLNIGQQMLR</u>RKVVDCSREETRLSRCLNT
FDLVALGVGSTLGAGVYVLAGAVARENAGPAIVISFLIAALASVLAGLCYGEFGARVPKTGSAYLYSYVTVGELW
AFITGWNLILSYIIGTSSVARAWSATFDELIGRPIGEFSRTHMTLNAPGVLAENPDIFAVIIILILTGLLTLGVK
ESAMVNKIFTCINVLVLGFIMVSGFVKGSVKNWQLTEEDFGNTSGRLCLNNDTKEGKPGVGGFMPFGFSGVLSGA
ATCFYAFVGFDCIATTGEEVKNPQKAIPVGIVASLLICFIAYFGVSAALTLMMPYFCLDNNSPLPDAFKHVGWEG
AKYAVAVGSLCALSASLLGSMFPMPRVIYAMAEDGLLFK<u>FLANVNDR</u>TKTPIIATLASGAVAAVMAFLFDLKDLV
DLMSIGTLLAYSLVAACVLVL

Mass Match Peptides (bold):
    FLANVNDR [27]
    VIYAMAEDGLLFK [78]

Tandem Peptides (underline):
    FLANVNDR [27]
    VLLNIGQQMLR [79]

DNA Sequence (SEQ ID No: 89)

CCCTTTCCAGGGGATGGGGGAACCAGACAGCAGTCCAGGCACCTGGCACAGCTGGAGCCCTGGGGTCCTTGGGGC
AGCTGCGCTGGGACGTGGCCAGTGTCAGGAGCCGCTCTGAACAGCAACATGGGGTGCAAAGTCCTGCTCAACATT
GGGCAGCAGATGCTGCGGCGGAAGGTGGTGGACTGTAGCCGGGAGGAGACGCGGCTGTCTCGCTGCCTGAACACT
TTTGATCTGGTGGCCCTCGGGGTGGGCAGCACACTGGGTGCTGGTGTCTACGTCCTGGCTGGAGCTGTGGCCCGT
GAGAATGCAGGCCCTGCCATTGTCATCTCCTTCCTGATCGCTGCGCTGGCCTCAGTGCTGGCTGGCCTGTGCTAT
GGCGAGTTTGGTGCTCGGGTCCCCAAGACGGGCTCAGCTTACCTCTACAGCTATGTCACCGTTGGAGAGCTCTGG
GCCTTCATCACCGGCTGGAACTTAATCCTCTCCTACATCATCGGTACTTCAAGCGTAGCGAGGGCCTGGAGCGCC
ACCTTCGACGAGCTGATAGGCAGACCCATCGGGGAGTTCTCACGGACACACATGACTCTGAACGCCCCCGGCGTG
CTGGCTGAAAACCCCGACATATTCGCAGTGATCATAATTCTCATCTTGACAGGACTTTTAACTCTTGGTGTGAAA
GAGTCGGCCATGGTCAACAAAATATTCACTTGTATTAACGTCCTGGTCCTGGGCTTCATAATGGTGTCAGGATTT

FIGURE 1 (CONT.)

```
GTGAAAGGATCGGTTAAAAACTGGCAGCTCACGGAGGAGGATTTTGGGAACACATCAGGCCGTCTCTGTTTGAAC
AATGACACAAAAGAAGGGAAGCCCGGTGTTGGTGGATTCATGCCCTTCGGGTTCTCTGGTGTCCTGTCGGGGGCA
GCGACTTGCTTCTATGCCTTCGTGGGCTTTGACTGCATCGCCACCACAGGTGAAGAGGTGAAGAACCCACAGAAG
GCCATCCCCGTGGGGATCGTGGCGTCCCTCTTGATCTGCTTCATCGCCTACTTTGGGGTGTCGGCTGCCCTCACG
CTCATGATGCCCTACTTCTGCCTGGACAATAACAGCCCCCTGCCCGACGCCTTTAAGCACGTGGGCTGGGAAGGT
GCCAAGTACGCAGTGGCCGTGGGCTCCCTCTGCGCTCTTCCGCCAGTCTTCTAGGTTCCATGTTTCCCATGCCT
CGGGTTATCTATGCCATGGCTGAGGATGGACTGCTATTTAAATTCTTAGCCAACGTCAATGATAGGACCAAAACA
CCAATAATCGCCACATTAGCCTCGGGTGCCGTTGCTGCTGTGATGGCCTTCCTCTTTGACCTGAAGGACTTGGTG
GACCTCATGTCCATTGGCACTCTCCTGGCTTACTCGTTGGTGGCTGCCTGTGTGTTGGTCTTACG
```

OGTA194 (SEQ ID No: 5)

Peptide Source: 1D-GE, B-cell non-Hodgkin's lymphoma

```
MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYKESGVFEGIPTYR
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILNP
```

Mass Match Peptides (bold):
    ESGVFEGIPTYR [25]

Tandem Peptides (underline):
    ESGVFEGIPTYR [25]

Peptide Source: 1D-GE, Breast cancer

```
MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYKESGVFEGIPTYR
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN
```

Mass Match Peptides (bold):
    ESGVFEGIPTYR [25]
    GEKPQVR [31]
    GPYVYR [32]
    IHLVDK [39]
    LIMTLAFTTLGER [45]
    LQLSLYMK [48]
    TFQFQPSK [71]
    TVGEIMWGYK [76]
    WNGLSK [84]
    YFPGMFPFK [85]

Tandem Peptides (underline):
    ESGVFEGIPTYR [25]
    SQPPNQHPTLK [69]

Peptide Source: 1D-GE, Colorectal cancer

FIGURE 1 (CONT.)

MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYK<u>DPLVNLINK</u>YFPGMFPFKDKFGLFAELNNSDSGLFTVFTGV
QNISRIHLVDKWNGLSKVDFWHSDQCNMINGTSGQMWPPFMTPESSLEFYSPEACRSMKLMYK<u>ESGVFEGIPTYR</u>
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN

Mass Match Peptides (bone):
    DPLVNLINK [23]
    ESGVFEGIPTYR [25]
    IDPSSLSFNMWK [38]
    LIMTLAFTTLGER [45]
    TFQFQPSK [71]

Tandem Peptides (underline):
    DPLVNLINK [23]
    ESGVFEGIPTYR [25]
    TFQFQPSK [71]

Peptide Source: 1D-GE, Hepatocellular carcinoma

MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYK<u>DPLVNLINK</u>YFPGMFPFKDKFGLFAELNNSDSGLFTVFTGV
QNISRIHLVDKWNGLSKVDFWHSDQCNMINGTSGQMWPPFMTPESSLEFYSPEACRSMKLMYK<u>ESGVFEGIPTYR</u>
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN

Mass Match Peptides (bold):
    DPLVNLINK [23]
    ESGVFEGIPTYR [25]
    IDPSSLSFNMWK [38]
    LQLSLYMK [48]
    SNITFNNNDTVSFLEYR [68]
    TFQFQPSK [71]

Tandem Peptides (underline):
    DPLVNLINK [23]
    ESGVFEGIPTYR [25]

Peptide Source: 1D-GE, Lung cancer

MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYKESGVFEGIPTYR
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN

Mass Match Peptides (bold):
    ESGVFEGIPTYR [25]

FIGURE 1 (CONT.)

Tandem Peptides (underline):
    ESGVFEGIPTYR [25]

Peptide Source: 1D-GE, Melanoma

MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYKESGVFEGIPTYR
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN

Mass Match Peptides (bold):
    DPLVNLINK [23]
    ESGVFEGIPTYR [25]
    TFQFQPSK [71]

Tandem Peptides (underline):
    ESGVFEGIPTYR [25]
    TFQFQPSK [71]

Peptide Source: 1D-GE, Ovarian cancer

MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYKESGVFEGIPTYR
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN

Mass Match Peptides (bold):
    DPLVNLINK [23]
    ESGVFEGIPTYR [25]
    GPYVYR [32]
    LIMTLAFTTLGER [45]

Tandem Peptides (underline):
    ESGVFEGIPTYR [25]

Peptide Source: 1D-GE, Pancreatic cancer

MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYKESGVFEGIPTYR
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN

Mass Match Peptides (bold):
    DPLVNLINK [23]

FIGURE 1 (CONT.)

```
    ESGVFEGIPTYR [25]
    GPYVYR [32]
    LIMTLAFTTLGER [45]
    LQLSLYMK [48]
    TFQFQPSK [71]
    YFPGMFPFK [85]
```
Tandem Peptides (underline):
```
    DPLVNLINK [23]
    ESGVFEGIPTYR [25]
```

Peptide Source: 1D-GE, Prostate cancer

MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYK<u>ESGVFEGIPTYR</u>
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN

Mass Match Peptides (bold):
```
    ESGVFEGIPTYR [25]
    GEKPQVR [31]
    GPYVYR [32]
    TVGEIMWGYK [76]
```
Tandem Peptides (underline):
```
    ESGVFEGIPTYR [25]
```

Peptide Source: 1D-GE, Renal cell cancer

MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYKESGVFEGIPTYR
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN

Mass Match Peptides (bold):
```
    DPLVNLINK [23]
    ESGVFEGIPTYR [25]
    LIMTLAFTTLGER [45]
    TFQFQPSK [71]
    TVGEIMWGYK [76]
```
Tandem Peptides (underline):
```
    ESGVFEGIPTYR [25]
```

Peptide Source: iTRAQ, Non-small cell lung cancer

MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN

FIGURE 1 (CONT.)

```
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYKESGVFEGIPTYR
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN
```

Mass Match Peptides (bold):
    QQVLK [94]

Tandem Peptides (underline):
    QQVLK [94]

Peptide Source: iTRAQ, Ovarian cancer

```
MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYKESGVFEGIPTYR
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN
```

Mass Match Peptides (bold):
    QQVLK [94]

Tandem Peptides (underline):
    QQVLK [94]

Peptide Source: iTRAQ, Small cell lung cancer

```
MGCSAKARWAAGALGVAGLLCAVLGAVMIVMVPSLIKQQVLKNVRIDPSSLSFNMWKEIPIPFYLSVYFFDVMNP
SEILKGEKPQVRERGPYVYREFRHKSNITFNNNDTVSFLEYRTFQFQPSKSHGSESDYIVMPNILVLGAAVMMEN
KPMTLKLIMTLAFTTLGERAFMNRTVGEIMWGYKDPLVNLINKYFPGMFPFKDKFGLFAELNNSDSGLFTVFTGV
QNISRIHLVDKWNGLSKVDFWHSDQCNMINGTSGQMWPPFMTPESSLEFYSPEACRSMKLMYKESGVFEGIPTYR
FVAPKTLFANGSIYPPNEGFCPCLESGIQNVSTCRFSAPLFLSHPHFLNADPVLAEAVTGLHPNQEAHSLFLDIH
PVTGIPMNCSVKLQLSLYMKSVAGIGQTGKIEPVVLPLLWFAESGAMEGETLHTFYTQLVLMPKVMHYAQYVLLA
LGCVLLLVPVICQIRSQPPNQHPTLKSSKNATIGSVAPSLQVSLEATRNAIYFGVVVKRAQRIRRPFRPILN
```

Mass Match Peptides (bold):
    QQVLK [94]

Tandem Peptides (underline):
    QQVLK [94]

DNA Sequence (SEQ ID No: 90)

```
GTCGCCGTCCCCGTCTCCTGCCAGGCGCGGAGCCCTGCGAGCCGCGGGTGGGCCCCAGGCGCGCAGACATGGGCT
GCTCCGCCAAAGCGCGCTGGGCTGCCGGGGCGCTGGGCGTCGCGGGCTACTGTGCGCTGTGCTGGGCGCTGTCA
TGATCGTGATGGTGCCGTCGCTCATCAAGCAGCAGGTCCTTAAGAACGTGCGCATCGACCCCAGTAGCCTGTCCT
TCAACATGTGGAAGGAGATCCCTATCCCCTTCTATCTCTCCGTCTACTTCTTTGACGTCATGAACCCCAGCGAGA
TCCTGAAGGGCGAGAAGCCGCAGGTGCGGGAGCGCGGGCCCTACGTGTACAGGGAGTTCAGGCACAAAAGCAACA
TCACCTTCAACAACGACACCGTGTCCTTCCTCGAGTACCGCACCTTCCAGTTCCAGCCCTCCAAGTCCCACG
GCTCGGAGAGCGACTACATCGTCATGCCCAACATCCTGGTCTTGGGTGCGGCGGTGATGATGGAGAATAAGCCCA
TGACCCTGAAGCTCATCATGACCTTGGCATTCACCACCCTCGGCGAACGTGCCTTCATGAACCGCACTGTGGGTG
```

FIGURE 1 (CONT.)

```
AGATCATGTGGGGCTACAAGGACCCCCTTGTGAATCTCATCAACAAGTACTTTCCAGGCATGTTCCCCTTCAAGG
ACAAGTTCGGATTATTTGCTGAGCTCAACAACTCCGACTCTGGGCTCTTCACGGTGTTCACGGGGGTCCAGAACA
TCAGCAGGATCCACCTCGTGGACAAGTGGAACGGGCTGAGCAAGGTTGACTTCTGGCATTCCGATCAGTGCAACA
TGATCAATGGAACTTCTGGGCAAATGTGGCCGCCCTTCATGACTCCTGAGTCCTCGCTGGAGTTCTACAGCCCGG
AGGCCTGCCGATCCATGAAGCTAATGTACAAGGAGTCAGGGGTGTTTGAAGGCATCCCCACCTATCGCTTCGTGG
CTCCCAAAACCCTGTTTGCCAACGGGTCCATCTACCCACCCAACGAAGGCTTCTGCCCGTGCCTGGAGTCTGGAA
TTCAGAACGTCAGCACCTGCAGGTTCAGTGCCCCCTTGTTTCTCTCCCATCCTCACTTCCTCAACGCTGACCCGG
TTCTGGCAGAAGCGGTGACTGGCCTGCACCCTAACCAGGAGGCACACTCCTTGTTCCTGGACATCCACCCGGTCA
CGGGAATCCCCATGAACTGCTCTGTGAAACTGCAGCTGAGCCTCTACATGAAATCTGTCGCAGGCATTGGACAAA
CTGGGAAGATTGAGCCTGTGGTCCTGCCGCTGCTCTGGTTTGCAGAGAGCGGGGCCATGGAGGGGGAGACTCTTC
ACACATTCTACACTCAGCTGGTGTTGATGCCCAAGGTGATGCACTATGCCCAGTACGTCCTCCTGGCGCTGGGCT
GCGTCCTGCTGCTGGTCCCTGTCATCTGCCAAATCCGGAGCCAACCCCCAAATCAGCATCCCACCCTCAAATCCA
GTAAGAATGCTACGATCGGCAGTGTGGCTCCCTCCCTGCAGGTTTCACTGGAGGCCACGAGAAATGCTATTTATT
TTGGAGTAGTAGTAAAAAGGGCTCAAAGGATAAGGAGGCCATTCAGGCCTATTCTGAATCCCTGATGACATCAGC
TCCCAAGGGCTCTGTGCTGCAGGAAGCAAAACTGTAGGGTCCTGAGGACACCGTGAGCCAGCCAGGCCTGGCCGC
TGGGCCTGACCGGCCCCCCAGCCCCTACACCCCGCTTCTCCCGGACTCTCCCAGCGGACAGCCCCCAGCCCCAC
AGCCTGAGCCTCCCAGCTGCCATGTGCCTGTTGCACACCTGCACACACGCCCTGGCACACATACACACATGCGTG
CAGGCTTGTGCAGACACTCAGGGATGGAGCTGCTGCTGAAGGGACTTGTAGGGAGAGGCTCGTCAACAAGCACTG
TTCTGGAACCTTCTCTCCACGTGGCCCACAGGCCTGACCACAGGGGCTGTGGGTCCTGCGTCCCCTTCCTCGGGT
GAGCCTGGCCTGTCCCGTTCAGCCGTTGGGCCCAGGCTTCCTCCCCTCCAAGGTGAAACACTGCAGTCCCGGTGT
GGTGGCTCCCCATGCAGGACGGGCCAGGCTGGGAGTGCCGCCTTCCTGTGCCAAATTCAGTGGGGACTCAGTGCC
CAGGCCCTGGCCACGAGCTTTGGCCTTGGTCTACCTGCCAGGCCAGGCAAAGCGCCTTTACACAGGCCTCGGAAA
ACAATGGAGTGAGCACAAGATGCCCTGTGCAGCTGCCCGAGGGTCTCCGCCCACCCCGGCCGGACTTTGATCCCC
CCGAAGTCTTCACAGGCACTGCATCGGGTTGTCTGGCGCCCTTTTCCTCCAGCCTAAACTGACATCATCCTATGG
ACTGAGCCGGCCACTCTCTGGCCGAAGTGGCCGCAGGCTGTGCCCCCGAGCTGCCCCCACCCCCTCACAGGGTCC
CTCAGATTATAGGTGCCCAGGCTGAGGTGAAGAGGCCTGGGGGCCCTGCCTTCCGGGCGCTCCTGGACCCTGGGG
CAAACCTGTGACCCTTTTCTACTGGAATAGAAATGAGTTTTATCATCTTTGAAAAATAATTCACTCTTGAAGTAA
TAAACGTTTAAAAAAATGG
```

PROTEINS

RELATED APPLICATIONS

The present application is a Continuation of co-pending PCT Application No. PCT/GB2008/050126 filed Feb. 25, 2008, which in turn, claims priority from U.S. Provisional Application Ser. No. 60/903,462 filed Feb. 26, 2007. Applicants claim the benefits of 35 U.S.C. §120 as to the said PCT application and priority under 35 U.S.C. §119 as to the said U.S. Provisional application, and the entire disclosures of both applications are incorporated herein by reference in their entireties.

INTRODUCTION

The present invention relates to the identification of membrane proteins associated with B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer which have utility as markers for B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer and breast cancer, colorectal cancer, gastric cancer, hepatocellular carcinoma, lung cancer, melanoma, osteosarcoma, ovarian cancer, pancreatic cancer, prostate cancer and renal cell cancer metastases and which also form biological targets against which therapeutic antibodies (or other affinity reagents) or other pharmaceutical agents can be made.

BACKGROUND OF THE INVENTION

Acute Lymphocytic Leukaemia

Each year, about 35,000 new cases of all types of leukaemia are diagnosed in the USA.

Of these, about 4,000 will be acute lymphocytic leukaemia (ALL). Although this is a leukaemia that occurs mostly in children, about one-third, or 1300 cases, will occur in adults. About 1,500 people will die of ALL in the USA each year; two-thirds of them will be adults. The risk of ALL is lowest between the ages of 25 and 50 and then begins to pick up.

Acute Lymphocytic Leukaemia Diagnosis

Diagnostic tests for ALL include blood cell count, bone marrow aspiration, bone marrow biopsy, excisional lymph node biopsy, blood chemistry tests and lumbar puncture. Other lab tests include routine microscopic exam, cytochemistry, flow cytometry, immunocytochemistry, cytogenetics, molecular genetic studies, and gene-expression profiling. Imaging tests such as chest x-ray, computed tomography (CT) scans, magnetic resonance imaging (MRI), gallium scans, bone scans, and ultrasound may also be carried out.

Acute Lymphocytic Leukaemia Staging

Leukaemia involves all the bone marrow and, in many cases, it has also spread to other organs. Lab tests focus on finding out the exact type (and subtype) of leukaemia. This in turn helps predict which treatments will work best and the prognosis for the patient.

There are 3 subtypes for ALL according to the French-American-British (FAB) classification. The original FAB system was based only on the way the leukaemic cells looked under the microscope after they were routinely processed or cytochemically stained. More recently, doctors have found that cytogenetic studies, flow cytometry, and molecular genetic studies provide more information that is sometimes useful in classifying ALL and predicting the patient's prognosis. Now the subtypes of ALL are: early pre-B ALL, common ALL, pre-B-cell ALL, mature B-cell ALL (Burkitt leukaemia), pre-T-cell ALL and mature T-cell ALL. T-cell ALL has the best prognosis, mature B-cell ALL the worst, and pre-B-cell ALL is intermediate.

One of the most important factors that affects outcome is a translocation between chromosomes 9 and 22 (Philadelphia chromosome). People with this translocation (20% to 25%) have a worse outcome than those without it. Another translocation that carries a poor outlook is one between chromosomes 4 and 11, which occurs in about 5% of patients.

Acute Lymphocytic Leukaemia Treatment

Chemotherapy is the major treatment for ALL. Treatments are given in the following phases: remission induction, consolidation, maintenance therapy and central nervous system (CNS) prophylaxis. Chemotherapeutic agents used for remission induction and consolidation include cyclophosphamide, vincristine, dexamethasone or prednisone, L-asparaginase and doxorubicin (Adriamycin) or daunorubicin. Maintenance therapy consists of methotrexate with 6-mercaptopurine (6-MP), often combined with vincristine and prednisone. CNS prophylaxis involves methotrexate and/or cytarabine. In general, about 80% of patients will respond completely to these treatments. Unfortunately, about half of these patients relapse, so the overall cure rate is around 30%. If leukaemias recur after treatment, they will most often do so in the bone marrow and blood. Occasionally, the brain or spinal fluid will be the first place they recur. If the leukaemia is refractory (which happens in about 15%-20% of cases) then newer or more intensive doses of drugs may be tried, although they are less likely to work. A stem cell transplant may be attempted if the leukaemia can be put into remission. It is possible for a patient with recurrent leukaemia to go into remission again, although it may be only temporary. In this situation, a stem cell transplant is considered after more induction chemotherapy. If the leukaemia is persistent, eventually chemotherapy treatment becomes unhelpful.

Radiation therapy is sometimes used to treat leukaemia that has spread to the brain and spinal fluid or to the testicles. Radiation to the whole body is often an important part of treatment before bone marrow or peripheral blood stem cell transplantation.

Clinical trials are being conducted to see whether better outcomes are achieved using a combination of chemotherapy and imatinib mesylate (Gleevec), a drug which targets cells that have the Philadelphia chromosome (9-22 translocation or bcr-abl gene fusion). Another drug, dasatinib, approved for treatment of ALL, has the same mode of action as imatinib but appears to be more potent and can act against leukaemia cells that have become resistant to imatinib.

Non-Hodgkin's Lymphoma

Non-Hodgkin's lymphoma (NHL) is a cancer of lymphoid tissue. In the USA, 85% of all cases of non-Hodgkin's lymphoma derive from B lymphocytes (B-cell) and 15% from T lymphocytes (T-cell). There are about 59,000 new cases of NHL in the USA each year, with around 19,000 deaths. This cancer is more common in men than in women. A person's risk of getting NHL during his or her lifetime is 1 in 50. The risk of dying of this disease is about 1 in 100. Since the early 1970s, incidence rates for non-Hodgkin lymphoma have nearly doubled. More recently, incidence rates have stabilized due, perhaps, to the decline in AIDS-related NHL.

B-Cell Lymphomas:

About 33% of all non-Hodgkin's lymphomas in the USA are diffuse large B-cell lymphomas. About 14% are follicular lymphomas. Chronic lymphocytic leukaemia (CLL) and small lymphocytic lymphoma (SLL) account for 24% of all lymphomas. Only about 2% of lymphomas are mantle cell lymphomas. All marginal zone lymphomas account for about 4% of lymphomas. Primary mediastinal B-cell lymphoma accounts for about 2% of all lymphomas. Burkitt's lymphoma makes up about 1% to 2% of all lymphomas. Lymphoplasmocytic lymphoma (Waldenstrom macroglobulinemia) accounts for 1-2% of lymphomas. Hairy cell leukaemia is rare—about 1,000 people in the USA are diagnosed with this type each year. Although primary central nervous system (CNS) lymphoma was a rare tumour in the past, it has become more common in patients with AIDS.

Non-Hodgkin's Lymphoma Diagnosis

NHL may cause many different signs and symptoms, depending on where it is found in the body. A biopsy is the only way to tell for sure if cancer is present. Types of biopsy include excisional or incisional biopsy, fine needle aspiration (FNA) biopsy, bone marrow aspiration and biopsy, and lumbar puncture. Lab tests including immunohistochemistry, flow cytometry, cytogenetics, molecular genetic studies and blood tests can also be performed. Imaging tests that may be used include chest x-ray, computed tomography (CT) scan, magnetic resonance imaging (MRI) scan, positron emission tomography (PET) scan, gallium scan, bone scan, and ultrasound.

Non-Hodgkin's Lymphoma Staging

Survival statistics vary widely by cell type and stage of disease at the time of diagnosis. However, the overall 5-year relative survival rate for people with non-Hodgkin's lymphoma is 60%, and 10-year relative survival is 49%.

Non-Hodgkin's lymphoma is staged using the Ann Arbor staging system stages I-IV. The International Prognostic Index (IPI) helps predict how quickly the lymphoma might grow and how well a patient might respond to treatment. It is mainly used in patients with fast growing lymphomas. Over 75% of people in the lowest group will live longer than 5 years, whereas only 30% of people in the highest group live 5 years.

Survival rates for B-Cell Lymphomas:

Diffuse large B-cell lymphoma can be cured in around 40% to 50% of patients. Follicular lymphomas are not considered curable but are slow growing, and the 5-year survival rate is around 60% to 70%. Over time, about one third of follicular lymphomas change into a fast growing diffuse B-cell lymphoma. Chronic lymphocytic leukaemia (CLL) and small lymphocytic lymphoma (SLL) are not considered curable but depending on the stage and growth rate of the disease, most patients can live well over 10 years with this lymphoma. Only 20% of patients with mantle cell lymphoma survive at least 5 years. Marginal zone lymphomas are often curable. About half of patients with primary mediastinal B-cell lymphoma can be cured. Although Burkitt's lymphoma is a fast growing lymphoma, over half of patients can be cured by intensive chemotherapy. Although lymphoplasmocytic lymphoma (Waldenstrom macroglobulinemia) isn't curable, most patients live longer than 5 years. Hairy cell leukaemia can usually be treated successfully. The outlook for people with primary CNS lymphoma is poor but about 30% to 50% of people can live at least 5 years.

Non-Hodgkin's Lymphoma Treatment

Surgery is not often used to treat NHL. It has been used to treat lymphomas that start in organs such as the stomach or thyroid, but only if it has not spread beyond these organs. External beam radiation therapy is often the main treatment for early stage lymphomas, and is often used along with chemotherapy. Chemotherapeutic drugs used include a combination of cyclophosphamide, doxorubicin, vincristine and prednisone known as CHOP, chlorambucil, fludarabine, and etoposide. Immunotherapy using either interferon or monoclonal antibodies such as rituximab can also sometimes be used as a treatment. Bone marrow or peripheral blood stem cell transplantation (SCT) is used for patients when standard treatment has not worked.

Treatment of B-cell Lymphomas:

The main treatment for diffuse large B-cell lymphoma is chemotherapy with CHOP with the addition of rituximab. Radiation therapy may also be added. Follicular lymphoma has not been shown to be curable by any of the standard treatments. Radiation therapy, chemotherapy and/or monoclonal antibodies can be used, with the point of therapy being to control the disease for as long as possible while causing the fewest side effects. Chronic lymphocytic leukaemia (CLL) and small lymphocytic lymphoma (SLL) are also not considered curable and the treatment is the same as for follicular lymphoma. There is also no curative treatment for mantle cell lymphoma which is often fatal. Radiation therapy and chemotherapy are used to treat extranodal marginal zone B-cell lymphomas. Nodal marginal zone B-cell lymphoma and splenic marginal zone B-cell lymphoma are generally low-grade lymphomas and are treated with either observation or low-intensity chemotherapy. Primary mediastinal B-cell lymphoma is treated like localized diffuse large B-cell lymphoma. Burkitt's lymphoma is a very fast growing lymphoma that is treated intensely with chemotherapy. The main treatment for lymphoplasmocytic lymphoma (Waldenstrom macroglobulinemia) is chemotherapy or rituximab. Hairy cell leukaemia is a slow growing lymphoma that invades the spleen and lymph nodes as well as the blood and can be treated with chemotherapy.

Breast Cancer

Globally, breast cancer is both the most common cancer (10% of all cancer cases) and the leading cause of cancer death (6% of cancer deaths) in women. Global incidence of breast cancer is over 1 million cases per year, with about 400,000 deaths. Women in North America have the highest rate of breast cancer in the world (over 200,000 new cases per year, with about 40,000 deaths). The chance of developing invasive breast cancer at some time in a woman's life is about 1 in 8. Breast cancer incidence increases with age, rising sharply after age 40. In the USA, about 77% of invasive breast cancers occur in women over age 50. It has been estimated that approximately US$8.1 billion is spent in the USA each year on treating breast cancer.

Breast Cancer Diagnosis

Early diagnosis improves the likelihood that treatment will be successful. Screening methods such as mammograms, clinical breast examinations and breast self-examinations are useful in detecting breast cancer. Current diagnostic methods include breast ultrasound, ductogram, full-field digital mammography (FFDM), scintimammography and MRI. A biopsy (fine needle aspiration biopsy, core biopsy or surgical biopsy) is then performed to confirm the presence of breast cancer. Imaging tests such as a chest x-ray, bone scan, CT, MRI and PET are used to detect if the breast cancer has spread.

Breast Cancer Staging

Breast cancer is staged using the American Joint Committee on Cancer (AJCC) TNM system—Stage 0—Stage IV. Ductal carcinoma in situ (DCIS), a non-invasive cancer which accounts for 20% of new breast cancer cases is Stage 0. Nearly all women diagnosed at this early stage of breast cancer can be cured. Infiltrating (invasive) ductal carcinoma (IDC), which accounts for 80% of invasive breast cancer and infiltrating (invasive) lobular carcinoma (ILC), which accounts for 5% of invasive breast cancers are more severe Stage I-IV cancers and can metastasise.

Breast Cancer Treatment

Breast-conserving surgery (lumpectomy) or mastectomy are the usual treatments for breast cancer. For stage I or II breast cancer, breast-conserving surgery is as effective as mastectomy. Patients can then undergo reconstructive surgery. Axillary lymph node sampling and removal or sentinel lymph node biopsy (SLNB) is performed to see if the cancer has spread to the lymph nodes.

Neoadjuvant chemotherapy can be given before surgery to shrink large cancers. Adjuvant chemotherapy after surgery reduces the risk of breast cancer recurrence. Chemotherapy can also be used as the main treatment for women whose cancer has spread outside the breast and underarm area. Chemotherapeutic agents used include anthracyclines (e.g. methotrexate, fluorouracil, doxorubicin, and epirubicin), taxanes (e.g. paclitaxel, docetaxel, vinorelbine) and alkylating agents (e.g. cyclophosphamide).

Radiation therapy (usually external beam radiation but sometimes brachytherapy) is given once chemotherapy is complete.

Hormone therapy with selective oestrogen receptor modulators (e.g. tamoxifen) can be given to women with oestrogen receptor positive breast cancers. Taking tamoxifen after surgery for 5 years can reduce recurrence by about 50% in women with early breast cancer. Aromatase inhibitors such as exemestane, letrozole or anastrozole can also be used.

Women with HER2 positive cancers (about ⅓ of breast cancers) can be given biological response modifiers such as trastuzumab (Herceptin). Clinical trials have shown that adding trastuzumab to chemotherapy lowers the recurrence rate and death rate over chemotherapy alone after surgery in women with HER2 positive early breast cancers.

Breast Cancer Survival by Stage

This table shows survival by stage based on patients diagnosed between 1995 and 1998. The survival rates now should be slightly higher.

| Stage | 5-year Relative Survival Rate |
| --- | --- |
| 0 | 100% |
| I | 100% |
| IIA | 92% |
| IIB | 81% |
| IIIA | 67% |
| IIIB | 54% |
| IV | 20% |

Colorectal Cancer

Colorectal cancer (CRC) is one of the leading causes of cancer-related morbidity and mortality, responsible for an estimated half a million deaths per year, mostly in Western, well developed countries. In these territories, CRC is the third most common malignancy (estimated number of new cases per annum in USA and EU is approximately 350,000 per year). Estimated healthcare costs related to treatment for colorectal cancer in the United States are more than $8 billion.

Colorectal Cancer Diagnosis

Today, the fecal occult blood test and colonoscopy, a highly invasive procedure, are the most frequently used screening and diagnostic methods for colorectal cancer. Other diagnostic tools include Flexible Sigmoidoscopy (allowing the observation of only about half of the colon) and Double Contrast Barium Enema (DCBE, to obtain X-ray images).

Colorectal Cancer Staging

CRC has four distinct stages: patients with stage I disease have a five-year survival rate of >90%, while those with metastatic stage IV disease have a <5% survival rate according to the US National Institutes of Health (NIH).

Colorectal Cancer Treatment

Once CRC has been diagnosed, the correct treatment needs to be selected. Surgery is usually the main treatment for rectal cancer, although radiation and chemotherapy will often be given before surgery. Possible side effects of surgery include bleeding from the surgery, deep venous thrombosis, and damage to nearby organs during the operation.

Currently, 60 percent of colorectal cancer patients receive chemotherapy to treat their disease; however, this form of treatment only benefits a few percent of the population, while carrying with it high risks of toxicity, thus demonstrating a need to better define the patient selection criteria.

Colorectal cancer has a 30 to 40 percent recurrence rate within an average of 18 months after primary diagnosis. As with all cancers, the earlier it is detected the more likely it can be cured, especially as pathologists have recognized that the majority of CRC tumours develop in a series of well-defined stages from benign adenomas.

Colon Cancer Survival by Stage

| Stage | Survival Rate |
| --- | --- |
| I | 93% |
| IIA | 85% |
| IIB | 72% |
| IIIA | 83% |
| IIIB | 64% |
| IIIC | 44% |
| IV | 8% |

Gastric Cancer

Gastric cancer is the second-leading cause of cancer-related deaths in the world, with about 700,000 deaths per year, mostly in less developed countries. In the USA, about 22,000 people are diagnosed with gastric cancer each year, with about 11,000 deaths. This figure is approximately ten times higher in Japan. Two thirds of people diagnosed with gastric cancer are older than 65.

Gastric Cancer Diagnosis

Early stage gastric cancer rarely causes symptoms so only about 10-20% of gastric cancers in the USA are found in the early stages, before they have spread to other areas of the body. Studies in the USA have not found mass screening for gastric cancer to be useful because the disease is not that common. Endoscopy followed by a biopsy is the main procedure used to diagnose gastric cancer. Other diagnostic methods include barium upper gastrointestinal radiographs, endoscopic ultrasound, CT scan, PET scan, MRI scan, chest x-ray, laparoscopy, complete blood count (CBC) test and fecal occult blood test.

Gastric Cancer Staging

Gastric cancer is staged using the American Joint Commission on Cancer (AJCC) TNM system—Stage0—Stage IV. Patients with stage 0 disease have a 5-year survival rate of >90%, while there is usually no cure for patients with stage IV disease where the 5-year survival rate is only 7%. The overall 5-year relative survival rate of people with gastric cancer in the USA is about 23%. The 5-year survival rate for cancers of the proximal stomach is lower than for cancers in the distal stomach.

Gastric Cancer Treatment

Surgery is the only way to cure gastric cancer. There are three types of surgery used—endoscopic mucosal resection (only for early stage gastric cancer), subtotal gastrectomy or total gastrectomy. Gastric cancer often spreads to lymph nodes so these must also be removed. If the cancer has extended to the spleen, the spleen is also removed. Surgery for gastric cancer is difficult and complications can occur.

Chemotherapy may be given as the primary treatment for gastric cancer that has spread to distant organs. Chemotherapy together with external beam radiation therapy may delay cancer recurrence and extend the life span of people with less advanced gastric cancer, especially when the cancer could not be removed completely by surgery. Chemotherapeutic agents used include fluorouracil, doxorubicin, methotrexate, etoposide and cisplatin. More recently, imatinib mesylate (Gleevec) has been trialled in gastrointestinal stromal tumours (GIST), improving progression free survival.

Gastric Cancer Survival by Stage

| Stage | Survival Rate |
|-------|---------------|
| 0     | >90%          |
| IA    | 80%           |
| IB    | 60%           |
| II    | 34%           |
| IIIA  | 17%           |
| IIIB  | 12%           |
| IV    | 7%            |

Hepatocellular Carcinoma (HCC)

Hepatocellular carcinoma (HCC) arises from the main cells of the liver (the hepatocytes) and accounts for around 80% of all cases of liver cancer. It is usually confined to the liver and is associated with cirrhosis in 50% to 80% of patients. Hepatocellular carcinoma is about 3 times more common in males than in females. Chronic infection with hepatitis B virus (HBV) or hepatitis C virus (HCV) is a major cause of HCC and is responsible for making liver cancer the most common cancer in many parts of the world. In the United States, hepatitis C infection is responsible for about 50% to 60% of all liver cancers and hepatitis B is responsible for another 20%. Exposure to Aflatoxins is also a cause of HCC, mostly in warmer and tropical countries. Liver cancer accounts for about 5.8% of all cancer cases globally (about 626,000 cases) and 8.9% of deaths per year (about 598,000). It is the 3rd most common cause of cancer-related death in both men and women worldwide. HCC is predominantly found in Asia and Africa, which account for 80% of cases. In the USA, there are approximately 18,500 new cases of HCC and 16,000 deaths per year. About 85% of people diagnosed with liver cancer are between 45 and 85 years of age. About 4% are between 35 and 44 years of age and only 2.4% are younger than 35.

Hepatocellular Carcinoma Diagnosis

Since symptoms of liver cancer often do not appear until the disease is advanced, only a small number of liver cancers are found in the early stages and can be removed with surgery. Many signs and symptoms of liver cancer are relatively non-specific—that is, they can be caused by other cancers or by non-cancerous diseases. Imaging tests such as ultrasound, computed tomography (CT), magnetic resonance imaging (MRI) and angiography are commonly used to diagnose HCC. Other diagnostic tools include laparoscopy, biopsy, alpha-fetoprotein (AFP) blood test, liver function tests (LFTs), prothrombin time (PT) and tests for hepatitis B and C.

Hepatocellular Carcinoma Staging

HCC has four stages, stage I to stage IV according to the American Joint Committee on Cancer (AJCC) TNM system. HCC can be classified as localized resectable, localized unresectable or advanced. The overall 5-year relative survival rate for liver cancer is about 9%. One reason for this low survival rate is that most patients with liver cancer also have cirrhosis of the liver, which itself can be fatal (people with liver cancer and class C cirrhosis are generally too sick for any treatment and usually die in a few months). The 5 year survival for localized resectable HCC following surgery is between 40% and 70%. For advanced HCC there is no standard treatment and the 5 year survival rate is less than 5%. Survival continues to drop after diagnosis and treatment so that by 10 years it is less than 2.5%.

Hepatocellular Carcinoma Treatment

Treatment of liver cancer depends on the size of the tumour and whether the patient has cirrhosis. At this time, surgery, either by resection or liver transplantation, offers the only chance to cure a liver cancer. People without cirrhosis can do well with surgical removal of the tumour. However, in many cases, it might not be possible to safely remove a localized liver cancer. Less than 30% of the patients having explorative surgery are able to have their cancer completely removed by surgery. Partial hepatectomy results in a 5-year survival of 30% to 40%. If there is cirrhosis, or a very large tumour, most experts recommend liver transplantation as the main treatment. The 5-year survival for liver transplantation patients is around 70% but the opportunities for liver transplantation are limited.

Other treatments include radiofrequency ablation (RFA), ethanol ablation, cryosurgery, hepatic artery embolization, chemoembolization or three-dimensional conformal radiation therapy (3DCRT). Chemotherapy can also be used but shrinks fewer than 1 in 5 tumours. This may be improved by hepatic artery infusion (HAI). Chemotherapeutic agents used include Adriamycin, VP-16, Cisplatinum, Mitomycin, 5-FU and Leucovorin.

The prognosis for any treated primary liver cancer patient with progressing, recurring, or relapsing disease is poor. Treatment of liver cancer that returns after initial therapy depends on many factors, including the site of the recurrence, the type of initial treatment, and the functioning of the liver. Patients with localized resectable disease that recurs in the same spot may be eligible for further surgery.

Lung Cancer

Lung cancer is the most common form of cancer worldwide (accounting for about 12% of cancer cases) and the main cause of death from cancer (accounting for about 18% of deaths). Global incidence of lung cancer is over 1,300,000 per year, with the number of deaths over 1,100,000. In the USA, there are about 170,000 new cases per year (about 13% of all cancers), with about 160,000 deaths (about 28% of cancer deaths). Lung cancer is much more prevalent among men than women. Nearly 70% of people diagnosed with lung cancer are older than 65; fewer than 3% of all cases are found in people under the age of 45. Around 15% of all lung cancers are small cell type (SCLC), which tend to spread widely through the body, while the remaining 85% are non-small cell (NSCLC). It has been estimated that approximately US$9.6 billion is spent in the USA each year on treating lung cancer.

Lung Cancer Diagnosis

Lung cancer is a life-threatening disease because it often metastasises even before it can be detected on a chest x-ray.

Usually symptoms of lung cancer do not appear until the disease is in an advanced stage. So far, there is no screening test that has been shown to improve a person's chance for a cure. Imaging tests such as a chest x-ray, CT scan, MRI scan or PET scan may be used to detect lung cancer. Tests to confirm the diagnosis are then performed and include sputum cytology, needle biopsy, bronchoscopy, endobronchial ultrasound and complete blood count (CBC).

Lung Cancer Staging

Nearly 60% of people diagnosed with lung cancer die within one year of diagnosis; 75% die within 2 years. The 5-year survival rate for people diagnosed with NSCLC is about 15%; for SCLC the 5-year survival rate is about 6%. NSCLC is staged using the American Joint Committee on Cancer (AJCC) TNM system—Stage 0—Stage IV. The 5-year survival rates by stage are as follows: stage I: 47%; stage II; 26%; stage III: 8% and stage IV: 2%. SCLC has a 2-stage system—limited stage and extensive stage. About two thirds of SCLC patients have extensive disease at diagnosis. If SCLC is found very early and is localised to the lung alone, the 5-year survival rate is around 21%, but only 6% of patients fall into this category. Where the cancer has spread, the 5-year survival is around 11%. For patients with extensive disease, the 5-year survival is just 2%.

Lung Cancer Treatment

Surgery is the only reliable method to cure NSCLC. Types of surgery include lobectomy, pneumonectomy, segmentectomy and video-assisted thoracic surgery (for small tumours). External beam radiation therapy is sometimes used as the primary treatment, especially if the patient's health is too poor to undergo surgery. Radiation therapy can also be used after surgery. Chemotherapy may be given as the primary treatment or as an adjuvant to surgery. Targeted therapy using epidermal growth factor receptor (EGFR) antagonists such as gefitinib or erlotinib can also be given after other treatments have failed. Antiangiogenic drugs, such as bevacizumab, have been found to prolong survival of patients with advanced lung cancer. Photodynamic therapy is also being researched as a treatment for lung cancer.

The main treatment for SCLC is chemotherapy, either alone or in combination with external beam radiation therapy and very rarely, surgery.

Chemotherapeutic agents used for NSCLC and SCLC include cisplatin, carboplatin, mitomycin C, ifosfamide, vinblastine, gemcitabine, etoposide, vinorelbine, paclitaxel, docetaxel and irinotecan.

Melanoma

Cancer of the skin is the most common of all cancers, probably accounting for more than 50% of all cancers. Melanoma accounts for about 4% of skin cancer cases but causes a large majority of skin cancer deaths. Half of all melanomas are found in people under age 57. About 1 of every 30,000 girls aged 15 to 19 will develop melanoma. For boys of this age, the rate is about 1 of every 15,000. In the USA, about 62,000 new melanomas are diagnosed each year, with around 8,000 deaths. The number of new melanomas diagnosed in the United States is increasing. Among white men and women in the United States, incidence rates for renal cell cancer increased sharply at about 6% per year from 1973 until the early 1980s. Since 1981, however, the rate of increase slowed to little less than 3% per year. Since 1973, the mortality rate for renal cell cancer has increased by 50%. More recently, the death rate from melanoma has leveled off for men and dropped slightly in women. The risk of melanoma is about 20 times higher for whites than for African Americans.

Melanoma Diagnosis

Excisional biopsy is the preferred diagnostic method but other types of skin biopsy can also be used including incisional biopsy, shave biopsy and punch biopsy. Metastatic melanoma may not be found until long after the original melanoma was removed from the skin. Metastatic melanoma can be diagnosed using a number of methods including fine needle aspiration biopsy, surgical lymph node biopsy and sentinel lymph node mapping and biopsy. Imaging tests such as a chest x-ray, computed tomography (CT), magnetic resonance imaging (MRI), positron emission tomography (PET) and nuclear bone scans can also be used.

Melanoma Staging

Melanoma is staged using the American Joint Committee on Cancer (AJCC) TNM system—Stage 0—Stage IV. The thickness of the melanoma is measured using the Breslow measurement.

Melanoma Treatment

Thin melanomas can be completely cured by excision. If the melanoma is on a finger or toe, treatment may involve amputation of the digit. If the melanoma has spread to the lymph nodes, lymph node dissection may be required.

No current treatment is usually able to cure stage IV melanoma. Although chemotherapy is usually not as effective in melanoma as in some other types of cancer, it may relieve symptoms or extend survival of some patients with stage IV melanoma. Chemotherapy drugs often used to treat melanoma include dacarbazine, carmustine, cisplatin, vinblastine and temozolomide. Recent studies have found that biochemotherapy, combining several chemotherapy drugs with 1 or more immunotherapy drugs may be more effective than a single chemotherapy drug alone. Immunotherapy drugs include interferon-alpha and/or interleukin-2 Both drugs can help shrink metastatic (stage III and IV) melanomas in about 10% to 20% of patients. Interferon-alpha2b given to patients with stage III melanoma following surgery may delay the recurrence of melanoma. Isolated limb perfusion, using Melphalan, is an experimental type of chemotherapy sometimes used to treat metastatic melanomas confined to the arms or legs. Radiation therapy may be used to treat recurrent melanoma and is used as palliation of metastases to the bone and brain.

A person who has already had melanoma has an increased risk of developing melanoma again. In one study, about 11% of people with melanoma developed a second one within 5 years. And those that developed a second melanoma had a 30% chance of developing a third one in 5 years.

Melanoma Survival by Stage

| Stage | 5-year relative survival rate | 10-year relative survival rate |
|---|---|---|
| 0 | 97% | — |
| I | 90-95% | 80% |
| IIA | 78% | 64% |
| IIB | 63-67% | 51-54% |
| IIC | 45% | 32% |
| IIIA | 63-70% | 57-63% |
| IIIB | 46-53% | 38% |
| IIIC | 28% | 15-25% |
| IV | 18% | 14% |

Osteosarcoma

Osteosarcoma is the most common bone cancer in children, adolescents and young adults (accounting for approximately 5% of childhood tumours) but it is still a rare disease with an annual incidence of 2-3 per million in the general population. There are about 900 new cases of osteosarcoma diagnosed in the United States each year (about 400 of which occur in children and adolescents younger than 20 years old), with approximately 300 deaths each year. Osteosarcoma is a primary malignant tumour of the appendicular skeleton that is characterized by the direct formation of bone or osteoid tissue by the tumour cells. In children and adolescents, more than 50% of these tumours arise from the bones around the knee. Many people with osteosarcoma can be cured but not all and the price of cure even with the most modern treatments is high.

Osteosarcoma Diagnosis

Diagnostic methods for osteosarcoma include an X-ray, bone scan, CT scan, PET scan and MRI of the affected area. A CT scan of the chest is also conducted to see if the cancer has spread to the lungs. Blood tests can be used to detect serum levels of alkaline phosphatase and/or LDH, which are increased in a considerable number of osteosarcoma patients, although serum levels do not correlate reliably with disease extent. The diagnosis of osteosarcoma must be verified histologically with a core needle biopsy or open biopsy. Micrometastatic disease is present at diagnosis in 80-90% of patients but undetectable with any of present tests. Osteosarcoma staging There are two staging systems for osteosarcoma: the Enneking system where low-grade tumours are stage I, high-grade tumours are stage II, and metastatic tumours (regardless of grade) are stage III and the American Joint Commission on Cancer (AJCC) system which stages osteosarcoma from IA to IVB.

There are essentially 2 categories of patients: those who present without clinically detectable metastatic disease (localized osteosarcoma) and the 15-20% of patients who present with clinically detectable metastatic disease (metastatic osteosarcoma). 85% to 90% of metastatic disease is in the lungs.

Osteosarcoma has one of the lowest survival rates for pediatric cancer. The overall 5-year survival rate for patients with non-metastatic osteosarcoma is over 70%. The 5-year survival rate for patients whose cancers have already metastasised at the time of their diagnosis is about 30%.

Osteosarcoma Treatment

Once osteosarcoma has been diagnosed, the correct treatment needs to be selected. Successful treatment generally requires the combination of effective systemic chemotherapy and complete resection (amputation, limb preservation, or rotationplasty) of all clinically detectable disease (including resection of all overt metastatic disease). Protective weight bearing is recommended for patients with tumours of weight-bearing bones to prevent pathological fractures that could preclude limb-preserving surgery.

At least 80% of patients with localized osteosarcoma treated with surgery alone will develop metastatic disease. Randomized clinical trials have established that adjuvant chemotherapy is effective in preventing relapse or recurrence in patients with localized resectable primary tumours. The chemotherapeutic agents used include high-dose methotrexate, doxorubicin, cisplatin, high-dose ifosfamide, etoposide, carboplatin, cyclophosphamide, actinomycin D and bleomycin. Bone-seeking radioactive chemicals are sometimes used to treat osteosarcoma. Samarium-153 may be given in addition to external beam radiation therapy.

There is no difference in overall survival (OS) between patients initially treated by amputation and those treated with a limb-sparing procedure. In general, more than 80% of patients with extremity osteosarcoma can be treated by a limb-sparing operation and do not require amputation. Complications of limb-salvage surgery include infection and grafts or rods that become loose or broken. Limb-salvage surgery patients may need more surgery during the following 5 years, and some may eventually need an amputation. Limb length inequality is also a major potential problem for young children. Treatment options include extensible prostheses, amputation, and rotationplasty for these children.

Most recurrences of osteosarcoma develop within 2 to 3 years after treatment completion. Fewer than 30% of patients with localized resectable primary tumours treated with surgery alone can be expected to survive free of relapse. Recurrence of osteosarcoma is most often in the lung. The ability to achieve a complete resection of recurrent disease is the most important prognostic factor at first relapse, with a 5-year survival rate of 20% to 45% following complete resection of metastatic pulmonary tumours and 20% following complete resection of metastases at other sites. Repeated resections of pulmonary recurrences can lead to extended disease control and possibly cure for some patients. Survival for patients with unresectable metastatic disease is less than 5%. Resection of metastatic disease followed by observation alone results in low overall and disease-free survival.

Ovarian Cancer

Ovarian cancer accounts for about 1.9% of cancer cases globally and around 1.8% of deaths. Global incidence of ovarian cancer is around 205,000, predominantly in post-menopausal women in developed countries, with around 125,000 deaths. About 85% to 90% of ovarian cancers are epithelial ovarian carcinomas. About 5% of ovarian cancers are germ cell tumours and a smaller percentage are stromal tumours. Ovarian cancer is the eighth most common cancer among women. In the USA, about 20,200 new cases of ovarian cancer are diagnosed each year and it accounts for about 3% of all cancers in women. The risk of developing and dying from ovarian cancer is higher for white women than black women. Around two-thirds of women with ovarian cancer are 55 or older. Ovarian cancer ranks fifth in cancer deaths among women in the USA, accounting for more deaths than any other cancer of the female reproductive system. There are around 15,300 deaths in the USA from ovarian cancer each year. It has been estimated that approximately US$2.2 billion is spent in the USA each year on treating ovarian cancer.

Ovarian Cancer Diagnosis

It is currently difficult to diagnose ovarian cancer at an early stage. Imaging tests such as ultrasound, computed tomography and magnetic resonance imaging can confirm whether a pelvic mass is present. Blood tests, including a CA-125 test and a laparoscopy are performed. Ovarian cancer is then confirmed by biopsy.

Ovarian Cancer Staging

Ovarian cancer is staged using the American Joint Committee on Cancer (AJCC) TNM system—stage I-IV. The FIGO (International Federation of Gynecology and Obstetrics) system is also used. Ovarian cancers are also given a grade from 1-3. About 76% of women with ovarian cancer survive 1 year after diagnosis, and 45% survive longer than 5 years after diagnosis. If diagnosed and treated while the cancer has not spread outside the ovary, the 5-year survival rate is 94%. However, only 19% of all ovarian cancers are found at this early stage.

Ovarian Cancer Treatment

Surgery for ovarian cancer includes hysterectomy, bilateral salpingectomy, bilateral oophorectomy and omentectomy. Debulking is performed in women in whom the cancer has spread widely throughout their abdomen.

Intraperitoneal (IP) chemotherapy using a combination therapy using a platinum compound, such as cisplatin or carboplatin, and a taxane, such as paclitaxel or docetaxel, is the standard approach. Tumour recurrence is sometimes treated with additional cycles of a platinum compound and/or a taxane. In other cases, recurrence is treated with other drugs, such as topotecan, anthracyclines such as doxorubicin (Adriamycin) and liposomal doxorubicin (Doxil), gemcitabine, cyclophosphamide, vinorelbine (Navelbine), hexamethylmelamine, ifosfamide, and etoposide. Resistance to currently-available chemotherapeutic agents is a major problem. Although complete clinical response is achieved in 75% of patients after initial treatment, most will develop recurrent disease and require re-treatment.

External beam radiation therapy can also sometimes be used.

Ovarian Cancer Survival by Stage

| Stage | Relative 5-Years Survival Rate |
| --- | --- |
| IA | 92.7% |
| IB | 85.4% |
| IC | 84.7% |
| IIA | 78.6% |
| IIB | 72.4% |
| IIC | 64.4% |
| IIIA | 50.8% |
| IIIB | 42.4% |
| IIIC | 31.5% |
| IV | 17.5% |

Pancreatic Cancer

Pancreatic cancer is a very difficult cancer to detect and the prognosis for patients is usually very poor. The number of new cases and deaths per year is almost equal. Global incidence of pancreatic cancer is approximately 230,000 cases (about 2% of all cancer cases), with about 225,000 deaths (3.4% of cancer deaths) per year. It is much more prevalent in the developed world. In the USA, there are about 34,000 new cases per year, with about 32,000 deaths. It has been estimated that approximately US$1.5 billion is spent in the USA each year on treating pancreatic cancer.

Pancreatic Cancer Diagnosis

Pancreatic cancer is very difficult to detect and very few pancreatic cancers are found early. Patients usually have no symptoms until the cancer has spread to other organs. There are currently no blood tests or easily available screening tests that can accurately detect early cancers of the pancreas. An endoscopic ultrasound followed by a biopsy is the best way to diagnose pancreatic cancer. Other detection methods include CT, CT-guided needle biopsy, PET, ultrasonography and MRI. Blood levels of CA 19-9 and carcinoembryonic antigen (CEA) may be elevated but by the time blood levels are high enough to be detected, the cancer is no longer in its early stages.

Pancreatic Cancer Staging

Pancreatic cancer has four stages, stage I to stage IV according to the American Joint Committee on Cancer (AJCC) TNM system. Pancreatic cancer is also divided into resectable, locally advanced (unresectable) and metastatic cancer. For patients with advanced cancers, the overall survival rate is <1% at 5 years with most patients dying within 1 year.

Pancreatic Cancer Treatment

Surgery is the only method of curing pancreatic cancer. About 10% of pancreatic cancers are contained entirely within the pancreas at the time of diagnosis and attempts to remove the entire cancer by surgery may be successful in some of these patients. The 5-year survival for those undergoing surgery with the intent of completely removing the cancer is about 20%. Potentially curative surgery, usually by pancreaticoduodenectomy (Whipple procedure), is used when it may be possible to remove all of the cancer. Palliative surgery may be performed if the tumour is too widespread to be completely removed. Removing only part of the cancer does not allow patients to live longer. Pancreatic cancer surgery is difficult to perform with a high likelihood of complications.

External beam radiation therapy combined with chemotherapy can be given before or after surgery and can also be given to patients whose tumours are too widespread to be removed by surgery. The main chemotherapeutic agents which are used are gemcitabine and 5-fluorouracil. Targeted therapy using drugs such as erlotinib and cetuximab may be of benefit to patients with advanced pancreatic cancer.

Prostate Cancer

Prostate cancer is the third most common cancer in the world amongst men and it accounts for 5.4% of all cancer cases globally and 3.3% of cancer-related deaths. Global incidence of prostate cancer is around 680,000 cases, with about 221,000 deaths. In the USA, prostate cancer is the most common cancer, other than skin cancers, in American men. About 234,460 new cases of prostate cancer are diagnosed in the USA each year. About 1 man in 6 will be diagnosed with prostate cancer during his lifetime, but only 1 in 34 will die of it. A little over 1.8 million men in the USA are survivors of prostate cancer. The risk of developing prostate cancer rises significantly with age and 60% of cases occur in men over the age of 70. Prostate cancer is the second leading cause of cancer death in American men. Around 27,350 men in the USA die of prostate cancer each year. Prostate cancer accounts for about 10% of cancer-related deaths in men. Modern methods of detection and treatment mean that prostate cancers are now found earlier and treated more effectively. This has led to a yearly drop in death rates of about 3.5% in recent years. Prostate cancer is most common in North America and northwestern Europe. It is less common in Asia, Africa, Central America, and South America. It has been estimated that approximately US$8.0 billion is spent in the USA each year on treating prostate cancer.

Prostate Cancer Diagnosis

Prostate cancer can often be found early by testing the amount of prostate-specific antigen (PSA) in the blood. A digital rectal exam (DRE) can also be performed. However, there are potential problems with the current screening methods. Neither the PSA test nor the DRE is 100% accurate. A core needle biopsy is the main method used to diagnose prostate cancer. A transrectal ultrasound (TRUS) may be used during a prostate biopsy.

Prostate Cancer Staging

Prostate cancers are graded according to the Gleason system, graded from 1-5, which results in the Gleason score, from 1-10. Prostate cancer is staged using the American Joint Committee on Cancer (AJCC) TNM system and combined with the Gleason score to give stages from I-IV.

Ninety one percent of all prostate cancers are found in the local and regional stages; the 5-year relative survival rate for these men is nearly 100%. The 5-year relative survival rate for men whose prostate cancers have already spread to distant parts of the body at the time of diagnosis is about 34%.

Prostate Cancer Treatment

Because prostate cancer often grows very slowly, some men never have treatment and expectant management is recommended. If treatment is required and the cancer is not thought to have spread outside of the gland, a radical prostatectomy can be performed. Transurethral resection of the prostate (TURP) can be performed to relieve symptoms but not to cure prostate cancer.

External beam radiation therapy (three-dimensional conformal radiation therapy (3DCRT), intensity modulated radiation therapy (IMRT) or conformal proton beam radiation therapy) or brachytherapy can also be used as treatment.

Cryosurgery is sometimes used to treat localized prostate cancer but as not much is known about the long-term effectiveness of cryosurgery, it is not routinely used as a first treatment for prostate cancer. It can be used for recurrent cancer after other treatments.

Androgen deprivation therapy (ADT) (orchiectomy or luteinizing hormone-releasing hormone (LHRH) analogs or antagonists) can be used to shrink prostate cancers or make them grow more slowly.

Chemotherapy is sometimes used if prostate cancer has spread outside of the prostate gland and is hormone therapy resistant. Chemotherapeutic agents include docetaxel, prednisone, doxorubicin, etoposide, vinblastine, paclitaxel, carboplatin, estramustine, vinorelbine. Like hormone therapy, chemotherapy is unlikely to result in a cure.

Renal Cell Cancer

The incidence of kidney cancer is much higher in developed countries, being the sixth most common form of cancer in Western Europe. Kidney cancer accounts for about 1.9% of cancer cases globally and 1.5% of deaths. Global incidence of kidney cancer is around 208,000 cases, with over 100,000 deaths. Around 38,900 new cases of kidney cancer are diagnosed in the USA each year, with around 12,800 deaths. It is very uncommon under age 45, and its incidence is highest between the ages of 55 and 84. The rate of people developing kidney cancer has been increasing at about 1.5% per year but the death rate has not been increasing. Renal cell carcinoma accounts for more than 90% of malignant kidney tumours. It has been estimated that approximately US$1.9 billion is spent in the USA each year on treating kidney cancer.

Renal Cell Cancer Diagnosis

Many renal cell cancers are found at a late stage; they can become quite large without causing any pain or discomfort. Because the kidney is deep inside the body, small renal cell tumours cannot be seen or felt during a physical exam. There are no simple tests that can detect renal cell cancer early. About 25% of patients with renal cell carcinoma will already have metastatic spread of their cancer when they are diagnosed. Imaging tests such as computed tomography (CT) scans and magnetic resonance imaging (MRI) can find small renal cell carcinomas. However, these imaging tests are relatively expensive and cannot always distinguish benign tumours from small renal cell carcinomas.

Renal cell cancer can often be diagnosed without the need for a biopsy using a CT scan, MRI, ultrasound, positron emission tomography (PET) scan, intravenous pyelogram (IVP) and/or angiography. Fine needle aspiration biopsy may however be valuable when imaging results are not conclusive enough to warrant removing a kidney.

Renal Cell Cancer Staging

Renal cell cancers are usually graded on a scale of 1-4. Renal cell cancer is also staged using the American Joint Committee on Cancer (AJCC) TNM system—stage I-IV. The University of California Los Angeles Integrated Staging System can also be used, which divides patients without any tumour spread into three groups—low risk, intermediate risk and high risk. The 5-year cancer-specific survival for the low-risk group is 91%, for the intermediate-risk group is 80%, and for the high-risk group is 55%. Patients with tumour spread are also divided into three groups—low, intermediate and high risk. The 5-year cancer-specific survival for the low-risk group is 32%, for the intermediate-risk group 20% and for the high-risk group 0%.

Renal Cell Cancer Treatment

Surgery by radical nephrectomy (and sometimes regional lymphadenectomy), partial nephrectomy or laparoscopic nephrectomy is the main treatment for renal cell carcinoma. External beam radiation therapy is sometimes used as the main treatment for renal cell cancer if a person's general health is too poor to undergo surgery. Radiation therapy can also be used to palliate symptoms of renal cell cancer. Unfortunately, renal cell carcinomas are not very sensitive to radiation. Using radiation therapy before or after removing the cancer is not routinely recommended because studies have shown no improvement in survival rates.

Renal cell cancers are very resistant to present forms of chemotherapy, and there is no standard way to treat it with drugs. Some drugs, such as vinblastine, floxuridine, and 5-fluorouracil (5-FU) are mildly effective. A combination of 5-FU and gemcitabine has benefited some patients. A 5-FU-like drug, capecitabine, may also have some benefit.

Cytokines (interleukin-2 (IL-2) and interferon-alpha) have become one of the standard treatments for metastatic renal cell carcinoma. These cause the cancers to shrink to less than half their original size in about 10% to 20% of patients. Patients who respond to IL-2 tend to have lasting responses. Recent research with a combination of IL-2, interferon, and chemotherapy (using 5-fluorouracil) is also promising and may offer a better chance of partial or complete remission. Cytokine therapy does have severe side affects however.

Sorafenib (Nexavar) has been shown to slow the progression of the cancer in patients with advanced disease. It acts by blocking both angiogenesis and growth-stimulating molecules in the cancer cell. Sunitinib (Sutent) is another drug that attacks both blood vessel growth and other targets that stimulate cancer cell growth. Promising results have also been seen in studies of this drug with tumours shrinking in about one-third of patients and tumours staying about the same size in another third. Bevacizumab (Avastin) is an angiogenesis inhibitor. This drug is already approved for use against other cancer types and recent studies have shown it may also be effective against renal cell cancer.

Renal Cell Cancer Survival by Stage

| T stage cancer | 5/10-year cancer-specific survival |
| --- | --- |
| T1 | 95%/91% |
| T2 | 80%/70% |
| T3a | 66%/53% |
| T3b | 52%/43% |
| T3c | 43%/42% |

Therapeutic Challenges

The major challenges in treatment of the above mentioned cancers are to improve early detection rates, to find new non-invasive markers that can be used to follow disease progression and identify relapse, and to find improved and less toxic therapies, especially for more advanced disease where 5 year survival is still poor. There is a great need to identify targets which are more specific to the cancer cells, e.g. ones which are expressed on the surface of the tumour cells so that they can be attacked by promising new approaches like immunotherapeutics and targeted toxins.

SUMMARY OF THE INVENTION

The present invention provides, inter alia, the following:
1. An isolated polypeptide which (a) comprises or consists of the amino acid sequence of SEQ ID NO: 1, SEQ ID NO: 2, SEQ ID NO: 3, SEQ ID NO: 4 or SEQ ID NO: 5 or (b) is a derivative having one or more amino acid substitutions, modifications, deletions or insertions relative to the amino acid sequence of SEQ ID NO: 1, SEQ ID NO: 2, SEQ ID NO: 3, SEQ ID NO: 4 or SEQ ID NO: 5 which retains the activity of the relative protein.
2. An isolated OGTA014, OGTA020, OGTA067, OGTA116 or OGTA194 polypeptide which comprises or consists of the amino acid sequence of SEQ ID NO: 1, SEQ ID NO: 2, SEQ ID NO: 3, SEQ ID NO: 4 or SEQ ID NO: 5 or an amino acid sequence having at least 75% identity (eg at least 80, 90 or 95% identity) with any one of said sequences over the entire length thereof to the polypeptide according to (1) over the entire length thereof.
3. An isolated nucleic acid molecule encoding a polypeptide of (1) or (2) eg an isolated nucleic acid molecule which (a) comprises or consists of the DNA sequence of SEQ ID NO: 86, SEQ ID NO: 87, SEQ ID NO: 88, SEQ ID NO: 89 or SEQ ID NO: 90 or its RNA equivalent; (b) has a sequence which is complementary to the sequences of a); (c) has a sequence which codes for a polypeptide as defined in 1 or 2; (d) has a sequence which shows substantial identity with any of those of a), b) and c); or (e) is a fragment of a), b), c) or d), which is at least 10 nucleotides in length.
4. An expression system comprising a nucleic acid capable of producing a polypeptide according to (1) or (2), when said expression system is present in a compatible host cell.
5. A method for producing a polypeptide comprising transfecting or transforming a cell with the expression system of (4), such that the host cell, under appropriate culture conditions, produces a polypeptide as defined in (1) or (2).
6. A recombinant host cell comprising the expression system of (4).

The term "polypeptides" includes peptides, polypeptides and proteins. These are used interchangeably unless otherwise specified.

Also provided are methods and compositions for screening, diagnosis, prognosis and therapy of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer (referred to herein as a relevant cancer), for B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer patients' stratification, for monitoring the effectiveness of a relevant cancer treatment, and for drug development for treatment of a relevant cancer.

We have used mass spectrometry to identify peptides generated by gel electrophoresis or tagging with iTRAQ reagents and tryptic digest of membrane proteins extracted from lymphoid, breast, colorectal, gastric, liver, lung, skin, osteoblast, ovarian, pancreatic, prostate and kidney cancer tissue samples. Peptide sequences were compared to existing protein and cDNA databases and the corresponding gene sequences identified. The proteins of the invention have not been previously reported to originate from lymphocytic, breast, colorectal, gastric, liver, lung, skin, osteoblast, ovarian, pancreatic, prostate or kidney cancer cell membranes and represent proteins of new diagnostic and therapeutic value.

A first aspect of the invention provides methods of treating B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer, comprising administering to a patient a therapeutically effective amount of a compound that modulates (e.g., upregulates or downregulates) or complements the expression or the biological activity (or both) of one or more of the proteins of the invention in patients having a relevant cancer, in order to (a) prevent the onset or development of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer; (b) prevent the progression of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer; or (c) ameliorate the symptoms of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer.

According to a second aspect of the invention we provide a method of detecting, diagnosing and/or screening for or monitoring the progression of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer or of monitoring the effect of an anti-B-cell non-Hodgkin's lymphoma, anti-breast cancer, anti-colorectal cancer, anti-gastric cancer, anti-hepatocellular carcinoma, anti-lung cancer, anti-lymphoid leukaemia (particularly acute T-cell leukaemia), anti-melanoma, anti-osteosarcoma, anti-ovarian cancer, anti-pancreatic cancer, anti-prostate cancer or anti-renal cell cancer drug or therapy in a subject which comprises detecting the presence or level of the proteins of the invention, or one or more fragments thereof, or the presence or level of nucleic acid encoding the proteins of the invention or the presence or level of the activity of the proteins of the invention or which comprises detecting a change in the level thereof in said subject.

According to a third aspect of the invention we provide a method of detecting, diagnosing and/or screening for B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer in a candidate subject which comprises detecting the presence of the proteins of the invention, or one or more fragments thereof, or the presence of nucleic acid encoding the proteins of the invention or the presence of the activity of the proteins of the invention in said candidate subject, in which either (a) the presence of an elevated level of the proteins of the invention or said one or more fragments thereof or an elevated level of nucleic acid encoding the proteins of the invention or the presence of an elevated level of the activity of the proteins of the invention in the candidate subject as compared with the level in a healthy subject or (b) the presence of a detectable level of the proteins of the invention or said one or more fragments thereof or a detectable level of nucleic acid encoding the proteins of the invention or the presence of a detectable level of the activity of the proteins of the invention in the candidate subject as compared with a corresponding undetectable level in a healthy subject indicates the presence of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer in said subject.

According to a fourth aspect of the invention we provide a method of monitoring the progression of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer in a subject or of monitoring the effect of an anti-B-cell non-Hodgkin's lymphoma, anti-breast cancer, anti-colorectal cancer, anti-gastric cancer, anti-hepatocellular carcinoma, anti-lung cancer, anti-lymphoid leukaemia (particularly acute T-cell leukaemia), anti-melanoma, anti-osteosarcoma, anti-ovarian cancer, anti-pancreatic cancer, anti-prostate cancer or anti-renal cell cancer drug or therapy which comprises detecting the presence of the proteins of the invention, or one or more fragments thereof, or the presence of nucleic acid encoding the proteins of the invention or the presence of the activity of the proteins of the invention in said candidate subject at a first time point and at a later time point, the presence of an elevated or lowered level of the proteins of the invention or said one or more fragments thereof or an elevated or lowered level of nucleic acid encoding the proteins of the invention or the presence of an elevated or lowered level of the activity of the proteins of the invention in the subject at the later time point as compared with the level in the subject at said first time point, indicating the progression or regression of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer or indicating the effect or non-effect of an anti-B-cell non-Hodgkin's lymphoma, anti-breast cancer, anti-colorectal cancer, anti-gastric cancer, anti-hepatocellular carcinoma, anti-lung cancer, anti-lymphoid leukaemia (particularly acute T-cell leukaemia), anti-melanoma, anti-osteosarcoma, anti-ovarian cancer, anti-pancreatic cancer, anti-prostate cancer or anti-renal cell cancer drug or therapy in said subject.

The presence of the proteins of the invention, or one or more fragments thereof, or the presence of nucleic acid encoding the proteins of the invention or the presence of the activity of the proteins of the invention may, for example, be detected by analysis of a biological sample obtained from said subject.

The method of invention may typically include the step of obtaining a biological sample for analysis from said subject. In one or more aspects the methods of the invention do not include the step of obtaining the sample from a patient/subject.

The biological sample used can be from any source such as a serum sample or a tissue sample, e.g. lymphoid, breast, colorectal, gastric, liver, lung, skin, osteoblast, ovarian, pancreatic, prostate or kidney tissue. For instance, when looking for evidence of metastatic breast cancer, colorectal cancer, gastric cancer, hepatocellular carcinoma, lung cancer, melanoma, osteosarcoma, ovarian cancer, pancreatic cancer, prostate cancer and renal cell cancer, one would look at major sites of breast cancer, colorectal cancer, gastric cancer, hepatocellular carcinoma, lung cancer, melanoma, osteosarcoma, ovarian cancer, pancreatic cancer, prostate cancer and renal cell cancer metastasis, e.g. the liver, the lungs and bones for breast cancer; the liver, the peritoneal cavity, the pelvis, the retroperitoneum and the lungs for colorectal cancer; the liver, the lungs, the brain and bones for gastric cancer; the lungs and bones for hepatocellular carcinoma; the brain, the liver, the bones and adrenal glands for lung cancer; the lungs, the brain and bones for melanoma; the lungs and other bones for osteosarcoma; the abdomen for ovarian cancer; the liver for pancreatic cancer; the bladder, the rectum and bones for prostate cancer and the lungs, the liver and bones for renal cell cancer.

Alternatively the presence of the proteins of the invention, or one or more fragments thereof, or the presence of nucleic acid encoding the proteins of the invention or the presence of the activity of the proteins of the invention may be detected by analysis in situ.

In certain embodiments, methods of diagnosis described herein may be at least partly, or wholly, performed in vitro.

Suitably the presence of the proteins of the invention, or one or more fragments thereof, or the presence of nucleic acid encoding the proteins of the invention or the presence of the activity of the proteins of the invention is detected quantitatively.

For example, quantitatively detecting may comprise:
(a) contacting a biological sample with an affinity reagent that is specific for the proteins of the invention, said affinity reagent optionally being conjugated to a detectable label; and
(b) detecting whether binding has occurred between the affinity reagent and at least one species in the sample, said detection being performed either directly or indirectly.

Alternatively the presence of the proteins of the invention, or one or more fragments thereof, or the presence of nucleic acid encoding the proteins of the invention or the presence of the activity of the proteins of the invention may be detected quantitatively by means involving use of an imaging technology.

In another embodiment, the method of the invention involves use of immunohistochemistry on tissue sections in order to determine the presence of the proteins of the invention, or one or more fragments thereof, or the presence of nucleic acid encoding the proteins of the invention or the presence of the activity of the proteins of the invention, and thereby to localise B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer cells.

In one embodiment the presence of the proteins of the invention or one or more epitope-containing fragments thereof is detected, for example using an affinity reagent capable of specific binding to the proteins of the invention or one or more fragments thereof, such as an antibody.

In another embodiment the activity of the proteins of the invention is detected.

According to another aspect of the invention there is provided a method of detecting, diagnosing and/or screening for or monitoring the progression of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer or of monitoring the effect of an anti-B-cell non-Hodgkin's lymphoma, anti-breast cancer, anti-colorectal cancer, anti-gastric cancer, anti-hepatocellular carcinoma, anti-lung cancer, anti-lymphoid leukaemia (particularly acute T-cell leukaemia), anti-melanoma, anti-osteosarcoma, anti-ovarian cancer, anti-pancreatic cancer, anti-prostate cancer or anti-renal cell cancer drug or therapy in a subject which comprises detecting the presence or level of antibodies capable of immunospecific binding to the proteins of the invention, or one or more epitope-containing fragments thereof or which comprises detecting a change in the level thereof in said subject.

According to another aspect of the invention there is also provided a method of detecting, diagnosing and/or screening for B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer in a subject which comprises detecting the presence of antibodies capable of immunospecific binding to the proteins of the invention, or one or more epitope-containing fragments thereof in said subject, in which (a) the presence of an elevated level of antibodies capable of immunospecific binding to the proteins of the invention or said one or more epitope-containing fragments thereof in said subject as compared with the level in a healthy subject or (b) the presence of a detectable level of antibodies capable of immunospecific binding to the proteins of the invention or said one or more epitope-containing fragments thereof in said subject as compared with a corresponding undetectable level in a healthy subject indicates the presence of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer in said subject.

One particular method of detecting, diagnosing and/or screening for B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer comprises:

(a) bringing into contact with a biological sample to be tested the proteins of the invention, or one or more epitope-containing fragments thereof; and
(b) detecting the presence of antibodies in the subject capable of immunospecific binding to the proteins of the invention, or one or more epitope-containing fragments thereof According to another aspect of the invention there is provided a method of monitoring the progression of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer or of monitoring the effect of an anti-B-cell non-Hodgkin's lymphoma, anti-breast cancer, anti-colorectal cancer, anti-gastric cancer, anti-hepatocellular carcinoma, anti-lung cancer, anti-lymphoid leukaemia (particularly acute T-cell leukaemia), anti-melanoma, anti-osteosarcoma, anti-ovarian cancer, anti-pancreatic cancer, anti-prostate cancer or anti-renal cell cancer drug or therapy in a subject which comprises detecting the presence of antibodies capable of immunospecific binding to the proteins of the invention, or one or more epitope-containing fragments thereof in said subject at a first time point and at a later time point, the presence of an elevated or lowered level of antibodies capable of immunospecific binding to the proteins of the invention, or one or more epitope-containing fragments thereof in said subject at the later time point as compared with the level in said subject at said first time point, indicating the progression or regression of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer or the effect or non-effect of an anti-B-cell non-Hodgkin's lymphoma, anti-breast cancer, anti-colorectal cancer, anti-gastric cancer, anti-hepatocellular carcinoma, anti-lung cancer, anti-lymphoid leukaemia (particularly acute T-cell leukaemia), anti-melanoma, anti-osteosarcoma, anti-ovarian cancer, anti-pancreatic cancer, anti-prostate cancer or anti-renal cell cancer drug or therapy in said subject.

The presence of antibodies capable of immunospecific binding to the proteins of the invention, or one or more epitope-containing fragments thereof is typically detected by analysis of a biological sample obtained from said subject (exemplary biological samples are mentioned above, e.g. the sample is a sample of lymphoid, breast, colorectal, gastric, liver, lung, skin, osteoblast, ovarian, pancreatic, prostate or kidney tissue, or else a sample of blood or saliva).

The method typically includes the step of obtaining said biological sample for analysis from said subject.

The antibodies that may be detected include IgA, IgM and IgG antibodies.

In any of the above methods, the level that may be detected in the candidate subject who has B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer is 2 or more fold higher than the level in the healthy subject.

Another aspect of the invention is agents capable of specific binding to the proteins of the invention, or a fragment thereof, or hybridizing agents capable of hybridizing to nucleic acid encoding the proteins of the invention or agents capable of detecting the activity of the proteins of the invention for use in screening for, detecting and/or diagnosing disease, such as cancer, and especially B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer.

Another aspect of the invention is the proteins of the invention, or fragments thereof for use in screening for, detecting and/or diagnosing disease such as cancer, and especially B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer.

Another aspect of the invention is affinity reagents capable of specific binding to the proteins of the invention or fragments thereof, for example affinity reagents which contain or are conjugated to a detectable label or contain or are conjugated to a therapeutic moiety such as a cytotoxic moiety. The affinity reagent may, for example, be an antibody.

Another aspect of the invention is hybridizing agents capable of hybridizing to nucleic acid encoding the proteins of the invention, for example, hybridizing agents which contain or are conjugated to a detectable label. One example of a hybridizing agent is an inhibitory RNA (RNAi). Other examples include anti-sense oligonucleotides and ribozymes.

The invention also provides kits containing the proteins of the invention and/or one or more fragments thereof or containing one or more aforementioned affinity reagents and/or hybridizing agents or containing one or more agents capable of detecting the activity of the proteins of the invention together with instructions for their use in an aforementioned method. The kit may further contain reagents capable of detecting and reporting the binding of said affinity reagents and/or hybridizing agents to their binding partners.

Another aspect of the invention is pharmaceutical compositions comprising a therapeutically effective amount of affinity reagents capable of specific binding to the proteins of the invention or fragments thereof.

Another aspect of the invention is a pharmaceutically acceptable diluent or carrier and a pharmaceutical composition comprising one or more affinity reagents or hybridizing reagents as aforesaid and a pharmaceutically acceptable diluent or carrier.

In one embodiment the cancer to be detected, prevented or treated is B-cell non-Hodgkin's lymphoma.

In another embodiment the cancer to be detected, prevented or treated is breast cancer.

In another embodiment the cancer to be detected, prevented or treated is colorectal cancer.

In another embodiment the cancer to be detected, prevented or treated is gastric cancer.

In another embodiment the cancer to be detected, prevented or treated is hepatocellular carcinoma.

In another embodiment the cancer to be detected, prevented or treated is lung cancer.

In another embodiment the cancer to be detected, prevented or treated is lymphoid leukaemia (particularly acute T-cell leukaemia).

In another embodiment the cancer to be detected, prevented or treated is melanoma.

In another embodiment the cancer to be detected, prevented or treated is osteosarcoma.

In another embodiment the cancer to be detected, prevented or treated is ovarian cancer.

In another embodiment the cancer to be detected, prevented or treated is pancreatic cancer.

In another embodiment the cancer to be detected, prevented or treated is prostate cancer.

In another embodiment the cancer to be detected, prevented or treated is renal cell cancer.

Other aspects of the present invention are set out below and in the claims herein.

BRIEF DESCRIPTION OF THE FIGURES

FIG. 1 shows the amino acid sequences of the proteins of the invention. The tryptics detected experimentally by mass spectrometry are highlighted—mass match peptides are shown in bold, tandem peptides are underlined. The corresponding DNA sequences are also shown.

DETAILED DESCRIPTION OF THE INVENTION

The invention described in detail below provides methods and compositions for clinical screening, diagnosis and prognosis of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer in a mammalian subject for identifying patients most likely to respond to a particular therapeutic treatment, for monitoring the results of a relevant cancer therapy, for drug screening and drug development. The invention also encompasses the administration of therapeutic compositions to a mammalian subject to treat or prevent a relevant cancer. The mammalian subject may be a non-human mammal, for example a human, such as a human adult, i.e. a human subject at least 21 (more preferably at least 35, at least 50, at least 60, at least 70, or at least 80) years old. For clarity of disclosure, and not by way of limitation, the invention will be described with respect to the analysis of lymphoid, breast, colorectal, gastric, liver, lung, skin, osteoblast, ovarian, pancreatic, prostate and kidney tissue. However, as one skilled in the art will appreciate, the assays and techniques described below can be applied to other types of patient samples, including body fluids (e.g. blood, urine or saliva), a tissue sample from a patient at risk of having B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer (e.g. a biopsy such as a bone marrow, breast, liver, stomach, lung, skin, bone, ovarian, pancreatic, prostate or kidney biopsy) or homogenate thereof. The methods and compositions of the present invention are specially suited for screening, diagnosis and prognosis of a living subject, but may also be used for postmortem diagnosis in a subject, for example, to identify family members at risk of developing the same disease.

In one aspect the invention provides an isolated OGTA014, OGTA020, OGTA067, OGTA116 or OGTA194 polypeptide which:

(a) comprises or consists of the amino acid sequence of SEQ ID NO: 1, SEQ ID NO: 2, SEQ ID NO: 3, SEQ ID NO: 4 or SEQ ID NO: 5 ; or (b) is a derivative having one or more amino acid substitutions, modifications, deletions or insertions relative to the amino acid sequence of SEQ ID NO: 1, SEQ ID NO: 2, SEQ ID NO: 3, SEQ ID NO: 4 or SEQ ID NO: 5 which retains the activity of the OGTA014, OGTA020, OGTA067, OGTA116 or OGTA194 protein.

The invention further extends to compositions comprising an isolated protein of the invention, such as a pharmaceutical or immunogenic composition comprising same, in particular a vaccine composition comprising a relevant adjuvants. The invention also extends to kits comprising the components of one or more of these aspects, for example wherein the polypeptide is provided in a lyophilized form for later reconstitution. The invention, in particular, relates to use of any of the aforementioned for treatment or prophylaxis, such as treatment or prophylaxis of cancer, especially a relevant cancer described herein. The invention also extends to use of elements described in this paragraph for the manufacture of a medicament for the treatment or prophylaxis of cancer, such as a relevant cancer described herein and methods of treatment employing the same.

In a further aspect the invention provides an antibody or affinity reagent specific to a polypeptide/protein according to the invention. It further relates to compositions, for example pharmaceutical compositions such as vaccines or parenteral formulations comprising at least one antibody/affinity reagent. The invention also extends to kits comprising the components of one or more of these aspects, for example wherein the antibody or affinity reagent is provided in a lyophilized form for later reconstitution. The invention also extends to any of the aforementioned aspects for use in treatment or prophylaxis, for example in the treatment or prophylaxis of cancer, such as a relevant cancer described herein, or in the manufacture of a medicament for the treatment or prophylaxis of cancer, in particular a relevant cancer as described herein and methods of treatment employing same.

A relevant cancer as used herein refers to B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and/or renal cell cancer.

Proteins of the Invention

In one aspect of the invention, one-dimensional electrophoresis or isobaric tags for relative and absolute quantification (iTRAQ) or other appropriate methods are used to analyze B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer tissue samples from a subject, preferably a living subject, in order to measure the expression of the proteins of the invention for screening or diagnosis of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer, to determine the prognosis of a B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer patient, to monitor the effectiveness of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer therapy, or for drug development.

As used herein, the terms "OGTA(s)", "OGTA according to the invention", "OGTA employed in the invention" or "Proteins of the invention" relates to "OGTA014, OGTA020, OGTA067, OGTA116 and OGTA194", as illustrated in FIG. 1 detected experimentally by 1D gel electrophoresis and iTRAQ analysis of lymphoid, breast, colorectal, gastric, liver, lung, skin, osteoblast, ovarian, pancreatic, prostate and kidney tissue samples. These terms are used interchangeably in this specification.

OGTA014 has been identified in membrane protein extracts of lymphocytic, breast, colorectal, liver, lung, skin, bone, ovarian, pancreatic and kidney tissue samples from B-cell non-Hodgkin's lymphoma, breast cancer, colorectal cancer, hepatocellular carcinoma, lung cancer, lymphoid leukaemia (particularly acute T-cell leukaemia), melanoma, osteosarcoma, ovarian cancer, pancreatic cancer and renal cell cancer patients, through the methods and apparatus of the Preferred Technologies (1D gel electrophoresis or iTRAQ together with tryptic digest of membrane protein extracts). Peptide sequences were compared to the SWISS-PROT and trEMBL databases (held by the Swiss Institute of Bioinformatics (SIB) and the European Bioinformatics Institute (EBI) which are available at www.expasy.com/), and the sequence was found to be analogous to the following entry: Q01650, Large neutral amino acids transporter small subunit 1.

Large neutral amino acids transporter small subunit 1 is known to be expressed abundantly in adult lung and liver, and is also expressed in brain, thymus, retina and some other tissues. Its function is sodium-independent, high-affinity transport of large neutral amino acids. It is involved in cellular amino acid uptake.

OGTA020 has been identified in membrane protein extracts of colorectal, liver, lung, skin, pancreatic and kidney tissue samples from colorectal cancer, hepatocellular carcinoma, lung cancer, melanoma, pancreatic cancer and renal cell cancer patients, through the methods and apparatus of the Preferred Technologies (1D gel electrophoresis or iTRAQ together with tryptic digest of membrane protein extracts). Peptide sequences were compared to the SWISS-PROT and trEMBL databases (held by the Swiss Institute of Bioinformatics (SIB) and the European Bioinformatics Institute (EBI) which are available at www.expasy.com), and the sequence was found to be analogous to the following entry: P42892, Endothelin-converting enzyme 1.

Endothelin-converting enzyme 1 is known to be predominantly expressed in the umbilical vein endothelial cells, polynuclear neutrophils, fibroblasts, atrium cardiomyocytes and ventricles. It is also expressed in placenta, lung, heart, adrenal gland, phaeochromocytoma, liver, testis, small intestine, endothelial cells, umbilical vein smooth muscle cells, saphenous vein cells and kidney. It converts big endothelin-1 to endothelin-1.

OGTA067 has been identified in membrane protein extracts of colorectal, kidney and ovarian tissue samples from colorectal cancer, kidney cancer and ovarian cancer patients, through the methods and apparatus of the Preferred Technologies (1D gel electrophoresis or iTRAQ together with tryptic digest of membrane protein extracts). Peptide sequences were compared to the SWISS-PROT and trEMBL databases (held by the Swiss Institute of Bioinformatics (SIB) and the European Bioinformatics Institute (EBI) which are available at www.expasy.com), and the sequence was found to be analogous to the following entry: Q9UN66, Protocadherin beta 8.

Protocadherin beta 8 is a potential calcium-dependent cell-adhesion protein. It may be involved in the establishment and maintenance of specific neuronal connections in the brain.

OGTA116 has been identified in membrane protein extracts of stomach, liver, pancreatic tissue samples from gastric cancer, hepatocellular carcinoma and pancreatic cancer patients, through the methods and apparatus of the Preferred Technologies (1D gel electrophoresis or iTRAQ together with tryptic digest of membrane protein extracts). Peptide sequences were compared to the SWISS-PROT and trEMBL databases (held by the Swiss Institute of Bioinformatics (SIB) and the European Bioinformatics Institute (EBI) which are available at www.expasy.com), and the sequence was found to be analogous to the following entry: P30825, High-affinity cationic amino acid transporter 1.

High-affinity cationic amino acid transporter 1 is known to be ubiquitously expressed. It is a high-affinity, low capacity permease involved in the transport of the cationic amino acids (arginine, lysine and ornithine) in non-hepatic tissues. It may also function as an ecotropic retroviral leukaemia receptor.

OGTA194 has been identified in membrane protein extracts of lymphoid, breast, colorectal, liver, lung, skin, ovarian, pancreatic, prostate and kidney tissue samples from B-cell non-Hodgkin's lymphoma, breast cancer, colorectal cancer, hepatocellular carcinoma, lung cancer, melanoma, ovarian cancer, pancreatic cancer, prostate cancer and renal cell cancer patients, through the methods and apparatus of the Preferred Technologies (1D gel electrophoresis or iTRAQ together with tryptic digest of membrane protein extracts). Peptide sequences were compared to the SWISS-PROT and trEMBL databases (held by the Swiss Institute of Bioinformatics (SIB) and the European Bioinformatics Institute (EBI)

which are available at www.expasy.com), and the sequence was found to be analogous to the following entry: Q8WTVO, Scavenger receptor class B member 1.

Scavenger receptor class B member 1 is known to be widely expressed. It is a receptor for different ligands such as phospholipids, cholesterol ester, lipoproteins, phosphatidylserine and apoptotic cells. It is a probable receptor for HDL, located in a particular region of the plasma membrane, called caveolae. It facilitates the flux of free and esterified cholesterol between the cell surface and extracellular donors and acceptors, such as HDL and to a lesser extent, apoB-containing lipoproteins and modified lipoproteins. It is probably involved in the phagocytosis of apoptotic cells, via its phosphatidylserine binding activity. It is a receptor for hepatitis C virus glycoprotein E2. Binding between SCARB1 and E2 is independent of the genotype of the viral isolate.

Proteins of the invention are useful as are fragments particularly epitope containing fragments e.g. antigenic or immunogenic fragments thereof and derivatives thereof. Epitope containing fragments including antigenic or immunogenic fragments will typically be of length 12 amino acids or more e.g. 20 amino acids or more e.g. 50 or 100 amino acids or more. Fragments may be 95% or more of the length of the full protein e.g. 90% or more e.g. 75% or 50% or 25% or 10% or more of the length of the full protein.

Epitope containing fragments including antigenic or immunogenic fragments will be capable of eliciting a relevant immune response in a patient. DNA encoding Proteins of the invention is also useful as are fragments thereof eg DNA encoding fragments of Proteins of the invention such as immunogenic fragments thereof. Fragments of nucleic acid (e.g. DNA) encoding Proteins of the invention may be 95% or more of the length of the full coding region e.g. 90% or more e.g. 75% or 50% or 25% or 10% or more of the length of the full coding region. Fragments of nucleic acid (e.g. DNA) may be 36 nucleotides or more e.g. 60 nucleotides or more e.g. 150 or 300 nucleotides or more in length.

Derivatives of the proteins of the invention include variants on the sequence in which one or more (e.g. 1-20 such as 15 amino acids, or up to 20% such as up to 10% or 5% or 1% by number of amino acids based on the total length of the protein) deletions, insertions or substitutions have been made. Substitutions may typically be conservative substitutions. Derivatives of the proteins of the invention include variants on the sequence which have a sequence identity over the entire length thereof of typically at least 60%, 70%, 75%, 80%, 90 or 95%. Derivatives will typically have essentially the same biological function as the protein from which they are derived. Derivatives will typically be comparably antigenic or immunogenic to the protein from which they are derived. Derivatives will typically have either the ligand-binding activity, or the active receptor-complex forming ability, or preferably both, of the protein from which they are derived.

Tables 1-5 below illustrate the different occurrences of OGTA014, OGTA020, OGTA067, OGTA116 and OGTA194 as detected by mass spectrometry of membrane protein extracts of lymphoid, breast, colorectal, gastric, liver, lung, skin, osteoblast, ovarian, pancreatic, prostate and kidney tissue samples from B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer patients. The first column provides the molecular weight, the second column gives information on the subfractionation protocol used, if any (see Example 1 below), and the last column provides a list of the sequences observed by mass spectrometry and the corresponding SEQ ID Nos.

Tables 6-9 below illustrates the different occurrences of OGTA301 as detected by iTRAQ and mass spectrometry of membrane protein extracts of colorectal, kidney, liver, lung and ovarian tissue samples from colorectal cancer, kidney cancer, liver cancer, lung cancer and ovarian cancer patients. The first column provides the samples batch number, the second column gives the iTRAQ experiment number and the last column provides a list of the sequences observed by mass spectrometry and the corresponding SEQ ID Nos.

OGTA014

TABLE 1a

Acute T-cell leukaemia 1D gel

| MW (Da) | Subfractionation | Tryptics identified [SEQ ID No] |
|---|---|---|
|  |  | LFFVGSR [44], SADGSAPAGEGEGVTLQR [65] RRALAAPAAEEK [63], SADGSAPAGEGEGVTLQR [65] |

TABLE 1b

B-cell non-Hodgkin's lymphoma 1D gel

| MW (Da) | Subfractionation | Tryptics identified [SEQ ID No] |
|---|---|---|
| 32603 |  | GDVSNLDPNFSFEGTK [30], KPELERPIK [42], RRALAAPAAEEK [63], SADGSAPAGEGEGVTLQR [65] |
| 34340 |  | KPELERPIK [42], SADGSAPAGEGEGVTLQR [65] |
| 43799 |  | KPELERPIK [42], MAGAGPKRR [50], SADGSAPAGEGEGVTLQR [65] |
| 45164 |  | KPELERPIK [42], SADGSAPAGEGEGVTLQR [65] |

TABLE 1c

Breast cancer 1D gel

| MW (Da) | Subfractionation | Tryptics identified [SEQ ID No] |
|---|---|---|
|  |  | ALAAPAAEEK [8], DPLTIQWAR [21], DPLTIQWARR [22], KPELERPIK [42], LFFVGSR [44], MAGAGPKR [49], MAGAGPKRR [50], SADGSAPAGEGEGVTLQR [65], VQDAFAAAK [81] |
|  |  | LFFVGSR [44], MAGPKRR [50], SADGSAPAGEGEGVTLQR [65], VQDAFAAAK [81] |
| 28438 | Vesicles | MAGAGPKR [49], SADGSAPAGEGEGVTLQR [65] |

TABLE 1c-continued

Breast cancer 1D gel

| MW (Da) | Subfractionation | Tryptics identified [SEQ ID No] |
|---|---|---|
| 31483 | Vesicles | LPGVPGPAGAQSMAGAGPK [46], LPGVPGPAGAQSMAGAGPKRR [47], NLMNSLGTQDQMSVSLA [52], SADGSAPAGEGEGVTLQR [65] |
| 32329 | | SADGSAPAGEGEGVTLQR [65] |
| 32824 | | KPELERPIK [42], SADGSAPAGEGEGVTLQR [65] |
| 33078 | | KPELERPIK [42], SADGSAPAGEGEGVTLQR [65] |
| 33573 | | ALAAPAAEEK [8], SADGSAPAGEGEGVTLQR [65] |
| 33601 | | SADGSAPAGEGEGVTLQR [65] |
| 33870 | | KPELERPIK [42], MAGAGPKRR [50], SADGSAPAGEGEGVTLQR [65] |
| 33903 | | KPELERPIK [42], MAGAGPKRR [50], SADGSAPAGEGEGVTLQR [65] |
| 34145 | | KPELERPIK [42], SADGSAPAGEGEGVTLQR [65] |
| 34425 | | GDVSNLDPNFSFEGTK [30], SADGSAPAGEGEGVTLQR [65] |
| 34711 | | SADGSAPAGEGEGVTLQR [65] |
| 35002 | | SADGSAPAGEGEGVTLQR [65] |
| 35009 | | DPLTIQWAR [21], LPGVPGPAGAQSMAGAGPK [46], NLMNSLGTQDQMSVSLA [52], SADGSAPAGEGEGVTLQR [65] |
| 35300 | | SADGSAPAGEGEGVTLQR [65] |
| 35311 | | SADGSAPAGEGEGVTLQR [65] |
| 35620 | | SADGSAPAGEGEGVTLQR [65] |
| 42434 | | SADGSAPAGEGEGVTLQR [65] |
| 44612 | | SADGSAPAGEGEGVTLQR [65] |
| 52069 | | MAGAGPKRR [50], SADGSAPAGEGEGVTLQR [65] |
| 105930 | | SADGSAPAGEGEGVTLQR [65] |

TABLE 1d

Colorectal cancer 1D gel

| MW (Da) | Subfractionation | Tryptics identified [SEQ ID No] |
|---|---|---|
| 39228 | | SADGSAPAGEGEGVTLQR [65] |
| 39618 | | SADGSAPAGEGEGVTLQR [65] |
| 119837 | Nucleotide Binding | SADGSAPAGEGEGVTLQR [65] |
| 125678 | Nucleotide Binding | KPELERPIK [42], MAGAGPKRR [50], SADGSAPAGEGEGVTLQR [65] |
| 148039 | Nucleotide Binding | SADGSAPAGEGEGVTLQR [65] |

TABLE 1e

Hepatocellular carcinoma 1D gel

| MW (Da) | Subfractionation | Tryptics identified [SEQ ID No] |
|---|---|---|
| 39010 | | ALAAPAAEEK [8], SADGSAPAGEGEGVTLQR [65] |
| 111122 | | NLMNSLGTQDQMSVSLA [52], RNLMNSLGTQDQMSVSLA [61], SADGSAPAGEGEGVTLQR [65], SGGDYAYMLEVYGSLPAFLK [66] |

TABLE 1f

Lung cancer 1D gel

| MW (Da) | Subfractionation | Tryptics identified [SEQ ID No] |
|---|---|---|
| 20148 | | KPELERPIK [42], SADGSAPAGEGEGVTLQR [65] |
| 36099 | | SADGSAPAGEGEGVTLQR [65] |
| 37082 | | SADGSAPAGEGEGVTLQR [65] |
| 37766 | | ALAAPAAEEK [8], GDVSNLDPNFSFEGTK [30], MAGAGPKRR [50], SADGSAPAGEGEGVTLQR [65] |
| 38473 | | KPELERPIK [42], SADGSAPAGEGEGVTLQR [65] |
| 39206 | | ALAAPAAEEK [8], SADGSAPAGEGEGVTLQR [65] |
| 39417 | | RRALAAPAAEEK [63], SADGSAPAGEGEGVTLQR [65] |
| 40180 | | LFFVGSR [44], SADGSAPAGEGEGVTLQR [65] |

TABLE 1g

Lymphoid leukaemia, unspecified 1D gel

| MW (Da) | Subfractionation | Tryptics identified [SEQ ID No] |
|---|---|---|
| 31321 | | SADGSAPAGEGEGVTLQR [65] |
| 31538 | | KPELERPIK [42], SADGSAPAGEGEGVTLQR [65] |

TABLE 1h

Melanoma 1D gel

| MW (Da) | Subfractionation | Tryptics identified [SEQ ID No] |
|---|---|---|
| 23597 | | SADGSAPAGEGEGVTLQR [65], SGGDYAYMLEVYGSLPAFLK [66] |
| 24412 | | GDVSNLDPNFSFEGTK [30], SADGSAPAGEGEGVTLQR [65] |
| 25096 | | SADGSAPAGEGEGVTLQR [65] |
| 25340 | | SADGSAPAGEGEGVTLQR [65] |

TABLE 1i

Osteosarcoma 1D gel

| MW (Da) | Subfractionation | Tryptics identified [SEQ ID No] |
|---|---|---|
| 27001 | | SADGSAPAGEGEGVTLQR [65] |
| 125805 | | SADGSAPAGEGEGVTLQR [65] |

TABLE 1j

Ovarian cancer 1D gel

| MW (Da) | Subfractionation | Tryptics identified [SEQ ID No] |
|---|---|---|
| 26138 | | GDVSNLDPNFSFEGTK [30], SADGSAPAGEGEGVTLQR [65] |
| 26397 | | GDVSNLDPNFSFEGTK [30], SADGSAPAGEGEGVTLQR [65] |
| 26666 | | SADGSAPAGEGEGVTLQR [65], SGGDYAYMLEVYGSLPAFLK [66] |
| 26943 | | SADGSAPAGEGEGVTLQR [65], SGGDYAYMLEVYGSLPAFLK [66] |
| 27529 | | GDVSNLDPNFSFEGTK [30], SADGSAPAGEGEGVTLQR [65] |

TABLE 1k

Pancreatic cancer 1D gel

| MW (Da) | Subfractionation | Tryptics identified [SEQ ID No] |
|---|---|---|
| 30609 | | SADGSAPAGEGEGVTLQR [65] |
| 37333 | | RRALAAPAAEEK [63], SADGSAPAGEGEGVTLQR [65] |
| 37597 | | ALAAPAAEEK [8], RRALAAPAAEEK [63], SADGSAPAGEGEGVTLQR [65] |
| 37866 | | RRALAAPAAEEK [63], SADGSAPAGEGEGVTLQR [65], VQDAFAAAK [81] |
| 37964 | | MAGAGPKRR [50], SADGSAPAGEGEGVTLQR [65] |
| 38140 | | RRALAAPAAEEK [63], SADGSAPAGEGEGVTLQR [65] |

TABLE 1k-continued

Pancreatic cancer 1D gel

| MW (Da) | Subfractionation | Tryptics identified [SEQ ID No] |
|---|---|---|
| 38418 | | GDVSNLDPNFSFEGTK [30], MAGAGPKRR [50], RRALAAPAAEEK [63], SADGSAPAGEGEGVTLQR [65] |
| 38701 | | KPELERPIK [42], MAGAGPKRR [50], RRALAAPAAEEK [63], SADGSAPAGEGEGVTLQR [65], VQDAFAAAK [81] |
| 38990 | | KPELERPIK [42], MAGAGPKRR [50], RRALAAPAAEEK [63], SADGSAPAGEGEGVTLQR [65] |
| 39284 | | GDVSNLDPNFSFEGTK [30], KPELERPIK [42], RRALAAPAAEEK [63], SADGSAPAGEGEGVTLQR [65], VQDAFAAAK [81] |
| 39426 | | GDVSNLDPNFSFEGTK [30], SADGSAPAGEGEGVTLQR [65] |
| 42700 | | SADGSAPAGEGEGVTLQR [65] |
| 541754 | | SADGSAPAGEGEGVTLQR [65] |

TABLE 1l

Renal cell cancer 1D gel

| MW (Da) | Subfractionation | Tryptics identified [SEQ ID No] |
|---|---|---|
| 37103 | | ALAAPAAEEK [8], SADGSAPAGEGEGVTLQR [65], SGGDYAYMLEVYGSLPAFLK [66] |
| 37830 | | ALAAPAAEEK [8], KPELERPIK [42], MAGAGPKRR [50], SADGSAPAGEGEGVTLQR [65] |

OGTA020

TABLE 2a

Colorectal cancer 1D gel

| MW (Da) | Subfractionation | Tryptics identified [SEQ ID No] |
|---|---|---|
| 98419 | | AKPLMELIER [7], EFSEHFR [24], QTPEGAER [58], RRDEELIYHK [64], TPESSHEGLITDPHSPSR [72], TSSFLDQR [75] |
| 101142 | | AKPLMELIER [7], AQVYYR [10], EFSEHFR [24], RQTECMVEQYSNYSVNGEPVNGR [62], RRDEELIYHK [64], TSSFLDQR [75] |

TABLE 2b

Hepatocellular carcinoma 1D gel

| MW (Da) | Subfractionation | Tryptics identified [SEQ ID No] |
|---|---|---|
| 73669 | | ANPVPDGHSR [9], DGNLRPWWK [18], EFSEHFR [24], TSSFLDQR [75] |
| 75736 | | AKPLMELIER [7], ANPVPDGHSR [9], DGNLRPWWK [18], EFSEHFR [24], KAQVYYR [41], RRDEELIYHK [64], TSSFLDQR [75] |
| 82606 | | ANPVPDGHSR [9], DNFQDTLQVVTAHYR [20], EFSEHFR [24], FMEVMYGTKK [28], HLLENSTASVSEAERK [36], RRDEELIYHK [64], TPESSHEGLITDPHSPSR [72] |
| 86381 | | AKPLMELIER [7], ANPVPDGHSR [9], DGNLRPWWK [18], EFSEHFR [24], KTSSFLDQR [43] |
| 101388 | | AYQNWVK [12], TSPFFSVYVSADSK [74] |
| 119689 | | AKPLMELIER [7], CPPGSPMNPPHK [16], DNFQDTLQVVTAHYR [20], EFSEHFR [24], TPESSHEGLITDPHSPSR [72], TSSFLDQR [75] |

TABLE 2c

Lung cancer 1D gel

| MW (Da) | Subfractionation | Tryptics identified [SEQ ID No] |
|---|---|---|
| | | EFSEHFR [24] |
| 113648 | | AKPLMELIER [7], CLLNNYMIWNLVRK [15], EFSEHFR [24], NSSVEAFK [54], TQVEKR [73] |
| 119354 | | AQVYYR [10], DNFQDTLQVVTAHYR [20], EFSEHFR [24], NEIVFPAGILQAPFYTR [51], QTECMVEQYSNYSVNGEPVNGR [57], RQTECMVEQYSNYSVNGEPVNGR [62], RRDEELIYHK [64], TPESSHEGLITDPHSPSR [72] |

TABLE 2d

Melanoma 1D gel

| MW (Da) | Subfractionation | Tryptics identified [SEQ ID No] |
|---|---|---|
| 97855 | | DGNLRPWWK [18], DNFQDTLQVVTAHYR [20], |

TABLE 2d-continued

Melanoma 1D gel

| MW (Da) | Subfractionation | Tryptics identified [SEQ ID No] |
|---|---|---|
| | | EFSEHFR [24], NEIVFPAGILQAPFYTR [51], RRDEELIYHK [64] |

TABLE 2e

Pancreatic cancer 1D gel

| MW (Da) | Subfractionation | Tryptics identified [SEQ ID No] |
|---|---|---|
| 107693 | | AKPLMELIER [7], CLLNNYMIWNLVRK [15], DGNLRPWWK [18], DNFQDTLQVVTAHYR [20], EFSEHFR [24], FMEVMYGTKK [28], NSSVEAFKR [55], RRDEELIYHK [64], TPESSHEGLITDPHSPSR [72] |
| 111297 | | AKPLMELIER [7], AQVYYR [10], CLLNNYMIWNLVR [14], DGNLRPWWK [18], EFSEHFR [24], HLLENSTASVSEAERK [36], HTLGENIADNGGLK [37], KTSSFLDQR [43], NSNSNVIQVDQSGLGLPSR [53], RQTECMVEQYSNYSVNGEPVNGR [62], RRDEELIYHK [64], TPESSHEGLITDPHSPSR [72] |
| 113324 | | AQVYYR [10], CLLNNYMIWNLVR [14], DNFQDTLQVVTAHYR [20], EFSEHFR [24], GVWPPPVSALLSALGMSTYKR [33], HLLENSTASVSEAER [35], TPESSHEGLITDPHSPSR [72], TSSFLDQR [75] |
| 116302 | | AQVYYR [10], CLLNNYMIWNLVR [14], DNFQDTLQVVTAHYR [20], EFSEHFR [24], HLLENSTASVSEAER [35], HTLGENIADNGGLK [37], RRDEELIYHK [64], TPESSHEGLITDPHSPSR [72], TSSFLDQR [75] |
| 119435 | | AQVYYR [10], DNFQDTLQVVTAHYR [20], EFSEHFR [24], NEIVFPAGILQAPFYTR [51], NSNSNVIQVDQSGLGLPSR [53], RDEELIYHK [59], RRDEELIYHK [64], TPESSHEGLITDPHSPSR [72], WGTFSNLWEHNQAIIK [83] |
| 119656 | | ANPVPDGHSR [9], AQVYYR [10], AYQNWVK [12], DGNLRPWWK [18], EFSEHFR [24], FMEVMYGTKK [28], HTLGENIADNGGLK [37], KTSSFLDQR [43], RRDEELIYHK [64], |

TABLE 2e-continued

Pancreatic cancer 1D gel

| MW (Da) | Subfractionation | Tryptics identified [SEQ ID No] |
|---|---|---|
| | | TPESSHEGLITDPHSPSR [72], TSPFFSVYVSADSK [74] |
| 122219 | | AKPLMELIER [7], ANPVPDGHSR [9], AQVYYR [10], CPPGSPMNPPHK [16], DGNLRPWWK [18], DNFQDTLQVVTAHYR [20], EFSEHFR [24], HLLENSTASVSEAER [35], HLLENSTASVSEAERK [36], KTSSFLDQR [43], NSNSNVIQVDQSGLGLPSR [53], RDEELIYHK [59], RRDEELIYHK [64], TPESSHEGLITDPHSPSR [72] |
| 128213 | | AKPLMELIER [7], ANPVPDGHSR [9], AQVYYR [10], AYQNWVK [12], DGNLRPWWK [18], DNFQDTLQVVTAHYR [20], EFSEHFR [24], HTLGENIADNGGLK [37], KTSSFLDQR [43], RDEELIYHK [59], RRDEELIYHK [64], TPESSHEGLITDPHSPSR [72] |

TABLE 2f

Renal cell cancer 1D gel

| MW (Da) | Subfractionation | Tryptics identified [SEQ ID No] |
|---|---|---|
| 112922 | | AKPLMELIER [7], ANPVPDGHSR [9], EFSEHFR [24] |
| 114462 | | AKPLMELIER [7], AYQNWVKK [13], DNFQDTLQVVTAHYR [20], NSNSNVIQVDQSGLGLPSR [53], TSSFLDQR [75], VLTGYLNYMVQLGK [80] |
| 122597 | | AKPLMELIER [7], CLLNNYMIWNLVR [14], DNFQDTLQVVTAHYR [20], EFSEHFR [24], FMEVMYGTKK [28], FQDADEK [29], HLLENSTASVSEAER [35], TPESSHEGLITDPHSPSR [72] |
| 128813 | | AKPLMELIER [7], EFSEHFR [24], NEIVFPAGILQAPFYTR [51], NSNSNVIQVDQSGLGLPSR [53], TPESSHEGLITDPHSPSR [72], TQVEKR [73], VLTGYLNYMVQLGK [80] |

OGTA067

TABLE 3a

Colorectal cancer 1D gel

| MW (Da) | Subfractionation | Tryptics identified [SEQ ID No] |
|---|---|---|
| 130363 | | CSVPEGPFPGHLVDVR [17] |

TABLE 3b

Ovarian cancer 1D gel

| MW (Da) | Subfractionation | Tryptics identified [SEQ ID No] |
|---|---|---|
| 108400 | | ATEPGLFGVWAHNGEVR [11], DLGLGLTEMSTR [19], ISLCLICISCLLYVK [40], SGTAQVR [67] |

OGTA116

TABLE 4a

Gastric cancer 1D gel

| MW (Da) | Subfractionation | Tryptics identified [SEQ ID No] |
|---|---|---|
| 65769 | | FLANVNDR [27] |

TABLE 4b

Hepatocellular carcinoma 1D gel

| MW (Da) | Subfractionation | Tryptics identified [SEQ ID No] |
|---|---|---|
| 73478 | | VIYAMAEDGLLFK [78] |
| 106345 | | FLANVNDR [27], PFPGDGGTR [56], VLLNIGQQMLR [79] |
| 107073 | | FLANVNDR [27], VIYAMAEDGLLFK [78] |
| 121636 | | VIYAMAEDGLLFK [78], VLLNIGQQMLR [79] |

TABLE 4c

Pancreatic cancer 1D gel

| MW (Da) | Subfractionation | Tryptics identified [SEQ ID No] |
|---|---|---|
| 86463 | | FLANVNDR [27] |
| 110489 | | VLLNIGQQMLR [79] |
| 208929 | | FLANVNDR [27], VIYAMAEDGLLFK [78], VLLNIGQQMLR [79] |
| 229012 | | VLLNIGQQMLR [79] |

OGTA194

TABLE 5a

B-cell non-Hodgkin's lymphoma 1D gel

| MW (Da) | Subfractionation | Tryptics identified [SEQ ID No] |
|---|---|---|
| 91238 | | ESGVFEGIPTYR [25] |

TABLE 5b

Breast cancer 1D gel

| MW (Da) | Subfractionation | Tryptics identified [SEQ ID No] |
|---|---|---|
| | | ESGVFEGIPTYR [25], LIMTLAFTTLGER [45], TVGEIMWGYK [76], YFPGMFPFK [85] |
| | | ESGVFEGIPTYR [25], GEKPQVR [31], GPYVYR [32], IHLVDK [39], LQLSLYMK [48], TFQFQPSK [71] |
| | | ESGVFEGIPTYR [25], LQLSLYMK [48], SQPPNQHPTLK [69], TVGEIMWGYK [76], WNGLSK [84] |
| 59316 | | ESGVFEGIPTYR [25] |
| 60402 | | ESGVFEGIPTYR [25], GEKPQVR [31], GPYVYR [32], LIMTLAFTTLGER [45], TFQFQPSK [71] |
| 80120 | | ESGVFEGIPTYR [25], TFQFQPSK [71] |

TABLE 5c

Colorectal cancer 1D gel

| MW (Da) | Subfractination | Tryptics identified [SEQ ID No] |
|---|---|---|
| 63406 | | ESGVFEGIPTYR [25] |
| 64479 | | ESGVFEGIPTYR [25], LIMTLAFTTLGER [45] |
| 71809 | | ESGVFEGIPTYR [25], TFQFQPSK [71] |
| 78011 | Nucleotide Binding | DPLVNLINK [23], IDPSSLSFNMWK [38], TFQFQPSK [71] |

TABLE 5d

Hepatocellular carcinoma 1D gel

| MW (Da) | Subfractionation | Tryptics identified [SEQ ID No] |
|---|---|---|
| 54732 | | ESGVFEGIPTYR [25], LQLSLYMK [48] |
| 64252 | | DPLVNLINK [23], ESGVFEGIPTYR [25], SNITFNNNDTVSFLEYR [68] |
| 64272 | | ESGVFEGIPTYR [25], IDPSSLSFNMWK [38] |

TABLE 5d-continued

Hepatocellular carcinoma 1D gel

| MW (Da) | Subfractionation | Tryptics identified [SEQ ID No] |
|---|---|---|
| 68429 | | ESGVFEGIPTYR [25], LQLSLYMK [48] |
| 81528 | | ESGVFEGIPTYR [25], TFQFQPSK [71] |

TABLE 5e

Lung cancer 1D gel

| MW (Da) | Subfractionation | Tryptics identified [SEQ ID No] |
|---|---|---|
| 84649 | | ESGVFEGIPTYR [25] |

TABLE 5f

Melanoma 1D gel

| MW (Da) | Subfractionation | Tryptics identified [SEQ ID No] |
|---|---|---|
| 49790 | | ESGVFEGIPTYR [25], TFQFQPSK [71] |
| 57594 | | ESGVFEGIPTYR [25], TFQFQPSK [71] |
| 75738 | | DPLVNLINK [23], ESGVFEGIPTYR [25] |

TABLE 5g

Ovarian cancer 1D gel

| MW (Da) | Subfractionation | Tryptics identified [SEQ ID No] |
|---|---|---|
| 43041 | | DPLVNLINK [23], ESGVFEGIPTYR [25], GPYVYR [32], LIMTLAFTTLGER [45] |

TABLE 5h

Pancreatic cancer 1D gel

| MW (Da) | Subfractionation | Tryptics identified [SEQ ID No] |
|---|---|---|
| 55542 | | DPLVNLINK [23], ESGVFEGIPTYR [25], GPYVYR [32], LIMTLAFTTLGER [45], YFPGMFPFK [85] |
| 56548 | | DPLVNLINK [23], GPYVYR [32], LIMTLAFTTLGER [45] |
| 65765 | | ESGVFEGIPTYR [25], LIMTLAFTTLGER [45], TFQFQPSK [71] |
| 69116 | | DPLVNLINK [23], ESGVFEGIPTYR [25], LIMTLAFTTLGER [45], LQLSLYMK [48], TFQFQPSK [71] |

TABLE 5h-continued

Pancreatic cancer 1D gel

| MW (Da) | Subfractionation | Tryptics identified [SEQ ID No] |
|---|---|---|
| 70329 | | ESGVFEGIPTYR [25], TFQFQPSK [71] |
| 78602 | | ESGVFEGIPTYR [25], TFQFQPSK [71] |

TABLE 5i

Prostate cancer 1D gel

| MW (Da) | Subfractionation | Tryptics identified [SEQ ID No] |
|---|---|---|
| | Digitonin Insoluble, Triton X114, Detergent Soluble | ESGVFEGIPTYR [25], GEKPQVR [31], GPYVYR [32], TVGEIMWGYK [76] |

TABLE 5j

Renal cell cancer 1D gel

| MW (Da) | Subfractionation | Tryptics identified [SEQ ID No] |
|---|---|---|
| 69582 | | ESGVFEGIPTYR [25], TFQFQPSK [71], TVGEIMWGYK [76] |
| 76987 | | DPLVNLINK [23], ESGVFEGIPTYR [25], LIMTLAFTTLGER [45] |
| 80084 | | DPLVNLINK [23], ESGVFEGIPTYR [25] |

OGTA014

TABLE 6a

Colorectal cancer iTRAQ

| Samples batch no. | Experiment no. | Tryptics identified [SEQ ID No] |
|---|---|---|
| Samples 1 | Experiment 1 | SADGSAPAGEGEGVTLQR [65] |

TABLE 6b

Non-small cell lung cancer iTRAQ

| Sample no. | Experiment no. | Tryptics identified [SEQ ID No] |
|---|---|---|
| Samples 1 | Experiment 1 | SADGSAPAGEGEGVTLQR [65] |
| Samples 1 | Experiment 2 | MLAAKSADGSAPAGEGEGVTLQR [92] |

OGTA020

TABLE 7a

Kidney cancer iTRAQ

| Sample no. | Experiment no. | Tryptics identified [SEQ ID No] |
|---|---|---|
| Samples 1 | Experiment 1 | RDEELIYHK [95] |

OGTA067

TABLE 8a

Kidney cancer iTRAQ

| Sample no. | Experiment no. | Tryptics identified [SEQ ID No] |
|---|---|---|
| Samples 1 | Experiment 1 | LVVLVK [93] |

OGTA194

TABLE 9a

Ovarian cancer iTRAQ

| Samples batch no. | Experiment no. | Tryptics identified [SEQ ID No] |
|---|---|---|
| Samples 1 | Experiment 1 | QQVLK [94] |

TABLE 9b

Non-small cell lung cancer iTRAQ

| Sample no. | Experiment no. | Tryptics identified [SEQ ID No] |
|---|---|---|
| Samples 1 | Experiment 1 | QQVLK [94] |
| Samples 1 | Experiment 2 | QQVLK [94] |

TABLE 9c

Small cell lung cancer iTRAQ

| Sample no. | Experiment no. | Tryptics identified [SEQ ID No] |
|---|---|---|
| Samples 1 | Experiment 1 | QQVLK [94] |

For proteins of the invention, the detected level obtained upon analyzing tissue from subjects having a relevant cancer relative to the detected level obtained upon analyzing tissue from subjects free from said cancers will depend upon the particular analytical protocol and detection technique that is used. Accordingly, the present invention contemplates that each laboratory will establish a reference range in subjects free from said cancers according to the analytical protocol and detection technique in use, as is conventional in the diagnostic art. Preferably, at least one control positive tissue sample from a subject known to have a relevant cancer or at least one control negative tissue sample from a subject known to be free from said cancer (and more preferably both positive and negative control samples) are included in each batch of test samples analyzed.

Proteins of the invention can be used for detection, prognosis, diagnosis, or monitoring of a relevant cancer or for drug development. In one embodiment of the invention, tissue from a subject (e.g., a subject suspected of having a relevant cancer) is analyzed by 1D electrophoresis or iTRAQ for detection of a protein of the invention. An increased abundance of a protein of the invention in the tissue from the subject relative to tissue from a subject or subjects free from said cancer (e.g., a control sample) or a previously determined reference range indicates the presence of a relevant cancer.

In particular, OGTA014 can be used for detection, prognosis, diagnosis, or monitoring of B-cell non-Hodgkin's lymphoma, breast cancer, colorectal cancer, hepatocellular carcinoma, lung cancer, lymphoid leukaemia (particularly acute T-cell leukaemia), melanoma, osteosarcoma, ovarian cancer, pancreatic cancer and renal cell cancer.

In particular, OGTA020 can be used for detection, prognosis, diagnosis, or monitoring of colorectal cancer, hepatocellular carcinoma, lung cancer, melanoma, pancreatic cancer and renal cell cancer.

In particular, OGTA067 can be used for detection, prognosis, diagnosis, or monitoring of colorectal cancer, kidney cancer and ovarian cancer, such as colorectal cancer and ovarian cancer.

In particular, OGTA116 can be used for detection, prognosis, diagnosis, or monitoring of gastric cancer, hepatocellular carcinoma and pancreatic cancer.

In particular, OGTA194 can be used for detection, prognosis, diagnosis, or monitoring of B-cell non-Hodgkin's lymphoma, breast cancer, colorectal cancer, hepatocellular carcinoma, lung cancer, melanoma, ovarian cancer, pancreatic cancer, prostate cancer and renal cell cancer.

OGTA014 may, in particular, be characterized as an isoform having a MW substantially as recited (e.g. +/−10%, particularly +/−5% of the value) in column 1 of any of the rows of Tables 1a-1l.

OGTA020 may, in particular, be characterized as an isoform having a MW substantially as recited (e.g. +/−10%, particularly +/−5% of the value) in column 1 of any of the rows of Tables 2a-2f.

OGTA067 may, in particular, be characterized as an isoform having a MW substantially as recited (e.g. +/−10%, particularly +/−5% of the value) in column 1 of any of the rows of Table 3a-3b.

OGTA116 may, in particular, be characterized as an isoform having a MW substantially as recited (e.g. +/−10%, particularly +/−5% of the value) in column 1 of any of the rows of Tables 4a-4c.

OGTA194 may, in particular, be characterized as an isoform having a MW substantially as recited (e.g. +/−10%, particularly +/−5% of the value) in column 1 of any of the rows of Tables 5a-5j.

In relation to fragments, immunogenic fragments or antigenic fragments of OGTA014:
for acute T-cell leukaemia applications: preferably these comprise one or more of the sequences identified as tryptic sequences in the $3^{rd}$ column of Table 1a;
for B-cell non-Hodgkin's lymphoma applications: preferably these comprise one or more of the sequences identified as tryptic sequences in the $3^{rd}$ column of Table 1b;
for breast cancer applications: preferably these comprise one or more of the sequences identified as tryptic sequences in the $3^{rd}$ column of Table 1c;
for colorectal cancer applications: preferably these comprise one or more of the sequences identified as tryptic sequences in the $3^{rd}$ column of Table 1d or Table 6a;
for hepatocellular carcinoma applications: preferably these comprise one or more of the sequences identified as tryptic sequences in the $3^{rd}$ column of Table 1e;
for lung cancer applications: preferably these comprise one or more of the sequences identified as tryptic sequences in the $3^{rd}$ column of Table 1f or Table 6b;
for lymphoid leukaemia applications: preferably these comprise one or more of the sequences identified as tryptic sequences in the $3^{rd}$ column of Table 1g;
for melanoma applications: preferably these comprise one or more of the sequences identified as tryptic sequences in the $3^{rd}$ column of Table 1h;
for osteosarcoma applications: preferably these comprise one or more of the sequences identified as tryptic sequences in the $3^{rd}$ column of Table 1i;
for ovarian cancer applications: preferably these comprise one or more of the sequences identified as tryptic sequences in the $3^{rd}$ column of Table 1j;
for pancreatic cancer applications: preferably these comprise one or more of the sequences identified as tryptic sequences in the $3^{rd}$ column of Table 1k;
for renal cell cancer applications: preferably these comprise one or more of the sequences identified as tryptic sequences in the $3^{rd}$ column of Table 1l.

In relation to fragments, immunogenic fragments or antigenic fragments of OGTA020:
for colorectal cancer applications: preferably these comprise one or more of the sequences identified as tryptic sequences in the $3^{rd}$ column of Table 2a;
for hepatocellular carcinoma applications: preferably these comprise one or more of the sequences identified as tryptic sequences in the $3^{rd}$ column of Table 2b;
for lung cancer applications: preferably these comprise one or more of the sequences identified as tryptic sequences in the $3^{rd}$ column of Table 2c;
for melanoma applications: preferably these comprise one or more of the sequences identified as tryptic sequences in the $3^{rd}$ column of Table 2d;
for pancreatic cancer applications: preferably these comprise one or more of the sequences identified as tryptic sequences in the $3^{rd}$ column of Table 2e;
for renal cell cancer applications: preferably these comprise one or more of the sequences identified as tryptic sequences in the $3^{rd}$ column of Table 2f or Table 7a.

In relation to fragments, immunogenic fragments or antigenic fragments of OGTA067:
for colorectal cancer applications: preferably these comprise one or more of the sequences identified as tryptic sequences in the $3^{rd}$ column of Table 3a;
for kidney cancer applications: preferably these comprise one or more of the sequences identified as tryptic sequences in the $3^{rd}$ column of Table 8a;
for ovarian cancer applications: preferably these comprise one or more of the sequences identified as tryptic sequences in the $3^{rd}$ column of Table 3b.

In relation to fragments, immunogenic fragments or antigenic fragments of OGTA116:
for gastric cancer applications: preferably these comprise one or more of the sequences identified as tryptic sequences in the $3^{rd}$ column of Table 4a;
for hepatocellular carcinoma applications: preferably these comprise one or more of the sequences identified as tryptic sequences in the $3^{rd}$ column of Table 4b;
for pancreatic cancer applications: preferably these comprise one or more of the sequences identified as tryptic sequences in the $3^{rd}$ column of Table 4c.

In relation to fragments, immunogenic fragments or antigenic fragments of OGTA194:

for B-cell non-Hodgkin's lymphoma applications: preferably these comprise one or more of the sequences identified as tryptic sequences in the 3$^{rd}$ column of Table 5a;

for breast cancer applications: preferably these comprise one or more of the sequences identified as tryptic sequences in the 3$^{rd}$ column of Table 5b;

for colorectal cancer applications: preferably these comprise one or more of the sequences identified as tryptic sequences in the 3$^{rd}$ column of Table 5c;

for hepatocellular carcinoma applications: preferably these comprise one or more of the sequences identified as tryptic sequences in the 3$^{rd}$ column of Table 5d;

for lung cancer applications: preferably these comprise one or more of the sequences identified as tryptic sequences in the 3$^{rd}$ column of Table 5e, Table 9b or Table 9c;

for melanoma applications: preferably these comprise one or more of the sequences identified as tryptic sequences in the 3$^{rd}$ column of Table 5f;

for ovarian cancer applications: preferably these comprise one or more of the sequences identified as tryptic sequences in the 3$^{rd}$ column of Table 5g or Table 9a;

for pancreatic cancer applications: preferably these comprise one or more of the sequences identified as tryptic sequences in the 3$^{rd}$ column of Table 5h;

for prostate cancer applications: preferably these comprise one or more of the sequences identified as tryptic sequences in the 3$^{rd}$ column of Table 5i;

for renal cell cancer applications: preferably these comprise one or more of the sequences identified as tryptic sequences in the 3$^{rd}$ column of Table 5j.

The present invention additionally provides: (a) preparations comprising isolated protein of the invention; (b) preparations comprising one or more fragments of a protein of the invention; and (c) antibodies or other affinity reagents that bind to a protein of the invention, to said fragments, or both to a protein of the invention and to said fragments. As used herein, proteins of the invention are "isolated" when they are present in preparations that are substantially free of contaminating proteins, i.e., preparations in which less than 10% by weight (preferably less than 5%, more preferably less than 1%) of the total protein present is contaminating protein(s). A contaminating protein is a protein having a significantly different amino acid sequence from that of an isolated protein of the invention, as determined by mass spectral analysis. As used herein, a "significantly different" sequence is one that permits the contaminating protein to be resolved from a protein of the invention by mass spectral analysis, performed according to the Reference Protocols.

Proteins of the invention can be assayed by any method known to those skilled in the art, including but not limited to, the Preferred Technologies described herein, kinase assays, enzyme assays, binding assays and other functional assays, immunoassays, and western blotting. In one embodiment, proteins of the invention are separated on 1-D gels by virtue of their MW and visualized by staining the gel. In one embodiment, proteins of the invention are stained with a fluorescent dye and imaged with a fluorescence scanner. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety. In another embodiment, proteins of the invention are analyzed using isobaric tags for relative and absolute quantification (iTRAQ).

Alternatively, proteins of the invention can be detected in an immunoassay. In one embodiment, an immunoassay is performed by contacting a sample from a subject to be tested with an anti-OGTA014, anti-OGTA020, anti-OGTA067, anti-OGTA116 or anti-OGTA194 antibody (or other affinity reagent) under conditions such that immunospecific binding can occur if a protein of the invention is present, and detecting or measuring the amount of any immunospecific binding by the affinity reagent. Anti-OGTA014, anti-OGTA020, anti-OGTA067, anti-OGTA116, anti-OGTA194 and anti-OGTA218 affinity reagents can be produced by the methods and techniques taught herein.

Proteins of the invention may be detected by virtue of the detection of a fragment thereof e.g. an immunogenic or antigenic fragment thereof. Fragments may have a length of at least 10, more typically at least 20 amino acids e.g. at least 50 or 100 amino acids e.g. at least 200 or 500 amino acids e.g. at least 1000 amino acids.

In one embodiment, binding of antibody (or other affinity reagent) in tissue sections can be used to detect aberrant OGTA(s) localization or an aberrant level of OGTA(s). In a specific embodiment, an antibody (or other affinity reagent) to a protein of the invention can be used to assay a patient tissue (e.g., a lymphoid, breast, colorectal, gastric, liver, lung, skin, osteoblast, ovarian, pancreatic, prostate or kidney tissue) for the level of a protein of the invention where an aberrant level of a protein of the invention is indicative of a relevant cancer. As used herein, an "aberrant level" means a level that is increased compared with the level in a subject free from said cancer or a reference level.

Any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

For example, proteins of the invention can be detected in a fluid sample (e.g., blood, urine, or saliva) by means of a two-step sandwich assay. In the first step, a capture reagent (e.g., an anti-OGTA014, anti-OGTA020, anti-OGTA067, anti-OGTA116 or anti-OGTA194 antibody or other affinity reagent) is used to capture a protein of the invention. The capture reagent can optionally be immobilized on a solid phase. In the second step, a directly or indirectly labeled detection reagent is used to detect the captured a protein of the invention. In one embodiment, the detection reagent is a lectin. Any lectin can be used for this purpose that preferentially binds to a protein of the invention rather than to other isoforms that have the same core protein as a protein of the invention or to other proteins that share the antigenic determinant recognized by the antibody. In one embodiment, the chosen lectin binds a protein of the invention with at least 2-fold greater affinity, more preferably at least 5-fold greater affinity, still more preferably at least 10-fold greater affinity, than to said other isoforms that have the same core protein as a protein of the invention or to said other proteins that share the antigenic determinant recognized by the affinity reagent. Based on the present description, a lectin that is suitable for detecting a protein of the invention can readily be identified by methods well known in the art, for instance upon testing one or more lectins enumerated in Table I on pages 158-159 of Sumar et al., Lectins as Indicators of Disease-Associated Glycoforms, In: Gabius H-J & Gabius S (eds.), 1993, Lectins and Glycobiology, at pp. 158-174 (which is incorporated herein by reference in its entirety). In an alternative embodiment, the detection reagent is an antibody (or other affinity reagent), e.g., an antibody that immunospecifically detects other post-translational modifications, such as an antibody that immunospecifically binds to phosphorylated amino acids. Examples of such antibodies include those that bind to phosphotyrosine (BD Transduction Laboratories, catalog nos.: P11230-050/P11230-150; P11120; P38820; P39020), those that bind to phosphoserine (Zymed Laboratories Inc., South San Francisco, Calif., catalog no. 61-8100) and those that bind to phosphothreonine (Zymed Laboratories Inc., South San Francisco, Calif., catalogue nos. 71-8200, 13-9200).

If desired, a gene encoding a protein of the invention, a related gene, or related nucleic acid sequences or subsequences, including complementary sequences, can also be used in hybridization assays. A nucleotide encoding a protein of the invention, or subsequences thereof comprising at least 8 nucleotides, preferably at least 12 nucleotides, and most preferably at least 15 nucleotides can be used as a hybridization probe. Hybridization assays can be used for detection, prognosis, diagnosis, or monitoring of conditions, disorders, or disease states, associated with aberrant expression of the gene encoding a protein of the invention, or for differential diagnosis of subjects with signs or symptoms suggestive of a relevant cancer. In particular, such a hybridization assay can be carried out by a method comprising contacting a subject's sample containing nucleic acid with a nucleic acid probe capable of hybridizing to a DNA or RNA that encodes a protein of the invention, under conditions such that hybridization can occur, and detecting or measuring any resulting hybridization.

Hence nucleic acid encoding a protein of the invention (e.g. DNA or more suitably RNA) may be detected, for example, using a hybridizing agent capable of hybridizing to nucleic acid encoding a protein of the invention.

One such exemplary method comprises:
(a) contacting one or more oligonucleotide probes comprising 10 or more consecutive nucleotides complementary to a nucleotide sequence encoding a protein of the invention, with an RNA obtained from a biological sample from the subject or with cDNA copied from the RNA, wherein said contacting occurs under conditions that permit hybridization to the probe if an appropriate nucleotide sequence is present;
(b) detecting hybridization, if any, between the probe and the nucleotide sequence; and
(c) comparing the hybridization, if any, detected in step (b) with the hybridization detected in a control sample, or with a previously determined reference range.

The invention also provides diagnostic kits, comprising an anti-OGTA014, anti-OGTA020, anti-OGTA067, anti-OGTA116 or anti-OGTA194 antibody (or other affinity reagent). In addition, such a kit may optionally comprise one or more of the following: (1) instructions for using the anti-OGTA014, anti-OGTA020, anti-OGTA067, anti-OGTA116 or anti-OGTA194 affinity reagent for diagnosis, prognosis, therapeutic monitoring or any combination of these applications; (2) a labeled binding partner to the affinity reagent; (3) a solid phase (such as a reagent strip) upon which the anti-OGTA014, anti-OGTA020, anti-OGTA067, anti-OGTA116 or anti-OGTA194 affinity reagent is immobilized; and (4) a label or insert indicating regulatory approval for diagnostic, prognostic or therapeutic use or any combination thereof. If no labeled binding partner to the affinity reagent is provided, the anti-OGTA014, anti-OGTA020, anti-OGTA067, anti-OGTA116 or anti-OGTA194 affinity reagent itself can be labeled with a detectable marker, e.g., a chemiluminescent, enzymatic, fluorescent, or radioactive moiety.

The invention also provides a kit comprising a nucleic acid probe capable of hybridizing to RNA encoding a protein of the invention. In a specific embodiment, a kit comprises in one or more containers a pair of primers (e.g., each in the size range of 6-30 nucleotides, more preferably 10-30 nucleotides and still more preferably 10-20 nucleotides) that under appropriate reaction conditions can prime amplification of at least a portion of a nucleic acid encoding a protein of the invention, such as by polymerase chain reaction (see, e.g., Innis et al., 1990, PCR Protocols, Academic Press, Inc., San Diego, Calif.), ligase chain reaction (see EP 320,308) use of Qβ replicase, cyclic probe reaction, or other methods known in the art.

A kit can optionally further comprise a predetermined amount of a protein of the invention or a nucleic acid encoding a protein of the invention, e.g., for use as a standard or control.

Use in Clinical Studies

The diagnostic methods and compositions of the present invention can assist in monitoring a clinical study, e.g. to evaluate drugs for therapy of a relevant cancer. In one embodiment, candidate molecules are tested for their ability to restore levels of a protein of the invention in a subject having a relevant cancer to levels found in subjects free from said cancer, in a treated subject, to preserve levels of a protein of the invention at or near non-B-cell non-Hodgkin's lymphoma, non-breast cancer, non-colorectal cancer, non-gastric cancer, non-hepatocellular carcinoma, non-lung cancer, non-lymphoid leukaemia (particularly acute T-cell leukaemia), non-melanoma, non-osteosarcoma, non-ovarian cancer, non-pancreatic cancer, non-prostate cancer or non-renal cell cancer values.

In another embodiment, the methods and compositions of the present invention are used to screen candidates for a clinical study to identify individuals having a relevant cancer; such individuals can then be excluded from the study or can be placed in a separate cohort for treatment or analysis.

Production of Proteins of the Invention and Corresponding Nucleic Acid

A DNA of the present invention can be obtained by isolation as a cDNA fragment from cDNA libraries using as starter materials commercial mRNAs and determining and identifying the nucleotide sequences thereof. That is, specifically, clones are randomly isolated from cDNA libraries, which are prepared according to Ohara et al's method (DNA Research Vol. 4, 53-59 (1997)). Next, through hybridization, duplicated clones (which appear repeatedly) are removed and then in vitro transcription and translation are carried out. Nucleotide sequences of both termini of clones, for which products of 50 kDa or more are confirmed, are determined. Furthermore, databases of known genes are searched for homology using the thus obtained terminal nucleotide sequences as queries. The entire nucleotide sequence of a clone revealed to be novel as a result is determined. In addition to the above screening method, the 5' and 3' terminal sequences of cDNA are related to a human genome sequence. Then an unknown long-chain gene is confirmed in a region between the sequences, and the full-length of the cDNA is analyzed. In this way, an unknown gene that is unable to be obtained by a conventional cloning method that depends on known genes can be systematically cloned.

Moreover, all of the regions of a human-derived gene containing a DNA of the present invention can also be prepared using a PCR method such as RACE while paying sufficient attention to prevent artificial errors from taking place in short fragments or obtained sequences. As described above, clones having DNA of the present invention can be obtained.

In another means for cloning DNA of the present invention, a synthetic DNA primer having an appropriate nucleotide sequence of a portion of a polypeptide of the present invention is produced, followed by amplification by the PCR method using an appropriate library. Alternatively, selection can be carried out by hybridization of the DNA of the present invention with a DNA that has been incorporated into an appropriate vector and labeled with a DNA fragment or a synthetic DNA encoding some or all of the regions of the polypeptide of the present invention. Hybridization can be carried out by, for example, the method described in Current Protocols in Molecular Biology (edited by Frederick M. Ausubel et al., 1987). DNA of the present invention may be any DNA, as long as they contain nucleotide sequences encoding the polypeptides of the present invention as described above. Such a DNA may be a cDNA identified and isolated from cDNA libraries or the like that are derived from lymphoid, breast, colorectal, gastric, liver, lung, skin, osteoblast, ovarian, pancreatic, prostate or kidney tissue. Such a DNA may also be a synthetic DNA or the like. Vectors for use in library construction may be any of bacteriophages, plasmids, cosmids, phargemids, or the like. Furthermore, by the use of a total RNA fraction or a mRNA fraction prepared from the above cells and/or tissues, amplification can be carried out by a direct reverse transcription coupled polymerase chain reaction (hereinafter abbreviated as "RT-PCR method").

DNA encoding the above polypeptides consisting of amino acid sequences that are substantially identical to the amino acid sequences of the proteins of the invention or DNA encoding the above polypeptides consisting of amino acid sequences derived from the amino acid sequences of the proteins of the invention by deletion, substitution, or addition of one or more amino acids composing a portion of the amino acid sequence can be easily produced by an appropriate combination of, for example, a site-directed mutagenesis method, a gene homologous recombination method, a primer elongation method, and the PCR method known by persons skilled in the art. In addition, at this time, a possible method for causing a polypeptide to have substantially equivalent biological activity is substitution of homologous amino acids (e.g. polar and nonpolar amino acids, hydrophobic and hydrophilic amino acids, positively-charged and negatively charged amino acids, and aromatic amino acids) among amino acids composing the polypeptide. Furthermore, to maintain substantially equivalent biological activity, amino acids within functional domains contained in each polypeptide of the present invention are preferably conserved.

Furthermore, examples of DNA of the present invention include DNA comprising the nucleotide sequences represented by SEQ ID NO: 86, SEQ ID NO: 87, SEQ ID NO: 88, SEQ ID NO: 89 and SEQ ID NO: 90 and comprising nucleotide sequences that encode the amino acid sequences of the proteins of the invention and DNA hybridizing under stringent conditions to the DNA and encoding polypeptides (proteins) having biological activity (functions) equivalent to the functions of the polypeptides consisting of the amino acid sequence of a protein of the invention. Under such conditions, an example of such DNA capable of hybridizing to DNA comprising the nucleotide sequences represented by SEQ ID NO: 86, SEQ ID NO: 87, SEQ ID NO: 88, SEQ ID NO: 89 and SEQ ID NO: 90 and comprising the nucleotide sequences that encode the amino acid sequences of the proteins of the invention is DNA comprising nucleotide sequences that have a degree of overall mean homology with the entire nucleotide sequence of the DNA, such as approximately 80% or more, preferably approximately 90% or more, and more preferably approximately 95% or more. Hybridization can be carried out according to a method known in the art such as a method described in Current Protocols in Molecular Biology (edited by Frederick M. Ausubel et al., 1987) or a method according thereto. Here, "stringent conditions" are, for example, conditions of approximately "1*SSC, 0.1% SDS, and 37° C., more stringent conditions of approximately "0.5*SSC, 0.1% SDS, and 42° C., or even more stringent conditions of approximately "0.2*SSC, 0.1% SDS, and 65° C. With more stringent hybridization conditions, the isolation of a DNA having high homology with a probe sequence can be expected. The above combinations of SSC, SDS, and temperature conditions are given for illustrative purposes. Stringency similar to the above can be achieved by persons skilled in the art using an appropriate combination of the above factors or other factors (for example, probe concentration, probe length, and reaction time for hybridization) for determination of hybridization stringency.

A cloned DNA of the present invention can be directly used or used, if desired, after digestion with a restriction enzyme or addition of a linker, depending on purposes. The DNA may have ATG as a translation initiation codon at the 5' terminal side and have TAA, TGA, or TAG as a translation termination codon at the 3' terminal side. These translation initiation and translation termination codons can also be added using an appropriate synthetic DNA adapter.

In methods of the invention the OGTA employed may for example be provided in isolated form, such as a form where the polypeptide has been purified to at least to some extent. The polypeptide may be provided in substantially pure form, that is to say free, to a substantial extent, from other proteins. The polypeptide can also be produced using recombinant methods, synthetically produced or produced by a combination of these methods. OGTA(s) according to the invention can be easily prepared by any method known by persons skilled in the art, which involves producing an expression vector containing a DNA of the present invention or a gene containing a DNA of the present invention, culturing a transformant transformed using the expression vector, generating and accumulating a polypeptide of the present invention or a recombinant protein containing the polypeptide, and then collecting the resultant.

Recombinant OGTA(s) polypeptide may be prepared by processes well known in the art from genetically engineered host cells comprising expression systems. Accordingly, the present invention also relates to expression systems which comprise an OGTA(s) polypeptide or nucleic acid of the invention, to host cells which are genetically engineered with such expression systems and to the production of OGTA(s) polypeptide by recombinant techniques. For recombinant polypeptide production, host cells can be genetically engineered to incorporate expression systems or portions thereof for nucleic acids of the invention. Such incorporation can be performed using methods well known in the art, such as, calcium phosphate transfection, DEAD-dextran mediated transfection, transvection, microinjection, cationic lipid-mediated transfection, electroporation, transduction, scrape loading, ballistic introduction or infection (see e.g. Davis et al., Basic Methods in Molecular Biology, 1986 and Sambrook et al., Molecular Cloning: A Laboratory Manual, 2nd Ed., Cold Spring Harbour laboratory Press, Cold Spring Harbour, NY, 1989).

As host cells, for example, bacteria of the genus *Escherichia*, *Streptococci*, *Staphylococci*, *Streptomyces*, bacteria of the genus *Bacillus*, yeast, *Aspergillus* cells, insect cells, insects, and animal cells are used. Specific examples of bacteria of the genus *Escherichia*, which are used herein, include *Escherichia coli* K12 and DH1 (Proc. Natl. Acad. Sci. U.S.A., Vol. 60, 160 (1968)), JM103 (Nucleic Acids Research, Vol. 9, 309 (1981)), JA221 (Journal of Molecular Biology, Vol. 120, 517 (1978)), and HB101 (Journal of Molecular Biology, Vol. 41, 459 (1969)). As bacteria of the genus *Bacillus*, for example, *Bacillus subtilis* MI114 (Gene, Vol. 24, 255 (1983)) and 207-21 (Journal of Biochemistry, Vol. 95, 87 (1984)) are used. As yeast, for example, *Saccaromyces cerevisiae* AH22, AH22R-, NA87-11A, DKD-5D, and 20B-12, *Schizosaccaromyces pombe* NCYC1913 and NCYC2036, and *Pichia pastoris* are used. As insect cells, for example, *Drosophila* S2 and *Spodoptera* Sf9 cells are used. As animal cells, for example, COS-7 and Vero monkey cells, CHO Chinese hamster cells (hereinafter abbreviated as CHO cells), dhfr-gene-deficient CHO cells, mouse L cells, mouse AtT-20 cells, mouse myeloma cells, rat GH3 cells, human FL cells, COS, HeLa, C127,3T3, HEK 293, BHK and Bowes melanoma cells are used.

Cell-free translation systems can also be employed to produce recombinant polypeptides (e.g. rabbit reticulocyte lysate, wheat germ lysate, SP6/T7 in vitro T&T and RTS 100 *E. Coli* HY transcription and translation kits from Roche Diagnostics Ltd., Lewes, UK and the TNT Quick coupled Transcription/Translation System from Promega UK, Southampton, UK).

The expression vector can be produced according to a method known in the art. For example, the vector can be produced by (1) excising a DNA fragment containing a DNA of the present invention or a gene containing a DNA of the present invention and (2) ligating the DNA fragment downstream of the promoter in an appropriate expression vector. A wide variety of expression systems can be used, such as and without limitation, chromosomal, episomal and virus-derived systems, e.g. plasmids derived from *Escherichia coli* (e.g. pBR322, pBR325, pUC18, and pUC118), plasmids derived from *Bacillus subtilis* (e.g. pUB110, pTP5, and pC194), from bacteriophage, from transposons, from yeast episomes (e.g. pSH19 and pSH15), from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage (such as [lambda] phage) genetic elements, such as cosmids and phagemids. The expression systems may contain control regions that regulate as well as engender expression. Promoters to be used in the present invention may be any promoters as long as they are appropriate for hosts to be used for gene expression. For example, when a host is *Escherichia coli*, a trp promoter, a lac promoter, a recA promoter, a pL promoter, an 1pp promoter, and the like are preferred. When a host is *Bacillus subtilis*, an SPO1 promoter, an SPO2 promoter, a penP promoter, and the like are preferred. When a host is yeast, a PHOS promoter, a PGK promoter, a GAP promoter, an ADH promoter, and the like are preferred.

When an animal cell is used as a host, examples of promoters for use in this case include an SRa promoter, an SV40 promoter, an LTR promoter, a CMV promoter, and an HSV-TK promoter. Generally, any system or vector that is able to maintain, propagate or express a nucleic acid to produce a polypeptide in a host may be used.

The appropriate nucleic acid sequence may be inserted into an expression system by any variety of well known and routine techniques, such as those set forth in Sambrook et al., supra. Appropriate secretion signals may be incorporated into the OGTA(s) polypeptide to allow secretion of the translated protein into the lumen of the endoplasmic reticulum, the periplasmic space or the extracellular environment. These signals may be endogenous to the OGTA(s) polypeptide or they may be heterologous signals. Transformation of the host cells can be carried out according to methods known in the art. For example, the following documents can be referred to: Proc. Natl. Acad. Sci. U.S.A., Vol. 69, 2110 (1972); Gene, Vol. 17, 107 (1982); Molecular & General Genetics, Vol. 168, 111 (1979); Methods in Enzymology, Vol. 194, 182-187 (1991); Proc. Natl. Acad. Sci. U.S.A.), Vol. 75, 1929 (1978); Cell Technology, separate volume 8, New Cell Technology, Experimental Protocol. 263-267 (1995) (issued by Shujunsha); and Virology, Vol. 52, 456 (1973). The thus obtained transformant transformed with an expression vector containing a DNA of the present invention or a gene containing a DNA of the present invention can be cultured according to a method known in the art. For example, when hosts are bacteria of the genus *Escherichia*, the bacteria are generally cultured at approximately 15° C. to 43° C. for approximately 3 to 24 hours. If necessary, aeration or agitation can also be added. When hosts are bacteria of the genus *Bacillus*, the bacteria are generally cultured at approximately 30° C. to 40° C. for approximately 6 to 24 hours. If necessary, aeration or agitation can also be added. When transformants whose hosts are yeast are cultured, culture is generally carried out at approximately 20° C. to 35° C. for approximately 24 to 72 hours using media with pH adjusted to be approximately 5 to 8. If necessary, aeration or agitation can also be added. When transformants whose hosts are animal cells are cultured, the cells are generally cultured at approximately 30° C. to 40° C. for approximately 15 to 60 hours using media with the pH adjusted to be approximately 6 to 8. If necessary, aeration or agitation can also be added.

If an OGTA(s) polypeptide is to be expressed for use in cell-based screening assays, it is preferred that the polypeptide be produced at the cell surface. In this event, the cells may be harvested prior to use in the screening assay. If the OGTA polypeptide is secreted into the medium, the medium can be recovered in order to isolate said polypeptide. If produced intracellularly, the cells must first be lysed before the OGTA polypeptide is recovered.

OGTA polypeptide can be recovered and purified from recombinant cell cultures or from other biological sources by well known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, a combination of these methods is used. In another embodiment, high performance liquid chromatography is used. In a further embodiment, an antibody which specifically binds to an OGTA polypeptide can be used to deplete a sample comprising a relevant OGTA polypeptide of said polypeptide or to purify said polypeptide.

To separate and purify a polypeptide or a protein of the present invention from the culture products, for example, after culture, microbial bodies or cells are collected by a known method, they are suspended in an appropriate buffer, the microbial bodies or the cells are disrupted by, for example, ultrasonic waves, lysozymes, and/or freeze-thawing, the resultant is then subjected to centrifugation or filtration, and then a crude extract of the protein can be obtained. The buffer may also contain a protein denaturation agent such as urea or guanidine hydrochloride or a surfactant such as Triton X-100™. When the protein is secreted in a culture solution, microbial bodies or cells and a supernatant are separated by a known method after the completion of culture and then the supernatant is collected. The protein contained in the thus obtained culture supernatant or the extract can be purified by an appropriate combination of known separation and purification methods. The thus obtained polypeptide (protein) of the present invention can be converted into a salt by a known method or a method according thereto. Conversely, when the polypeptide (protein) of the present invention is obtained in the form of a salt, it can be converted into a free protein or peptide or another salt by a known method or a method according thereto. Moreover, an appropriate protein modification enzyme such as trypsin or chymotrypsin is caused to act on a protein produced by a recombinant before or after purification, so that modification can be arbitrarily added or a polypeptide can be partially removed. The presence of a polypeptide (protein) of the present invention or a salt thereof can be measured by various binding assays, enzyme immunoassays using specific antibodies, and the like.

Techniques well known in the art, may be used for refolding to regenerate native or active conformations of the OGTA polypeptide when the polypeptides have been denatured during isolation and or purification. In the context of the present invention, OGTA polypeptide can be obtained from a biological sample from any source, such as and without limitation, a blood sample or tissue sample, e.g. lymphoid, breast, colorectal, gastric, liver, lung, skin, osteoblast, ovarian, pancreatic, prostate or kidney tissue sample.

OGTA polypeptide may be in the form of a "mature protein" or may be part of a larger protein such as a fusion protein. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag.

An additional sequence that may provide stability during recombinant production may also be used. Such sequences may be optionally removed as required by incorporating a cleavable sequence as an additional sequence or part thereof. Thus, an OGTA polypeptide may be fused to other moieties including other polypeptides or proteins (for example, glutathione S-transferase and protein A). Such a fusion protein can be cleaved using an appropriate protease, and then separated into each protein. Such additional sequences and affinity tags are well known in the art. In addition to the above, features known in the art, such as an enhancer, a splicing signal, a polyA addition signal, a selection marker, and an SV40 replication origin can be added to an expression vector, if desired.

Production of Affinity Reagents to the Proteins of the Invention

According to those in the art, there are three main types of immunoaffinity reagent—monoclonal antibodies, phage display antibodies and smaller antibody-derived molecules such as Affibodies, Domain Antibodies (dAbs), Nanobodies or UniBodies. In general in applications according to the present invention where the use of antibodies is stated, other affinity reagents (e.g. Affibodies, domain antibodies, Nanobodies or UniBodies) may be employed. Such substances may be said to be capable of immunospecific binding to the proteins of the invention. Where appropriate the term "affinity agent" shall be construed to embrace immunoaffinity reagents and other substances capable of specific binding to the proteins of the invention including but not limited to ligands, lectins, streptavidins, antibody mimetics and synthetic binding agents.

Production of Antibodies to the Proteins of the Invention

According to the invention OGTA014, OGTA020, OGTA067, OGTA116 or OGTA194 an analog of the same, a related protein or a fragment or derivative of any of the foregoing may be used as an immunogen to generate antibodies which immunospecifically bind such an immunogen. Such immunogens can be isolated by any convenient means, including the methods described above. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3$^{rd}$ Edition, W. E. Paul, ed., Raven Press, N.Y. (1993); Wilson (1994) J. Immunol. Methods 175: 267-273; Yarmush (1992) J. Biochem. Biophys. Methods 25:85-97. The term antibody includes antigen-binding portions, i.e. "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody". Antibodies of the invention include, but are not limited to polyclonal, monoclonal, bispecific, humanized or chimeric antibodies, single chain antibodies, Fab fragments and F(ab')$_2$ fragments, fragments produced by a Fab expression library, anti-idiotypic (anti-Id) antibodies, and epitope-binding fragments of any of the above. The immunoglobulin molecules of the invention can be of any class (e.g., IgG, IgE, IgM, IgD and IgA) or subclass of immunoglobulin molecule.

The term "specifically binds" (or "immunospecifically binds") is not intended to indicate that an antibody binds exclusively to its intended target. Rather, an antibody "specifically binds" if its affinity for its intended target is about 5-fold greater when compared to its affinity for a non-target molecule. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, specific binding between an antibody or other binding agent and an antigen means a binding affinity of at least $10^6 M^{-1}$. Preferred antibodies bind with affinities of at least about $10^7 M^{-1}$, and preferably between about $10^8 M^{-1}$ to about $10^9 M^{-1}$, about $10^9 M^{-1}$ to about $10^{10} M^{-1}$, or about $10^{10} M^{-1}$ to about $10^{11} M^{-1}$.

Affinity is calculated as $K_d = k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labeled ligand at various concentrations (c). The data are graphed using the Scatchard equation: r/c=K(n−r):

where
r=moles of bound ligand/mole of receptor at equilibrium;
c=free ligand concentration at equilibrium;
K=equilibrium association constant; and
n=number of ligand binding sites per receptor molecule
By graphical analysis, r/c is plotted on the Y-axis versus r on the X-axis thus producing a Scatchard plot. The affinity is the negative slope of the line. $k_{off}$ can be determined by competing bound labeled ligand with unlabeled excess ligand (see, e.g., U.S. Pat. No. 6,316,409). The affinity of a targeting agent for its target molecule is preferably at least about $1 \times 10^{-6}$ moles/liter, is more preferably at least about $1 \times 10^{-7}$ moles/liter, is even more preferably at least about $1 \times 10^{-8}$ moles/liter, is yet even more preferably at least about $1 \times 10^{-9}$ moles/liter, and is most preferably at least about $1 \times 10^{-10}$ moles/liter. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

In one embodiment, antibodies that recognize gene products of genes encoding a protein of the invention are publicly available. In another embodiment, methods known to those skilled in the art are used to produce antibodies that recognise a protein of the invention, an analog thereof, a related polypeptide, or a fragment or derivative of any of the foregoing. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In one embodiment of the invention, antibodies to a specific domain of a protein of the invention are produced. In a specific embodiment, hydrophilic fragments of a protein of the invention are used as immunogens for antibody production.

In the production of antibodies, screening for the desired antibody can be accomplished by techniques known in the art, e.g. ELISA (enzyme-linked immunosorbent assay). For example, to select antibodies which recognize a specific domain of a protein of the invention, one may assay generated hybridomas for a product which binds to an OGTA fragment containing such domain. For selection of an antibody that specifically binds a first OGTA homologue but which does not specifically bind to (or binds less avidly to) a second OGTA homologue, one can select on the basis of positive binding to the first OGTA homologue and a lack of binding to (or reduced binding to) the second OGTA homologue. Similarly, for selection of an antibody that specifically binds a protein of the invention but which does not specifically bind to (or binds less avidly to) a different isoform of the same protein (such as a different glycoform having the same core peptide as a protein of the invention), one can select on the basis of positive binding to a protein of the invention and a lack of binding to (or reduced binding to) the different isoform (e.g., a different glycoform). Thus, the present invention provides an antibody (preferably a monoclonal antibody) that binds with greater affinity (for example at least 2-fold, such as at least 5-fold, particularly at least 10-fold greater affinity) to a protein of the invention than to a different isoform or isoforms (e.g., glycoforms) of a protein of the invention.

Polyclonal antibodies which may be used in the methods of the invention are heterogeneous populations of antibody molecules derived from the sera of immunized animals. Unfractionated immune serum can also be used. Various procedures known in the art may be used for the production of polyclonal antibodies to a protein of the invention, a fragment thereof, a related polypeptide, or a fragment of an OGTA related polypeptide. For example, one way is to purify polypeptides of interest or to synthesize the polypeptides of interest using, e.g., solid phase peptide synthesis methods well known in the art. See, e.g., *Guide to Protein Purification*, Murray P. Deutcher, ed., *Meth. Enzymol.* Vol 182 (1990); Solid Phase Peptide Synthesis, Greg B. Fields ed., *Meth. Enzymol.* Vol 289 (1997); Kiso et al., *Chem. Pharm. Bull.* (Tokyo) 38: 1192-99, 1990; Mostafavi et al., *Biomed. Pept. Proteins Nucleic Acids* 1: 255-60, 1995; Fujiwara et al., *Chem. Pharm. Bull.* (Tokyo) 44: 1326-31, 1996. The selected polypeptides may then be used to immunize by injection various host animals, including but not limited to rabbits, mice, rats, etc., to generate polyclonal or monoclonal antibodies. The Preferred Technology described herein in Example 1 provides isolated OGTA suitable for such immunization. If an OGTA is purified by gel electrophoresis, it can be used for immunization with or without prior extraction from the polyacrylamide gel. Various adjuvants (i.e. immunostimulants) may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or *corynebacterium parvum*. Additional adjuvants are also well known in the art.

Suitable adjuvants for use in vaccine compositions for the treatment of cancer include: 3De-O-acylated monophosphoryl lipid A (known as 3D-MPL or simply MPL see WO92/116556), a saponin, for example QS21 or QS7, and TLR4 agonists such as a CpG containing molecule, for example as disclosed in WO95/26204.

The adjuvants employed may be a combination of components, for example MPL and QS21 or MPL, QS21 and a CpG containing moiety.

Adjuvants may be formulated as oil-in-water emulsions or liposomal formulations

For preparation of monoclonal antibodies (mAbs) directed toward a protein of the invention, a fragment thereof, a related polypeptide, or a fragment of a related polypeptide, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the invention may be cultivated in vitro or in vivo. In an additional embodiment of the invention, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g., human-mouse chimeras). A chimeric antibody is a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.)

Chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, Bio/Techniques 4:214; U.S. Pat. No. 5,225,539; Jones et al., 1986, Nature 321:552-525; Verhoeyan et al. (1988) Science 239:1534; and Beidler et al., 1988, J. Immunol. 141:4053-4060.

Completely human antibodies are for example desirable for therapeutic treatment of human subjects. Such antibodies can be produced using transgenic mice which are incapable of expressing endogenous immunoglobulin heavy and light chain genes, but which can express human heavy and light chain genes. The transgenic mice are immunized in the normal fashion with a selected antigen, e.g., all or a portion of a protein of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection". In this approach a selected non-human monoclonal antibody, e.g., a mouse antibody, is used to guide the selection of a completely human antibody recognizing the same epitope. (Jespers et al. (1994) Bio/technology 12:899-903).

The antibodies of the present invention can also be generated by the use of phage display technology to produce and screen libraries of polypeptides for binding to a selected target. See, e.g., Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims. In particular, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT Application No. PCT/GB91/01134; PCT Publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

The invention further provides for the use of bispecific antibodies, which can be made by methods known in the art. Traditional production of full length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., 1991, EMBO J. 10:3655-3659.

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details for generating bispecific antibodies see, for example, Suresh et al., Methods in Enzymology, 1986, 121: 210.

The invention provides functionally active fragments, derivatives or analogs of anti-OGTA014, anti-OGTA020, anti-OGTA067, anti-OGTA116 or anti-OGTA194 immunoglobulin molecules. Functionally active means that the fragment, derivative or analog is able to elicit anti-anti-idiotype antibodies (i.e., tertiary antibodies) that recognize the same antigen that is recognized by the antibody from which the fragment, derivative or analog is derived. Specifically, in a preferred embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present invention provides antibody fragments such as, but not limited to, F(ab')$_2$ fragments and Fab fragments. Antibody fragments which recognize specific epitopes may be generated by known techniques. F(ab')$_2$ fragments consist of the variable region, the light chain constant region and the CH1 domain of the heavy chain and are generated by pepsin digestion of the antibody molecule. Fab fragments are generated by reducing the disulfide bridges of the F(ab')$_2$ fragments. The invention also provides heavy chain and light chain dimers of the antibodies of the invention, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the invention. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, Science 242:1038-1041).

In other embodiments, the invention provides fusion proteins of the immunoglobulins of the invention (or functionally active fragments thereof), for example in which the immunoglobulin is fused via a covalent bond (e.g., a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins of the invention include analogs and derivatives that are modified, i.e., by the covalent attachment of any type of molecule as long as such covalent attachment does not impair immunospecific binding. For example, but not by way of limitation, the derivatives and analogs of the immunoglobulins include those that have been further modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

The foregoing antibodies can be used in methods known in the art relating to the localization and activity of a protein of the invention, e.g., for imaging this protein, measuring levels thereof in appropriate physiological samples, in diagnostic methods, etc.

Production of Affibodies to the Proteins of the Invention

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997;15:772-7. Ronmark J, Gronlund H, Uhlen M, Nygren P A, Human immunoglobulin A (IgA)-specific ligands from combinatorial engineering of protein A, Eur J Biochem 2002;269:2647-55.). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli,* J Immunol Methods 2002;261:199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003;16:691-7). Further details of Affibodies and methods of production thereof may be obtained by reference to U.S. Pat. No 5,831,012 which is herein incorporated by reference in its entirety.

Labelled Affibodies may also be useful in imaging applications for determining abundance of Isoforms.

Production of Domain Antibodies to the Proteins of the Invention

Domain Antibodies (dAbs) are the smallest functional binding units of antibodies, corresponding to the variable regions of either the heavy ($V_H$) or light ($V_L$) chains of human antibodies. Domain Antibodies have a molecular weight of approximately 13 kDa. Domantis has developed a series of large and highly functional libraries of fully human $V_H$ and $V_L$ dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Production of Nanobodies to the Proteins of the Invention

Nanobodies are antibody-derived therapeutic proteins that contain the unique structural and functional properties of naturally-occurring heavy-chain antibodies. These heavy-chain antibodies contain a single variable domain (VHH) and two constant domains ($C_H2$ and $C_H3$). Importantly, the cloned and isolated VHH domain is a perfectly stable polypeptide harbouring the full antigen-binding capacity of the original heavy-chain antibody. Nanobodies have a high homology with the VH domains of human antibodies and can be further humanised without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see e.g. WO 04/041867, which is herein incorporated by reference in its entirety) and are easy to manufacture. Other advantages of Nanobodies include recognising uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. E. coli (see e.g. U.S. Pat. No. 6,765,087, which is herein incorporated by reference in its entirety), moulds (for example Aspergillus or Trichoderma) and yeast (for example Saccharomyces, Kluyveromyces, Hansenula or Pichia) (see e.g. U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies against a desired target, based on automated high-throughout selection of B-cells.

Production of UniBodies to the Proteins of the Invention

UniBody is a new proprietary antibody technology that creates a stable, smaller antibody format with an anticipated longer therapeutic window than current small antibody formats. IgG4 antibodies are considered inert and thus do not interact with the immune system. Genmab modified fully human IgG4 antibodies by eliminating the hinge region of the antibody. Unlike the full size IgG4 antibody, the half molecule fragment is very stable and is termed a UniBody. Halving the IgG4 molecule left only one area on the UniBody that can bind to disease targets and the UniBody therefore binds univalently to only one site on target cells. This univalent binding does not stimulate cancer cells to grow like bivalent antibodies might and opens the door for treatment of some types of cancer which ordinary antibodies cannot treat.

The UniBody is about half the size of a regular IgG4 antibody. This small size can be a great benefit when treating some forms of cancer, allowing for better distribution of the molecule over larger solid tumors and potentially increasing efficacy.

Fabs typically do not have a very long half-life. UniBodies, however, were cleared at a similar rate to whole IgG4 antibodies and were able to bind as well as whole antibodies and antibody fragments in pre-clinical studies. Other antibodies primarily work by killing the targeted cells whereas UniBodies only inhibit or silence the cells.

Further details of UniBodies may be obtained by reference to patent WO2007/059782, which is herein incorporated by reference in its entirety.

Expression of Affinity Reagents

Expression of Antibodies

The antibodies of the invention can be produced by any method known in the art for the synthesis of antibodies, in particular, by chemical synthesis or by recombinant expression, and are preferably produced by recombinant expression techniques.

Recombinant expression of antibodies, or fragments, derivatives or analogs thereof, requires construction of a nucleic acid that encodes the antibody. If the nucleotide sequence of the antibody is known, a nucleic acid encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

Alternatively, the nucleic acid encoding the antibody may be obtained by cloning the antibody. If a clone containing the nucleic acid encoding the particular antibody is not available, but the sequence of the antibody molecule is known, a nucleic acid encoding the antibody may be obtained from a suitable source (e.g., an antibody cDNA library, or cDNA library generated from any tissue or cells expressing the antibody) by PCR amplification using synthetic primers hybridizable to the 3' and 5' ends of the sequence or by cloning using an oligonucleotide probe specific for the particular gene sequence.

If an antibody molecule that specifically recognizes a particular antigen is not available (or a source for a cDNA library for cloning a nucleic acid encoding such an antibody), antibodies specific for a particular antigen may be generated by any method known in the art, for example, by immunizing an animal, such as a rabbit, to generate polyclonal antibodies or, more preferably, by generating monoclonal antibodies. Alternatively, a clone encoding at least the Fab portion of the antibody may be obtained by screening Fab expression libraries (e.g., as described in Huse et al., 1989, *Science* 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

Once a nucleic acid encoding at least the variable domain of the antibody molecule is obtained, it may be introduced into a vector containing the nucleotide sequence encoding the constant region of the antibody molecule (see, e.g., PCT Publication WO 86/05807; PCT Publication WO 89/01036; and U.S. Pat. No. 5,122,464). Vectors containing the complete light or heavy chain for co-expression with the nucleic acid to allow the expression of a complete antibody molecule are also available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis, in vitro site directed mutagenesis (Hutchinson et al., 1978, J. Biol. Chem. 253:6551), PCT based methods, etc.

In addition, techniques developed for the production of "chimeric antibodies" (Morrison et al., 1984, Proc. Natl. Acad. Sci. 81:851-855; Neuberger et al., 1984, *Nature* 312:604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human antibody constant region, e.g., humanized antibodies.

Once a nucleic acid encoding an antibody molecule of the invention has been obtained, the vector for the production of the antibody molecule may be produced by recombinant DNA technology using techniques well known in the art. Thus, methods for preparing the proteins of the invention by expressing nucleic acid containing the antibody molecule sequences are described herein. Methods which are well known to those skilled in the art can be used to construct expression vectors containing antibody molecule coding sequences and appropriate transcriptional and translational control signals. These methods include, for example, in vitro recombinant DNA techniques, synthetic techniques, and in vivo genetic recombination. See, for example, the techniques described in Sambrook et al. (1990, Molecular Cloning, A Laboratory Manual, $2^{nd}$ Ed., Cold Spring Harbor Laboratory, Cold Spring Harbor, N.Y.) and Ausubel et al. (eds., 1998, Current Protocols in Molecular Biology, John Wiley & Sons, NY).

The expression vector is transferred to a host cell by conventional techniques and the transfected cells are then cultured by conventional techniques to produce an antibody of the invention.

The host cells used to express a recombinant antibody of the invention may be either bacterial cells such as *Escherichia coli*, or, preferably, eukaryotic cells, especially for the expression of whole recombinant antibody molecule. In particular, mammalian cells such as Chinese hamster ovary cells (CHO), in conjunction with a vector such as the major intermediate early gene promoter element from human cytomegalovirus are an effective expression system for antibodies (Foecking et al., 1986, Gene 45:101; Cockett et al., 1990, Bio/Technology 8:2).

A variety of host-expression vector systems may be utilized to express an antibody molecule of the invention. Such host-expression systems represent vehicles by which the coding sequences of interest may be produced and subsequently purified, but also represent cells which may, when transformed or transfected with the appropriate nucleotide coding sequences, express the antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing the antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the antibody molecule being expressed. For example, when a large quantity of such a protein is to be produced, for the generation of pharmaceutical compositions comprising an antibody molecule, vectors which direct the expression of high levels of fusion protein products that are readily purified may be desirable. Such vectors include, but are not limited to, the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). In mammalian host cells, a number of viral-based expression systems (e.g., an adenovirus expression system) may be utilized.

As discussed above, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein.

For long-term, high-yield production of recombinant antibodies, stable expression is preferred. For example, cell lines that stably express an antibody of interest can be produced by transfecting the cells with an expression vector comprising the nucleotide sequence of the antibody and the nucleotide sequence of a selectable (e.g., neomycin or hygromycin), and selecting for expression of the selectable marker. Such engineered cell lines may be particularly useful in screening and evaluation of compounds that interact directly or indirectly with the antibody molecule.

The expression levels of the antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once an antibody molecule of the invention has been recombinantly expressed, it may be purified by any method known in the art for purification of an antibody molecule, for example, by chromatography (e.g., ion exchange chromatography, affinity chromatography such as with protein A or specific antigen, and sizing column chromatography), centrifugation, differential solubility, or by any other standard technique for the purification of proteins.

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with recombinant vaccinia virus are loaded onto $Ni^{2+}$ nitriloacetic acid-agarose columns and histidine-tagged proteins are selectively eluted with imidazole-containing buffers.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) is present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides, but these approaches do not change the scope of the invention.

For therapeutic applications, antibodies (particularly monoclonal antibodies) may suitably be human or humanized animal (e.g. mouse) antibodies. Animal antibodies may be raised in animals using the human protein (e.g. a protein of the invention) as immunogen. Humanisation typically involves grafting CDRs identified thereby into human framework regions. Normally some subsequent retromutation to optimize the conformation of chains is required. Such processes are known to persons skilled in the art.

Expression of Affibodies

The construction of affibodies has been described elsewhere (Ronnmark J, Gronlund H, Uhlén, M., Nygren P. A°, Human immunoglobulin A (IgA)-specific ligands from combinatorial engineering of protein A, 2002, Eur. J. Biochem. 269, 2647-2655.), including the construction of affibody phage display libraries (Nord, K., Nilsson, J., Nilsson, B., Uhlén, M. & Nygren, P. A°, A combinatorial library of an a-helical bacterial receptor domain, 1995, Protein Eng. 8, 601-608. Nord, K., Gunneriusson, E., Ringdahl, J., Sta°hl, S., Uhlén, M. & Nygren, P. A°, Binding proteins selected from combinatorial libraries of an a-helical bacterial receptor domain, 1997, Nat. Biotechnol. 15, 772-777.)

The biosensor analyses to investigate the optimal affibody variants using biosensor binding studies has also been described elsewhere (Ronnmark J, Gronlund H, Uhlén, M., Nygren P. A°, Human immunoglobulin A (IgA)-specific ligands from combinatorial engineering of protein A, 2002, Eur. J. Biochem. 269, 2647-2655.).

Affinity Reagents Modifications

In a preferred embodiment, anti-OGTA014, anti-OGTA020, anti-OGTA067, anti-OGTA116 or anti-OGTA194 affinity reagents such as antibodies or fragments thereof are conjugated to a diagnostic or therapeutic moiety. The antibodies can be used for diagnosis or to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present invention. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In, and $^{99}$Tc. $^{68}$Ga may also be employed.

Anti-OGTA014, anti-OGTA020, anti-OGTA067, anti-OGTA116, anti-OGTA194 or anti-OGTA218 antibodies or fragments thereof can be conjugated to a therapeutic agent or drug moiety to modify a given biological response. The therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumour necrosis factor, α-interferon, β-interferon, nerve growth factor, platelet derived growth factor, tissue plasminogen activator, a thrombotic agent or an anti-angiogenic agent, e.g., angiostatin or endostatin; or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2$^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Alternatively, an antibody can be conjugated to a second antibody to form an antibody heteroconjugate as described by Segal in U.S. Pat. No. 4,676,980.

An antibody with or without a therapeutic moiety conjugated to it can be used as a therapeutic that is administered alone or in combination with cytotoxic factor(s) and/or cytokine(s).

The invention also provides for fully human, or humanised antibodies that induce antibody-directed cell-mediated cytotoxicity (ADCC). A fully human antibody is one in which the protein sequences are encoded by naturally occurring human immunoglobulin sequences, either from isolated antibody-producing human B-lymphocytes, or from transgenic murine B-lymphocytes of mice in which the murine immunoglobulin coding chromosomal regions have been replaced by orthologous human sequences. Transgenic antibodies of the latter type include, but are not restricted to, HuMab (Medarex, Inc, CA) and Xenomouse (Abgenix Inc., CA). A humanised antibody is one in which the constant region of a non-human antibody molecule of appropriate antigen specificity, is replaced by the constant region of a human antibody, preferably of the IgG subtype, with appropriate effector functions (Morrison et al., 1984, Proc. Natl. Acad. Sci. 81:851-855; Neuberger et al., 1984, Nature 312:604-608; Takeda et al., 1985, Nature 314:452-454). Appropriate effector functions include ADCC, which is a natural process by which fully-human antibodies or humanized antibodies, when bound to targets on the surface of cancer cells, switch on the cell killing properties of lymphocytes that are part of the normal immune system. These active lymphocytes, called Natural Killer (NK) cells, use a cytotoxic process to destroy living cells to which the antibodies are bound. ADCC activity may be detected and quantified by measuring release of Europium (Eu3+) from Eu3+ labelled, living cells in the presence of an antigen-specific antibody and peripheral blood mononuclear cells extracted from an immunocompetent, living human subject. The ADCC process is described in detail in Janeway Jr. C. A. et al., Immunobiology, 5th ed., 2001, Garland Publishing, ISBN 0-8153-3642-X; Pier G. B. et al., Immunology, Infection, and Immunity, 2004, p246-5; Albanell J. et al., Advances in Experimental Medicine and Biology, 2003, 532:p 2153-68 and Weng, W.-K. et al., Journal of Clinical Oncology, 2003, 21:p 3940-3947. Suitable methods for the detection and quantification of ADCC can be found in Blomberg et al., Journal of Immunological Methods. 1986, 86:p 225-9; Blomberg et al., Journal of Immunological Methods. 1986, 21; 92:p 117-23 and Patel & Boyd, Journal of Immunological Methods. 1995, 184:p 29-38.

ADCC typically involves activation of NK cells and is dependent on the recognition of antibody-coated cells by Fc receptors on the surface of the NK cell. The Fc receptors recognize the Fc (crystalline) portion of antibodies such as IgG, bound specifically to the surface of a target cell. The Fc receptor that triggers activation of the NK cell is called CD16 or FcγRIIIa. Once the FcγRIIIa receptor is bound to the IgG Fc, the NK cell releases cytokines such as IFN-γ, and cytotoxic granules containing perforin and granzymes that enter the target cell and promote cell death by triggering apoptosis.

The induction of antibody-dependent cellular cytotoxicity (ADCC) by an antibody can be enhanced by modifications that alter interactions between the antibody constant region (Fc) and various receptors that are present on the surface of cells of the immune system. Such modifications include the reduction or absence of alpha1,6-linked fucose moieties in the complex oligosaccharide chains that are normally added to the Fc of antibodies during natural or recombinant synthesis in mammalian cells. In a preferred embodiment, non-fucosylated anti-OGTA014, anti-OGTA020, anti-OGTA067, anti-OGTA116 or anti-OGTA194 affinity reagents such as antibodies or fragments thereof are produced for the purpose of enhancing their ability to induce the ADCC response.

Techniques for reducing or ablating alpha1,6-linked fucose moieties in the oligosaccharide chains of the Fc are well established. In one example, the recombinant antibody is synthesized in a cell line that is impaired in its ability to add fucose in an alpha 1,6 linkage to the innermost N-acetylglucosamine of the N-linked biantennary complex-type Fc oligosaccharides. Such cell lines include, but are not limited to, the rat hybridoma YB2/0, which expresses a reduced level of the alpha 1,6-fucosyltransferase gene, FUT8. Preferably, the antibody is synthesized in a cell line that is incapable of adding alpha 1,6-linked fucosyl moieties to complex oligosaccharide chains, due to the deletion of both copies of the FUT8 gene. Such cell lines include, but are not limited to, FUT8−/−CHO/DG44 cell lines. Techniques for synthesizing partially fucosylated, or non-fucosylated antibodies and affinity reagents are described in Shinkawa et al., J. Biol. Chem. 278:3466-34735 (2003); Yamane-Ohnuki et al., Biotechnology and Bioengineering 87: 614-22 (2004) and in WO00/61739 A1, WO02/31140 A1 and WO003/085107 A1.

In a second example, the fucosylation of a recombinant antibody is reduced or abolished by synthesis in a cell line that has been genetically engineered to overexpress a glycoprotein-modifying glycosyl transferase at a level that maximizes the production of complex N-linked oligosaccharides carrying bisecting N-acetylglucosamine. For example, the antibody is synthesized in a Chinese Hamster Ovary cell line expressing the enzyme N-acetyl glucosamine transferase III (GnT III). Cell lines stably transfected with suitable glycoprotein-modifying glycosyl transferases, and methods of synthesizing antibodies using these cells are described in WO9954342.

A non-fucosylated antibody or affinity reagent can be used as a therapeutic that is administered alone or in combination with cytotoxic factor(s) and/or cytokine(s).

In a further modification, the amino acid sequences of the antibody Fc are altered in a way that enhances ADCC activation, without affecting ligand affinity. Examples of such modifications are described in Lazar et al., Proceedings of the National Academy of Sciences 2006, 103:p 4005-4010; WO03074679 and WO2007039818. In these examples, substitution of amino acids in the antibody Fc, such as aspartate for serine at position 239, and isoleucine for glutamate at position 332, altered the binding affinity of an antibody for Fc receptors, leading to an increase in ADCC activation.

An antibody reagent with enhanced ADCC activation due to amino acid substitutions can be used as a therapeutic that is administered alone or in combination with cytotoxic factor(s) and/or cytokine(s).

Diagnosis of B-cell Non-Hodgkin's Lymphoma, Breast Cancer, Colorectal Cancer, Gastric Cancer, Hepatocellular Carcinoma, Lung Cancer, Lymphoid Leukaemia (Particularly Acute T-Cell Leukaemia), Melanoma, Osteosarcoma, Ovarian Cancer, Pancreatic Cancer, Prostate Cancer and Renal Cell Cancer In accordance with the present invention, test samples of lymphoid, breast, colorectal, gastric, liver, lung, skin, osteoblast, ovarian, pancreatic, prostate or kidney tissue, serum, plasma or urine obtained from a subject suspected of having or known to have a relevant cancer can be used for diagnosis or monitoring. In one embodiment, a change in the abundance of a protein of the invention in a test sample relative to a control sample (from a subject or subjects free from said cancer) or a previously determined reference range indicates the presence of a relevant cancer. In another embodiment, the relative abundance of a protein of the invention in a test sample compared to a control sample or a previously determined reference range indicates a subtype of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer (e.g. pre-T-cell or mature T-cell acute lymphocytic leukaemia, diffuse large B-cell lymphoma, inflammatory breast cancer, familial or sporadic colorectal cancer, gastrointestinal stromal tumours, fibrolamellar hepatocellular carcinoma, squamous cell lung carcinoma, parosteal or periosteal osteosarcoma, malignant papillary serous adenocarcinoma or endocrine tumours of the pancreas). In yet another embodiment, the relative abundance of a protein of the invention in a test sample relative to a control sample or a previously determined reference range indicates the degree or severity of a relevant cancer (e.g., the likelihood for metastasis). In any of the aforesaid methods, detection of a protein of the invention may optionally be combined with detection of one or more additional biomarkers for a relevant cancer. Any suitable method in the art can be employed to measure the level of a protein of the invention, including but not limited to the Preferred Technologies described herein, kinase assays, immunoassays to detect and/or visualize a protein of the invention (e.g., Western blot, immunoprecipitation followed by sodium dodecyl sulfate polyacrylamide gel electrophoresis, immunocytochemistry, etc.). In a further embodiment, a change in the abundance of mRNA encoding a protein of the invention in a test sample relative to a control sample or a previously determined reference range indicates the presence of a relevant cancer. Any suitable hybridization assay can be used to detect a protein of the invention expression by detecting and/or visualizing mRNA encoding a protein of the invention (e.g., Northern assays, dot blots, in situ hybridization, etc.).

In another embodiment of the invention, labeled antibodies (or other affinity reagents), derivatives and analogs thereof, which specifically bind to a protein of the invention can be used for diagnostic purposes to detect, diagnose, or monitor a relevant cancer. Preferably, a relevant cancer is detected in an animal, more preferably in a mammal and most preferably in a human.

Screening Assays

The invention provides methods for identifying agents (e.g., candidate compounds or test compounds) that bind to a protein of the invention or have a stimulatory or inhibitory effect on the expression or activity of a protein of the invention. The invention also provides methods of identifying agents, candidate compounds or test compounds that bind to an OGTA-related polypeptide or an OGTA fusion protein or have a stimulatory or inhibitory effect on the expression or activity of an OGTA-related polypeptide or an OGTA fusion protein. Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. Nos. 5,738,996; and 5,807,683, each of which is incorporated herein in its entirety by reference).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233, each of which is incorporated herein in its entirety by reference.

Libraries of compounds may be presented, e.g., presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310), each of which is incorporated herein in its entirety by reference.

In one embodiment, agents that interact with (i.e., bind to) a protein of the invention, a fragment thereof (e.g. a functionally active fragment), a related polypeptide, a fragment of a related polypeptide, or an OGTA fusion protein are identified in a cell-based assay system. In accordance with this embodiment, cells expressing a protein of the invention, a fragment thereof, a related polypeptide, a fragment of the related polypeptide, or an OGTA fusion protein are contacted with a candidate compound or a control compound and the ability of the candidate compound to interact with the protein of the invention is determined. If desired, this assay may be used to screen a plurality (e.g. a library) of candidate compounds. The cell, for example, can be of prokaryotic origin (e.g., *E. coli*) or eukaryotic origin (e.g., yeast or mammalian). Further, the cells can express a protein of the invention, a fragment thereof, a related polypeptide, a fragment of a related polypeptide, or an OGTA fusion protein endogenously or be genetically engineered to express a protein of the invention, a fragment thereof, a related polypeptide, a fragment of a related polypeptide, or an OGTA fusion protein. In certain instances, a protein of the invention, a fragment thereof, a related polypeptide, a fragment of a related polypeptide, or an OGTA fusion protein or the candidate compound is labeled, for example with a radioactive label (such as $^{32}P$, $^{35}S$, and $^{125}I$) or a fluorescent label (such as fluorescein isothiocyanate, rhodamine, phycoerythrin, phycocyanin, allophycocyanin, o-phthaldehyde or fluorescamine) to enable detection of an interaction between a protein of the invention and a candidate compound. The ability of the candidate compound to interact directly or indirectly with a protein of the invention, a fragment of thereof, a related polypeptide, a fragment of a related polypeptide, or an OGTA fusion protein can be determined by methods known to those of skill in the art. For example, the interaction between a candidate compound and a protein of the invention, a related polypeptide, a fragment of a related polypeptide, or an OGTA fusion protein can be determined by flow cytometry, a scintillation assay, immunoprecipitation or western blot analysis.

In another embodiment, agents that interact with (i.e., bind to) a protein of the invention, a fragment thereof (e.g., a functionally active fragment), a related polypeptide, a fragment of a related polypeptide, or an OGTA fusion protein are identified in a cell-free assay system. In accordance with this embodiment, a native or recombinant OGTA or fragment thereof, or a native or recombinant OGTA-related polypeptide or fragment thereof, or an OGTA fusion protein or fragment thereof, is contacted with a candidate compound or a control compound and the ability of the candidate compound to interact with OGTA or the related polypeptide, or the OGTA fusion protein is determined. If desired, this assay may be used to screen a plurality (e.g. a library) of candidate compounds. In one embodiment, a protein of the invention, a fragment thereof, a related polypeptide, a fragment of a related polypeptide, or an OGTA fusion protein is first immobilized, by, for example, contacting a protein of the invention, a fragment thereof, a related polypeptide, a fragment of a related polypeptide, or an OGTA fusion protein with an immobilized antibody (or other affinity reagent) which specifically recognizes and binds it, or by contacting a purified preparation of a protein of the invention, a fragment thereof, a related polypeptide, a fragment of a related polypeptide, or an OGTA fusion protein with a surface designed to bind proteins. A protein of the invention, a fragment thereof, a related polypeptide, a fragment of a related polypeptide, or an OGTA fusion protein may be partially or completely purified (e.g., partially or completely free of other polypeptides) or part of a cell lysate. Further, a protein of the invention, a fragment thereof, a related polypeptide, a fragment of a related polypeptide may be a fusion protein comprising a protein of the invention or a biologically active portion thereof, or an OGTA-related polypeptide and a domain such as glutathionine-S-transferase. Alternatively, a protein of the invention, a fragment thereof, a related polypeptide, a fragment of a related polypeptide or an OGTA fusion protein can be biotinylated using techniques well known to those of skill in the art (e.g., biotinylation kit, Pierce Chemicals; Rockford, Ill.). The ability of the candidate compound to interact with a protein of the invention, a fragment thereof, a related polypeptide, a fragment of a related polypeptide, or an OGTA fusion protein can be determined by methods known to those of skill in the art.

In another embodiment, a cell-based assay system is used to identify agents that bind to or modulate the activity of a protein, such as an enzyme, or a biologically active portion thereof, which is responsible for the production or degradation of a protein of the invention or is responsible for the post-translational modification of a protein of the invention. In a primary screen, a plurality (e.g., a library) of compounds are contacted with cells that naturally or recombinantly express: (i) a protein of the invention, an isoform of a protein of the invention, an OGTA homologue, an OGTA-related polypeptide, an OGTA fusion protein, or a biologically active fragment of any of the foregoing; and (ii) a protein that is responsible for processing of a protein of the invention, an OGTA isoform, an OGTA homologue, an OGTA-related polypeptide, an OGTA fusion protein, or fragment in order to identify compounds that modulate the production, degradation, or post-translational modification of a protein of the invention, an OGTA isoform, an OGTA homologue, an OGTA-related polypeptide, an OGTA fusion protein or fragment. If desired, compounds identified in the primary screen can then be assayed in a secondary screen against cells naturally or recombinantly expressing a protein of the invention. The ability of the candidate compound to modulate the production, degradation or post-translational modification of an OGTA isoform, an OGTA homologue, an OGTA-related polypeptide or an OGTA fusion protein can be determined by methods known to those of skill in the art, including without limitation, flow cytometry, a scintillation assay, immunoprecipitation and western blot analysis.

In another embodiment, agents that competitively interact with (i.e., bind to) a protein of the invention, a fragment thereof, an OGTA-related polypeptide, a fragment of an OGTA-related polypeptide, or an OGTA fusion protein are identified in a competitive binding assay. In accordance with this embodiment, cells expressing a protein of the invention, an OGTA fragment, an OGTA-related polypeptide, a fragment of an OGTA-related polypeptide, or an OGTA fusion protein are contacted with a candidate compound and a compound known to interact with a protein of the invention, an OGTA fragment, an OGTA-related polypeptide, a fragment of an OGTA-related polypeptide or an OGTA fusion protein; the ability of the candidate compound to preferentially interact with a protein of the invention, an OGTA fragment, an OGTA-related polypeptide, a fragment of an OGTA-related polypeptide, or an OGTA fusion protein is then determined. Alternatively, agents that preferentially interact with (i.e., bind to) a protein of the invention, an OGTA fragment, an OGTA-related polypeptide or fragment of an OGTA-related polypeptide are identified in a cell-free assay system by contacting a protein of the invention, an OGTA fragment, an OGTA-related polypeptide, a fragment of an OGTA-related polypeptide, or an OGTA fusion protein with a candidate compound and a compound known to interact with a protein of the invention, an OGTA-related polypeptide or an OGTA fusion protein. As stated above, the ability of the candidate compound to interact with a protein of the invention, an OGTA fragment, an OGTA-related polypeptide, a fragment of an OGTA-related polypeptide, or an OGTA fusion protein can be determined by methods known to those of skill in the art. These assays, whether cell-based or cell-free, can be used to screen a plurality (e.g., a library) of candidate compounds.

In another embodiment, agents that modulate (i.e., upregulate or downregulate) the expression or activity of a protein of the invention, or an OGTA-related polypeptide are identified by contacting cells (e.g., cells of prokaryotic origin or eukaryotic origin) expressing a protein of the invention, or an OGTA-related polypeptide with a candidate compound or a control compound (e.g., phosphate buffered saline (PBS)) and determining the expression of a protein of the invention, an OGTA-related polypeptide, or an OGTA fusion protein, mRNA encoding a protein of the invention, or mRNA encoding an OGTA-related polypeptide. The level of expression of a protein of the invention, an OGTA-related polypeptide, mRNA encoding a protein of the invention, or mRNA encoding an OGTA-related polypeptide in the presence of the candidate compound is compared to the level of expression of a protein of the invention, an OGTA-related polypeptide, mRNA encoding a protein of the invention, or mRNA encoding an OGTA-related polypeptide in the absence of the candidate compound (e.g., in the presence of a control compound). The candidate compound can then be identified as a modulator of the expression of a protein of the invention, or the OGTA-related polypeptide based on this comparison. For example, when expression of a protein of the invention or mRNA is significantly greater in the presence of the candidate compound than in its absence, the candidate compound is identified as a stimulator of expression of a protein of the invention or mRNA. Alternatively, when expression of a protein of the invention or mRNA is significantly less in the presence of the candidate compound than in its absence, the candidate compound is identified as an inhibitor of the expression of a protein of the invention or mRNA. The level of expression of a protein of the invention or the mRNA that encodes it can be determined by methods known to those of skill in the art. For example, mRNA expression can be assessed by Northern blot analysis or RT-PCR, and protein levels can be assessed by western blot analysis.

In another embodiment, agents that modulate the activity of a protein of the invention or an OGTA-related polypeptide are identified by contacting a preparation containing a protein of the invention or an OGTA-related polypeptide or cells (e.g., prokaryotic or eukaryotic cells) expressing a protein of the invention or an OGTA-related polypeptide with a test compound or a control compound and determining the ability of the test compound to modulate (e.g., stimulate or inhibit) the activity of a protein of the invention or an OGTA-related polypeptide. The activity of a protein of the invention or an OGTA-related polypeptide can be assessed by detecting induction of a cellular signal transduction pathway of a protein of the invention or an OGTA-related polypeptide (e.g., intracellular $Ca^{2+}$, diacylglycerol, IP3, etc.), detecting catalytic or enzymatic activity of the target on a suitable substrate, detecting the induction of a reporter gene (e.g., a regulatory element that is responsive to a protein of the invention or an OGTA-related polypeptide and is operably linked to a nucleic acid encoding a detectable marker, e.g., luciferase), or detecting a cellular response, for example, cellular differentiation, or cell proliferation. Based on the present description, techniques known to those of skill in the art can be used for measuring these activities (see, e.g., U.S. Pat. No. 5,401,639, which is incorporated herein by reference). The candidate compound can then be identified as a modulator of the activity of a protein of the invention or an OGTA-related polypeptide by comparing the effects of the candidate compound to the control compound. Suitable control compounds include phosphate buffered saline (PBS) and normal saline (NS).

In another embodiment, agents that modulate (i.e., upregulate or downregulate) the expression, activity or both the expression and activity of a protein of the invention or an OGTA-related polypeptide are identified in an animal model. Examples of suitable animals include, but are not limited to, mice, rats, rabbits, monkeys, guinea pigs, dogs and cats. Preferably, the animal used represent a model of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer (e.g. xenografts of acute T-cell leukaemia cell lines such as HSB-2 in SCID mice, Morland et al, Cell Biophys. 1994;24-25:315-29; xenografts of B-cell non-Hodgkin's lymphoma cell lines such as SU-DHL-4 and OCI-Ly8 in SCID mice, Schmidt-Wolf et al, J Exp Med. 1991 Jul. 1; 174(1):139-49; xenografts of breast cancer cell lines such as MCF-7 (Ozzello L, Sordat M., Eur J Cancer. 1980; 16:553-559) and MCF10AT (Miller et al., J Natl Cancer Inst. 1993;85:1725-1732) in nude or SCID mice; xenografts of human colorectal cancer cell lines such as MDA-MB-345 in oestrogen-deprived SCID mice, Eccles et al. 1994 Cell Biophysics 24/25, 279; xenografts of gastric cell lines such as AZ-521 in nude mice; xenografts of hepatocellular carcinoma cell lines such as MHCC97 in nude mice, Tian et al., Br J 5 Cancer 1999 November; 81(5):814-21; xenografts of non small cell lung cancer cell lines such as A549 and H460 and xenografts of small cell lung cancer cell lines such as NCI-H345; xenografts of melanoma cell lines such as MV3 in nude mice, van Muijen et al, Int J Cancer 1991 Apr. 22; 48(1):85-91; xenografts of human osteosarcoma cell lines such as HuO9 in nude mice, Kimura et al., Clin Exp Metastasis 2002; 19(6):477-85; xenografts of ovarian cancer cell lines such as IGROV1 in nude mice, Benard et al, Cancer Res. 1985 October; 45(10):4970-9; xenografts of pancreatic cancer cell lines such as MIA PaCa-2 in nude mice, Marincola et al., J Surg Res 1989 December; 47(6):520-9; xenografts of prostate cancer cell lines such as CWR-22 in nude mice, Pretlow et al, J Natl Cancer Inst. 1993 Mar. 3; 85(5):394-8 or xenografts of renal cell cancer cell lines such as LABAZ1 in immune compromised mice, Zisman et al, Cancer Research 63, 4952-4959, Aug. 15, 2003.). These can be utilized to test compounds that modulate levels of a protein of the invention, since the pathology exhibited in these models is similar to that of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer. In accordance with this embodiment, the test compound or a control compound is administered (e.g., orally, rectally or parenterally such as intraperitoneally or intravenously) to a suitable animal and the effect on the expression, activity or both expression and activity of a protein of the invention or OGTA-related polypeptide is determined. Changes in the expression of a protein of the invention or an OGTA-related polypeptide can be assessed by the methods outlined above.

In yet another embodiment, a protein of the invention or an OGTA-related polypeptide is used as a "bait protein" in a two-hybrid assay or three hybrid assay to identify other proteins that bind to or interact with a protein of the invention or an OGTA-related polypeptide (see, e.g., U.S. Pat. No. 5,283, 317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and PCT Publication No. WO 94/10300). As those skilled in the art will appreciate, such binding proteins are also likely to be involved in the propagation of signals by a protein of the invention as, for example, upstream or downstream elements of a signaling pathway involving a protein of the invention.

This invention further provides novel agents identified by the above-described screening assays and uses thereof for treatments as described herein. In addition, the invention also provides the use of an agent which interacts with, or modulates the activity of, a protein of the invention in the manufacture of a medicament for the treatment of a relevant cancer.

Therapeutic Use of the Proteins of the Invention

The invention provides for treatment or prevention of various diseases and disorders by administration of a therapeutic compound. Such compounds include but are not limited to: proteins of the invention, OGTA analogs, OGTA-related polypeptides and derivatives (including fragments) thereof; antibodies (or other affinity reagents) to the foregoing; nucleic acids encoding proteins of the invention, OGTA analogs, OGTA-related polypeptides and fragments thereof; antisense nucleic acids to a gene encoding a protein of the invention or an OGTA-related polypeptide; and modulator (e.g., agonists and antagonists) of a gene encoding a protein of the invention or an OGTA-related polypeptide. An important feature of the present invention is the identification of genes encoding a protein of the invention involved in B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer. B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer can be treated (e.g. to ameliorate symptoms or to retard onset or progression) or prevented by administration of a therapeutic compound that reduces function or expression of a protein of the invention in the serum or tissue of subjects having a relevant cancer.

In one embodiment, one or more antibodies (or other affinity reagents) each specifically binding to a protein of the invention are administered alone or in combination with one or more additional therapeutic compounds or treatments.

Preferably, a biological product such as an antibody (or other affinity reagent) is allogeneic to the subject to which it is administered. In a preferred embodiment, a human protein of the invention or a human OGTA-related polypeptide, a nucleotide sequence encoding a human protein of the invention or a human OGTA-related polypeptide, or an antibody (or other affinity reagent) to a human protein of the invention or a human OGTA-related polypeptide, is administered to a human subject for therapy (e.g. to ameliorate symptoms or to retard onset or progression) or prophylaxis.

Treatment and Prevention of B-Cell Non-Hodgkin's Lymphoma, Breast Cancer, Colorectal Cancer, Gastric Cancer, Hepatocellular Carcinoma, Lung Cancer, Lymphoid Leukaemia (Particularly Acute T-Cell Leukaemia), Melanoma, Osteosarcoma, Ovarian Cancer, Pancreatic Cancer, Prostate Cancer and Renal Cell Cancer B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer are treated or prevented by administration to a subject suspected of having or known to have a relevant cancer or to be at risk of developing a relevant cancer of a compound that modulates (i.e., increases or decreases) the level or activity (i.e. function) of a protein of the invention that is differentially present in the serum or tissue of subjects having a relevant cancer compared with serum or tissue of subjects free from said cancer. In one embodiment, a relevant cancer is treated or prevented by administering to a subject suspected of having or known to have said cancer or to be at risk of developing said cancer a compound that upregulates (i.e., increases) the level or activity (i.e., function) of a protein of the invention that is decreased in the serum or tissue of subjects having said cancer. Examples of such a compound include, but are not limited to, OGTA antisense oligonucleotides, ribozymes, antibodies (or other affinity reagents) directed against OGTA, and compounds that inhibit the enzymatic activity of OGTA. Other useful compounds e.g. OGTA antagonists and small molecule OGTA antagonists, can be identified using in vitro assays.

B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer are also treated or prevented by administration to a subject suspected of having or known to have a relevant cancer or to be at risk of developing said cancer of a compound that downregulates the level or activity (i.e. function) of a protein of the invention that is increased in the serum or tissue of subjects having said cancer. Examples of such a compound include but are not limited to: a protein of the invention, OGTA fragments and OGTA-related polypeptides; nucleic acids encoding a protein of the invention, an OGTA fragment and an OGTA-related polypeptide (e.g., for use in gene therapy); and, for those OGTA or OGTA-related polypeptides with enzymatic activity, compounds or molecules known to modulate that enzymatic activity. Other compounds that can be used, e.g., a protein of the invention agonists, can be identified using in vitro assays.

In a preferred embodiment, therapy or prophylaxis is tailored to the needs of an individual subject. Thus, in specific embodiments, compounds that promote the level or function of a protein of the invention are therapeutically or prophylactically administered to a subject suspected of having or known to have a relevant cancer, in whom the levels or functions of a protein of the invention are absent or are decreased relative to a control or normal reference range. In further embodiments, compounds that promote the level or function of a protein of the invention are therapeutically or prophylactically administered to a subject suspected of having or known to have a relevant cancer in whom the levels or functions of a protein of the invention are increased relative to a control or to a reference range. In further embodiments, compounds that decrease the level or function of a protein of the invention are therapeutically or prophylactically administered to a subject suspected of having or known to have a relevant cancer in whom the levels or functions of a protein of the invention are increased relative to a control or to a reference range. In further embodiments, compounds that decrease the level or function of a protein of the invention are therapeutically or prophylactically administered to a subject suspected of having or known to have a relevant cancer in whom the levels or functions of a protein of the invention are decreased relative to a control or to a reference range. The change in a protein of the invention function or level due to the administration of such compounds can be readily detected, e.g., by obtaining a sample (e.g., blood or urine) and assaying in vitro the levels or activities of a protein of the invention, or the levels of mRNAs encoding a protein of the invention, or any combination of the foregoing. Such assays can be performed before and after the administration of the compound as described herein.

The compounds of the invention include but are not limited to any compound, e.g. a small organic molecule, protein, peptide, antibody (or other affinity reagent), nucleic acid, etc. that restores the OGTA profile towards normal. The compounds of the invention may be given in combination with any other chemotherapy drugs.

Vaccine Therapy

Another aspect of the invention is an immunogenic composition, suitably a vaccine composition, comprising a protein of the invention or an epitope containing fragment thereof, or nucleic acid encoding a protein of the invention or a fragment thereof optionally together with an immunostimulant.

There is also provided a method of raising an immune response which comprises administering to a subject such compositions and a method for treating or preventing a relevant cancer which comprises administering to a subject in need thereof a therapeutically effective amount of such compositions and such compositions for use in preventing or treating a relevant cancer.

Thus, proteins of the invention may be useful as antigenic material, and may be used in the production of vaccines for treatment or prophylaxis of a relevant cancer. Such material can be "antigenic" and/or "immunogenic". Generally, "antigenic" is taken to mean that the protein is capable of being used to raise antibodies (or other affinity reagents) or indeed is capable of inducing an antibody response in a subject or experimental animal. "Immunogenic" is taken to mean that the protein is capable of eliciting a protective immune response in a subject or experimental animal. Thus, in the latter case, the protein may be capable of not only generating an antibody response but, in addition, non-antibody based immune responses. "Immunogenic" also embraces whether the protein may elicit an immune-like response in an in-vitro setting e.g. a T-cell proliferation assay.

The skilled person will appreciate that homologues or derivatives of proteins of the invention will also find use as antigenic/immunogenic material and for other applications according to the invention. Thus, for instance proteins which include one or more additions, deletions, substitutions or the like are encompassed by the present invention. In addition, it may be possible to replace one amino acid with another of similar "type", for instance, replacing one hydrophobic amino acid with another. One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein as described herein is less important than that the homologue or derivative should retain its antigenicity and/or immunogenicity. However, suitably, homologues or derivatives having at least 60% similarity (as discussed above) or identity with the proteins or polypeptides described herein are provided. Preferably, homologues or derivatives having at least 70% similarity or identity, more preferably at least 75% or 80% similarity or identity are provided. Most preferably, homologues or derivatives having at least 90% or even 95% similarity or identity are provided.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

It is well known that it is possible to screen an antigenic protein or polypeptide to identify epitopic regions, i.e. those regions which are responsible for the protein or polypeptide's antigenicity or immunogenicity. Methods well known to the skilled person can be used to test fragments and/or homologues and/or derivatives for antigenicity. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties of the protein from which it is derived.

What is important for homologues, derivatives and fragments is that they possess at least a degree of the antigenicity/immunogenicity of the protein or polypeptide from which they are derived. Thus, in an additional aspect of the invention, there is provided antigenic/or immunogenic fragments of the proteins of the invention, or of homologues or derivatives thereof.

The proteins of the invention or antigenic fragments thereof, can be provided alone, as a purified or isolated preparation. They may be provided as part of a mixture with one or more other proteins of the invention, or antigenic fragments thereof. In a further aspect, therefore, the invention provides an antigen composition comprising a protein of the invention and/or one or more antigenic fragments thereof. Such a composition can be used for the detection and/or diagnosis of a relevant cancer.

Vaccine compositions according to the invention may be either a prophylactic or therapeutic vaccine composition.

The vaccine compositions of the invention can include one or more adjuvants (immunostimulants). Examples well-known in the art include inorganic gels, such as aluminium hydroxide, and water-in-oil emulsions, such as incomplete Freund's adjuvant. Other useful adjuvants will be well known to the skilled person.

Such preparations may include other vehicles.

In another embodiment, a preparation of oligonucleotides comprising 10 or more consecutive nucleotides complementary to a nucleotide sequence encoding a protein of the invention or an OGTA peptide fragment is used as vaccines for the treatment of a relevant cancer. Such preparations may include adjuvants or other vehicles.

In another aspect, the present invention provides a method of detecting and/or diagnosing a relevant cancer which comprises:

bringing into contact with a sample to be tested an antigenic protein of the invention, or an antigenic fragment thereof, or an antigen composition of the invention; and detecting the presence of antibodies (or other affinity reagents) to said cancer.

In particular, the protein, antigenic fragment thereof or antigen composition of the present invention can be used to detect IgA, IgM or IgG antibodies. Suitably, the sample to be tested will be a biological sample, e.g. a sample of blood or saliva.

In a further aspect, the invention provides the use of an antigenic protein of the invention, antigenic fragment thereof or an antigenic composition of the present invention in detecting and/or diagnosing a relevant cancer. Preferably, the detecting and/or diagnosing are carried out in vitro.

The antigenic protein of the invention, antigenic fragments thereof or antigenic composition of the present invention can be provided as a kit for use in the in vitro detection and/or diagnosis of a relevant cancer. Thus, in a still further aspect, the present invention provides a kit for use in the detection and/or diagnosis of a relevant cancer, which kit comprises an antigenic protein of the invention, an antigenic fragment thereof or an antigenic composition of the present invention.

In addition, the antigenic protein of the invention, antigenic fragment thereof or antigen composition of the invention can be used to induce an immune response against a relevant cancer. Thus, in a yet further aspect, the invention provides the use of an antigenic protein of the invention, an antigenic fragment thereof or an antigen composition of the invention in medicine.

In a further aspect, the present invention provides a composition capable of eliciting an immune response in a subject, which composition comprises a protein of the invention, an antigenic fragment thereof, or an antigen composition of the invention. Suitably, the composition will be a vaccine composition, optionally comprising one or more suitable adjuvants. Such a vaccine composition may be either a prophylactic or therapeutic vaccine composition.

In yet further aspects, the present invention provides:
(a) the use of a protein of the invention, an antigenic fragment thereof, or an antigen composition of the invention in the preparation of an immunogenic composition, preferably a vaccine;
(b) the use of such an immunogenic composition in inducing an immune response in a subject; and
(c) a method for the treatment or prophylaxis of a relevant cancer in a subject, or of vaccinating a subject against a relevant cancer which comprises the step of administering to the subject an effective amount of a protein of the invention, at least one antigenic fragment thereof or an antigen composition of the invention, preferably as a vaccine.

In a specific embodiment, a preparation of a protein of the invention or OGTA peptide fragments is used as a vaccine for the treatment of a relevant cancer. Such preparations may include adjuvants or other vehicles.

In another embodiment, a preparation of oligonucleotides comprising 10 or more consecutive nucleotides complementary to a nucleotide sequence encoding a protein of the invention or an OGTA peptide fragment is used as vaccines for the treatment of a relevant cancer. Such preparations may include adjuvants or other vehicles.

Inhibition of the Proteins of the Invention to Treat B-cell Non-Hodgkin's Lymphoma, Breast Cancer, Colorectal Cancer, Gastric Cancer, Hepatocellular Carcinoma, Lung Cancer, Lymphoid Leukaemia (Particularly Acute T-cell Leukaemia), Melanoma, Osteosarcoma, Ovarian Cancer, Pancreatic Cancer, Prostate Cancer and Renal Cell Cancer In one embodiment of the invention, a relevant cancer is treated or prevented by administration of a compound that antagonizes (inhibits) the level(s) and/or function(s) of a protein of the invention which are elevated in the serum or tissue of subjects having a relevant cancer as compared with serum or tissue of subjects free from said cancer Compounds useful for this purpose include but are not limited to anti-OGTA014, anti-OGTA020, anti-OGTA067, anti-OGTA116 or anti-OGTA194 antibodies (or other affinity reagents, and fragments and derivatives containing the binding region thereof), OGTA antisense or ribozyme nucleic acids, and nucleic acids encoding dysfunctional OGTA that are used to "knockout" endogenous OGTA function by homologous recombination (see, e.g., Capecchi, 1989, *Science* 244:1288-1292). Other compounds that inhibit OGTA function can be identified by use of known in vitro assays, e.g. assays for the ability of a test compound to inhibit binding of a protein of the invention to another protein or a binding partner, or to inhibit a known OGTA function. Preferably such inhibition is assayed in vitro or in cell culture, but genetic assays may also be employed. The Preferred Technologies can also be used to detect levels of a protein of the invention before and after the administration of the compound. Preferably, suitable in vitro or in vivo assays are utilized to determine the effect of a specific compound and whether its administration is indicated for treatment of the affected tissue, as described in more detail below.

In a specific embodiment, a compound that inhibits OGTA function is administered therapeutically or prophylactically to a subject in whom an increased serum or tissue level or functional activity of a protein of the invention (e.g. greater than the normal level or desired level) is detected as compared with serum or tissue of subjects free from said cancer or a predetermined reference range. Methods standard in the art can be employed to measure the increase in a level or function of a protein of the invention, as outlined above. Preferred OGTA inhibitor compositions include small molecules, i.e. molecules of 1000 daltons or less. Such small molecules can be identified by the screening methods described herein.

Assays for Therapeutic or Prophylactic Compounds

The present invention also provides assays for use in drug discovery in order to identify or verify the efficacy of compounds for treatment or prevention of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer. Test compounds can be assayed for their ability to restore OGTA levels in a subject having a relevant cancer towards levels found in subjects free from said cancer or to produce similar changes in experimental animal models of said cancer. Compounds able to restore OGTA levels in a subject having a relevant cancer towards levels found in subjects free from said cancer or to produce similar changes in experimental animal models of said cancer can be used as lead compounds for further drug discovery, or used therapeutically. OGTA expression can be assayed by the Preferred Technologies, immunoassays, gel electrophoresis followed by visualization, detection of OGTA activity, or any other method taught herein or known to those skilled in the art. Such assays can be used to screen candidate drugs, in clinical monitoring or in drug development, where abundance of a protein of the invention can serve as a surrogate marker for clinical disease.

In various specific embodiments, in vitro assays can be carried out with cells representative of cell types involved in a subject's disorder, to determine if a compound has a desired effect upon such cell types.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. Examples of animal models of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer include, but are not limited to xenografts of acute T-cell leukaemia cell lines such as HSB-2 in SCID mice, Morland et al, Cell Biophys. 1994; 24-25:315-29; xenografts of B-cell non-Hodgkin's lymphoma cell lines such as SU-DHL-4 and OCI-Ly8 in SCID mice, Schmidt-Wolf et al, J Exp Med. 1991 Jul. 1; 174(1):139-49; xenografts of breast cancer cell lines such as MCF-7 (Ozzello L, Sordat M., Eur J Cancer. 1980; 16:553-559) and MCF10AT (Miller et al., J Natl Cancer Inst. 1993; 85:1725-1732) in nude or SCID mice; xenografts of human colorectal cancer cell lines such as MDA-MB-345 in oestrogen-deprived SCID mice, Eccles et al. 1994 Cell Biophysics 24/25, 279; xenografts of gastric cell lines such as AZ-521 in nude mice; xenografts of hepatocellular carcinoma cell lines such as MHCC97 in nude mice, Tian et al., Br J 5 Cancer 1999 November; 81(5):814-21; xenografts of non small cell lung cancer cell lines such as A549 and H460 and xenografts of small cell lung cancer cell lines such as NCI-H345; xenografts of melanoma cell lines such as MV3 in nude mice, van Muijen et al, Int J Cancer 1991 Apr. 22; 48(1):85-91; xenografts of human osteosarcoma cell lines such as HuO9 in nude mice, Kimura et al., Clin Exp Metastasis 2002; 19(6):477-85; xenografts of ovarian cancer cell lines such as IGROV1 in nude mice, Benard et al, Cancer Res. 1985 October; 45(10):4970-9; xenografts of pancreatic cancer cell lines such as MIA PaCa-2 in nude mice, Marincola et al., J Surg Res 1989 December; 47(6):520-9; xenografts of prostate cancer cell lines such as CWR-22 in nude mice, Pretlow et al, J Natl Cancer Inst. 1993 Mar. 3; 85(5):394-8 and xenografts of renal cell cancer cell lines such as LABAZ1 in immune compromised mice, Zisman et al, Cancer Research 63, 4952-4959, Aug. 15, 2003. These can be utilized to test compounds that modulate OGTA levels, since the pathology exhibited in these models is similar to that of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer. It is also apparent to the skilled artisan that based upon the present disclosure, transgenic animals can be produced with "knock-out" mutations of the gene or genes encoding a protein of the invention. A "knock-out" mutation of a gene is a mutation that causes the mutated gene to not be expressed, or expressed in an aberrant form or at a low level, such that the activity associated with the gene product is nearly or entirely absent. Preferably, the transgenic animal is a mammal; more preferably, the transgenic animal is a mouse.

In one embodiment, test compounds that modulate the expression of a protein of the invention are identified in non-human animals (e.g. mice, rats, monkeys, rabbits, and guinea pigs), preferably non-human animal models for a relevant cancer, expressing a protein of the invention. In accordance with this embodiment, a test compound or a control compound is administered to the animals, and the effect of the test compound on expression of a protein of the invention is determined. A test compound that alters the expression of a protein of the invention can be identified by comparing the level of a protein of the invention (or mRNA(s) encoding the same) in an animal or group of animals treated with a test compound with the level of a protein of the invention or mRNA(s) in an animal or group of animals treated with a control compound. Techniques known to those of skill in the art can be used to determine the mRNA and protein levels, for example, in situ hybridization. The animals may or may not be sacrificed to assay the effects of a test compound.

In another embodiment, test compounds that modulate the activity of a protein of the invention or a biologically active portion thereof are identified in non-human animals (e.g., mice, rats, monkeys, rabbits, and guinea pigs), preferably non-human animal models for a relevant cancer, expressing a protein of the invention. In accordance with this embodiment, a test compound or a control compound is administered to the animals, and the effect of a test compound on the activity of a protein of the invention is determined. A test compound that alters the activity of a protein of the invention can be identified by assaying animals treated with a control compound and animals treated with the test compound. The activity of a protein of the invention can be assessed by detecting induction of a cellular second messenger of a protein of the invention (e.g., intracellular $Ca^{2+}$, diacylglycerol, IP3, etc.), detecting catalytic or enzymatic activity of a protein of the invention or binding partner thereof, detecting the induction of a reporter gene (e.g., a regulatory element that is responsive to a protein of the invention operably linked to a nucleic acid encoding a detectable marker, such as luciferase or green fluorescent protein), or detecting a cellular response (e.g., cellular differentiation or cell proliferation). Techniques known to those of skill in the art can be utilized to detect changes in the activity of a protein of the invention (see, e.g., U.S. Pat. No. 5,401,639, which is incorporated herein by reference).

In yet another embodiment, test compounds that modulate the level or expression of a protein of the invention are identified in human subjects having a relevant cancer, preferably those having severe cancer. In accordance with this embodiment, a test compound or a control compound is administered to the human subject, and the effect of a test compound on OGTA expression is determined by analyzing the expression of a protein of the invention or the mRNA encoding the same in a biological sample (e.g., serum, plasma, or urine). A test compound that alters the expression of a protein of the invention can be identified by comparing the level of a protein of the invention or mRNA encoding the same in a subject or group of subjects treated with a control compound to that in a subject or group of subjects treated with a test compound. Alternatively, alterations in the expression of a protein of the invention can be identified by comparing the level of a protein of the invention or mRNA encoding the same in a subject or group of subjects before and after the administration of a test compound. Techniques known to those of skill in the art can be used to obtain the biological sample and analyze the mRNA or protein expression. For example, the Preferred Technologies described herein can be used to assess changes in the level of a protein of the invention.

In another embodiment, test compounds that modulate the activity of a protein of the invention are identified in human subjects having a relevant cancer, (preferably those with severe cancer). In this embodiment, a test compound or a control compound is administered to the human subject, and the effect of a test compound on the activity of a protein of the invention is determined. A test compound that alters the activity of a protein of the invention can be identified by comparing biological samples from subjects treated with a control compound to samples from subjects treated with the test compound. Alternatively, alterations in the activity of a protein of the invention can be identified by comparing the activity of a protein of the invention in a subject or group of subjects before and after the administration of a test compound. The activity of a protein of the invention can be assessed by detecting in a biological sample (e.g., serum, plasma, or urine) induction of a cellular signal transduction pathway of a protein of the invention (e.g., intracellular $Ca^{2+}$, diacylglycerol, IP3, etc.), catalytic or enzymatic activity of a protein of the invention or a binding partner thereof, or a cellular response, for example, cellular differentiation, or cell proliferation. Techniques known to those of skill in the art can be used to detect changes in the induction of a second messenger of a protein of the invention or changes in a cellular response. For example, RT-PCR can be used to detect changes in the induction of a cellular second messenger.

In a preferred embodiment, a test compound that changes the level or expression of a protein of the invention towards levels detected in control subjects (e.g. humans free from the relevant cancer) is selected for further testing or therapeutic use. In another preferred embodiment, a test compound that changes the activity of a protein of the invention towards the activity found in control subjects (e.g. humans free from the relevant cancer) is selected for further testing or therapeutic use.

In another embodiment, test compounds that reduce the severity of one or more symptoms associated with a relevant cancer are identified in human subjects having a relevant cancer, preferably subjects with severe cancer. In accordance with this embodiment, a test compound or a control compound is administered to the subjects, and the effect of a test compound on one or more symptoms of a relevant cancer is determined. A test compound that reduces one or more symptoms can be identified by comparing the subjects treated with a control compound to the subjects treated with the test compound. Techniques known to physicians familiar with a relevant cancer can be used to determine whether a test compound reduces one or more symptoms associated with said cancer. For example, a test compound that reduces tumour burden in a subject having a relevant cancer will be beneficial for subjects having said cancer In a preferred embodiment, a test compound that reduces the severity of one or more symptoms associated with a relevant cancer in a human having said cancer is selected for further testing or therapeutic use.

Therapeutic and Prophylactic Compositions and their Use

The invention provides methods of treatment (and prophylaxis) comprising administering to a subject an effective amount of a compound of the invention. In a preferred aspect, the compound is substantially purified (e.g. substantially free from substances that limit its effect or produce undesired side-effects). The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, or fibers. In one embodiment, administration can be by direct injection into lymphoid, breast, colorectal, gastric, liver, lung, skin, osteoblast, ovarian, pancreatic, prostate and kidney tissue or at the site (or former site) of a malignant tumour or neoplastic or pre-neoplastic tissue.

In another embodiment, the compound can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target e.g. the breast, colon, stomach, liver, lung, skin, bone, ovary, pancreas, prostate or kidney thus requiring only a fraction of the systemic dose (see, e.g., Goodson, in Medical Applications of Controlled Release, supra, vol. 2, pp. 115-138 (1984)).

Other controlled release systems are discussed in the review by Langer (1990, Science 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of a relevant cancer can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Determining Abundance of the Proteins of the Invention by Imaging Technology

An advantage of determining abundance of a protein of the invention by imaging technology may be that such a method is non-invasive (save that reagents may need to be administered) and there is no need to extract a sample from the subject.

Suitable imaging technologies include positron emission tomography (PET) and single photon emission computed tomography (SPECT). Visualisation of a protein of the invention using such techniques requires incorporation or binding of a suitable label e.g. a radiotracer such as $^{18}F$, $^{11}C$ or $^{123}I$ (see e.g. NeuroRx—The Journal of the American Society for Experimental NeuroTherapeutics (2005) 2(2), 348-360 and idem pages 361-371 for further details of the techniques). Radiotracers or other labels may be incorporated into a protein of the invention by administration to the subject (e.g. by injection) of a suitably labelled specific ligand. Alternatively they may be incorporated into a binding affinity reagent (e.g. antibody) specific for a protein of the invention which may be administered to the subject (e.g. by injection). For discussion of use of Affibodies for imaging see e.g. Orlova A, Magnusson M, Eriksson T L, Nilsson M, Larsson B, Hoiden-Guthenberg I, Widstrom C, Carlsson J, Tolmachev V, Stahl S, Nilsson F Y, Tumour imaging using a picomolar affinity HER2 binding affibody molecule, Cancer Res. 2006 Apr. 15; 66(8): 4339-48).

Diagnosis and Treatment of B-Cell Non-Hodgkin's Lymphoma, Breast Cancer, Colorectal Cancer, Gastric Cancer, Hepatocellular Carcinoma, Lung Cancer, Lymphoid Leukaemia (Particularly Acute T-cell Leukaemia), Melanoma, Osteosarcoma, Ovarian Cancer, Pancreatic Cancer, Prostate Cancer and Renal Cell Cancer Using Immunohistochemistry Immunohistochemistry is an excellent detection technique and may therefore be very useful in the diagnosis and treatment of a relevant cancer. Immunohistochemistry may be used to detect, diagnose, or monitor a relevant cancer through the localization of OGTA antigens in tissue sections by the use of labeled antibodies (or other affinity reagents), derivatives and analogs thereof, which specifically bind to the proteins of the invention, as specific reagents through antigen-antibody interactions that are visualized by a marker such as fluorescent dye, enzyme, radioactive element or colloidal gold.

The advancement of monoclonal antibody technology has been of great significance in assuring the place of immunohistochemistry in the modern accurate microscopic diagnosis of human neoplasms. The identification of disseminated neoplastically transformed cells by immunohistochemistry allows for a clearer picture of cancer invasion and metastasis, as well as the evolution of the tumour cell associated immunophenotype towards increased malignancy. Future antineoplastic therapeutical approaches may include a variety of individualized immunotherapies, specific for the particular immunophenotypical pattern associated with each individual patient's neoplastic disease. For further discussion see e.g. Bodey B, The significance of immunohistochemistry in the diagnosis and therapy of neoplasms, Expert Opin Biol Ther. 2002 April; 2(4):371-93.

In one or more aspects the invention does not extent to a sequence of Sequence ID No. 6, 26, 34, 60, 70, 77, 82 and/or 91.

Features of each aspect of the invention are as for each of the other aspects mutatis mutandis. The prior art documents mentioned herein are incorporated to the fullest extent permitted by law.

EXAMPLE 1

Identification of Membrane Proteins Expressed in B-Cell Non-Hodgkin's Lymphoma, Breast Cancer, Colorectal Cancer, Gastric Cancer, Hepatocellular Carcinoma, Lung Cancer, Lymphoid Leukaemia (Particulary Acute T-Cell Leukaemia), Melanoma, Osteosarcoma, Ovarian Cancer, Pancreatic Cancer, Prostate Cancer and Renal Cell Cancer Blood and Tissue Samples Using 1D Gel Electrophoresis Using the following Reference Protocol, membrane proteins extracted from B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer tissue samples were separated by 1D gel and analysed.

1.1 Materials and Methods 1.1.1—Plasma Membrane Fractionation

The cells recovered from a B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer or renal cell cancer were lysed and submitted to centrifugation at 1000 G. The supernatant was taken, and it was subsequently centrifuged at 3000 G. Once again, the supernatant was taken, and it was then centrifuged at 100 000 G.

The resulting pellet was recovered and put on 15-60% sucrose gradient.

A Western blot was used to identify sub cellular markers, and the Plasma Membrane fractions were pooled.

The pooled solution was either run directly on 1D gels (see section 1.1.4 below), or further fractionated into heparin binding and nucleotide binding fractions as described below.

1.1.2—Plasma Membrane Heparin-binding Fraction

The pooled solution from 1.1.1 above was applied to a Heparin column, eluted from column and run on 1D gels (see section 1.1.4 below).

1.1.3—Plasma Nucleotide-binding Fraction

The pooled solution from 1.1.1 above was applied to a Cibacrom Blue 3GA column, eluted from column and run on 1D gels (see section 1.1.4 below).

1.1.4-1D Gel Technology

Protein or membrane pellets were solubilised in 1D sample buffer (1-2 µg/µl). The sample buffer and protein mixture was then heated to 95° C. for 3 min.

A 9-16% acrylamide gradient gel was cast with a stacking gel and a stacking comb according to the procedure described in Ausubel F. M. et al., eds., 1989, Current Protocols in Molecular Biology, Vol. II, Green Publishing Associates, Inc., and John Wiley & Sons, Inc., New York, section 10.2, incorporated herein by reference in its entirety.

30-50 micrograms of the protein mixtures obtained from detergent and the molecular weight standards (66, 45, 31, 21, 14 kDa) were added to the stacking gel wells using a 10 microliter pipette tip and the samples run at 40 mA for 5 hours.

The plates were then prised open, the gel placed in a tray of fixer (10% acetic acid, 40% ethanol, 50% water) and shaken overnight. Following this, the gel was primed by 30 minutes shaking in a primer solution (7.5% acetic acid (75 ml), 0.05% SDS (5 ml of 10%)). The gel was then incubated with a fluorescent dye (7.5% acetic acid, 0.06% OGS in-house dye (600 µl) with shaking for 3 hrs. Sypro Red (Molecular Probes, Inc., Eugene, Oreg.) is a suitable dye for this purpose. A preferred fluorescent dye is disclosed in U.S. application Ser. No. 09/412,168, filed on Oct. 5, 1999, which is incorporated herein by reference in its entirety.

A computer-readable output was produced by imaging the fluorescently stained gels with an Apollo 3 scanner (Oxford Glycosciences, Oxford, UK). This scanner is developed from the scanner described in WO 96/36882 and in the Ph.D. thesis of David A. Basiji, entitled "Development of a High-throughput Fluorescence Scanner Employing Internal Reflection Optics and Phase-sensitive Detection (Total Internal Reflection, Electrophoresis)", University of Washington (1997), Volume 58/12-B of Dissertation Abstracts International, page 6686, the contents of each of which are incorporated herein by reference. The latest embodiment of this instrument includes the following improvements: The gel is transported through the scanner on a precision lead-screw drive system. This is preferable to laying the glass plate on the belt-driven system that is defined in the Basiji thesis as it provides a reproducible means of accurately transporting the gel past the imaging optics.

The gel is secured into the scanner against three alignment stops that rigidly hold the glass plate in a known position. By doing this in conjunction with the above precision transport system and the fact that the gel is bound to the glass plate, the absolute position of the gel can be predicted and recorded. This ensures that accurate co-ordinates of each feature on the gel can be communicated to the cutting robot for excision. This cutting robot has an identical mounting arrangement for the glass plate to preserve the positional accuracy.

The carrier that holds the gel in place has integral fluorescent markers (Designated M1, M2, and M3) that are used to correct the image geometry and are a quality control feature to confirm that the scanning has been performed correctly.

The optical components of the system have been inverted. The laser, mirror, waveguide and other optical components are now above the glass plate being scanned. The embodiment of the Basiji thesis has these underneath. The glass plate is therefore mounted onto the scanner gel side down, so that the optical path remains through the glass plate. By doing this, any particles of gel that may break away from the glass plate will fall onto the base of the instrument rather than into the optics.

In scanning the gels, they were removed from the stain, rinsed with water and allowed to air dry briefly and imaged on the Apollo 3. After imaging, the gels were sealed in polyethylene bags containing a small volume of staining solution, and then stored at 4° C.

Apparent molecular weights were calculated by interpolation from a set of known molecular weight markers run alongside the samples.

1.1.5—Recovery and Analysis of Selected Proteins

Proteins were robotically excised from the gels by the process described in U.S. Pat. No. 6,064,754, Sections 5.4 and 5.6, 5.7, 5.8 (incorporated herein by reference), as is applicable to 1D-electrophoresis, with modification to the robotic cutter as follows: the cutter begins at the top of the lane, and cuts a gel disc 1.7 mm in diameter from the left edge of the lane. The cutter then moves 2 mm to the right, and 0.7 mm down and cuts a further disc. This is then repeated. The cutter then moves back to a position directly underneath the first gel cut, but offset by 2.2 mm downwards, and the pattern of three diagonal cuts are repeated. This is continued for the whole length of the gel.

NOTE: If the lane is observed to broaden significantly then a correction can be made also sideways i.e. instead of returning to a position directly underneath a previous gel cut, the cut can be offset slightly to the left (on the left of the lane) and/or the right (on the right of the lane). The proteins contained within the gel fragments were processed to generate tryptic peptides; partial amino acid sequences of these peptides were determined by mass spectroscopy as described in WO98/53323 and application Ser. No. 09/094,996, filed Jun. 15, 1998.

Proteins were processed to generate tryptic digest peptides. Tryptic peptides were analyzed by mass spectrometry using a PerSeptive Biosystems Voyager-DETM STR Matrix-Assisted Laser Desorption Ionization Time-of-Flight (MALDI-TOF) mass spectrometer, and selected tryptic peptides were analyzed by tandem mass spectrometry (MS/MS) using a Micromass Quadrupole Time-of-Flight (Q-TOF) mass spectrometer (Micromass, Altrincham, U.K.) equipped with a nanoflow™ electrospray Z-spray source. For partial amino acid sequencing and identification of OGTA014, OGTA020, OGTA067, OGTA116 and OGTA194, uninterpreted tandem mass spectra of tryptic peptides were searched using the SEQUEST search program (Eng et al., 1994, J. Am. Soc. Mass Spectrom. 5:976-989), version v.C.1. Criteria for database identification included: the cleavage specificity of trypsin; the detection of a suite of a, b and y ions in peptides returned from the database, and a mass increment for all Cys residues to account for carbamidomethylation. The database searched was a database constructed of protein entries in the non-redundant database held by the National Centre for Biotechnology Information (NCBI) which is accessible at www.ncbi.nlm.nih.gov. Following identification of proteins through spectral-spectral correlation using the SEQUEST program, masses detected in MALDI-TOF mass spectra were assigned to tryptic digest peptides within the proteins identified. In cases where no amino acid sequences could be identified through searching with uninterpreted MS/MS spectra of tryptic digest peptides using the SEQUEST program, tandem mass spectra of the peptides were interpreted manually, using methods known in the art. (In the case of interpretation of low-energy fragmentation mass spectra of peptide ions see Gaskell et al., 1992, Rapid Commun. Mass Spectrom. 6:658-662).

1.1.6—Discrimination of B-cell Non-Hodgkin's Lymphoma, Breast Cancer, Colorectal Cancer, Gastric Cancer, Hepatocellular Carcinoma, Lung Cancer, Lymphoid Leukaemia (Particularly Acute T-cell Leukaemia), Melanoma, Osteosarcoma, Ovarian Cancer, Pancreatic Cancer, Prostate Cancer and Renal Cell Cancer Associated Proteins The process to identify OGTA014, OGTA020, OGTA067, OGTA116 and OGTA194 the peptide sequences obtained experimentally by mass spectrometry described above of naturally occurring human proteins to identify and organize coding exons in the published human genome sequence.

Recent dramatic advances in defining the chemical sequence of the human genome have led to the near completion of this immense task (Venter, J. C. et al. (2001). The sequence of the human genome. Science 16: 1304-51; International Human Genome Sequencing Consortium. (2001). Initial sequencing and analysis of the human genome Nature 409: 860-921). There is little doubt that this sequence information will have a substantial impact on our understanding of many biological processes, including molecular evolution, comparative genomics, pathogenic mechanisms and molecular medicine. For the full medical value inherent in the sequence of the human genome to be realised, the genome needs to be 'organised' and annotated. By this, is meant at least the following three things: (i) The assembly of the sequences of the individual portions of the genome into a coherent, continuous sequence for each chromosome. (ii) The unambiguous identification of those regions of each chromosome that contain genes. (iii) Determination of the fine structure of the genes and the properties of its mRNA and protein products. While the definition of a "gene" is an increasingly complex issue (H Pearson: What is a gene? Nature (2006) 24: 399-401), what is of immediate interest for drug discovery and development is a catalogue of those genes that encode functional, expressed proteins. A subset of these genes will be involved in the molecular basis of most if not all pathologies. Therefore an important and immediate goal for the pharmaceutical industry is to identify all such genes in the human genome and describe their fine structure.

Processing and Integration of Peptide Masses, Peptide Signatures, ESTs and Public Domain Genomic Sequence Data to form OGAP® Database Discrete genetic units (exons, transcripts and genes) were identified using the following sequential steps:

1. A 'virtual transcriptome' is generated, containing the tryptic peptides which map to the human genome by combining the gene identifications available from Ensembl and various gene prediction programs. This also incorporates SNP data (from dbSNP) and all alternate splicing of gene identifications. Known contaminants were also added to the virtual transcriptome.
2. All tandem spectra in the OGeS Mass Spectrometry Database are interpreted in order to produce a peptide that can be mapped to one in the virtual transcriptome. A set of automated spectral interpretation algorithms were used to produce the peptide identifications.
3. The set of all mass-matched peptides in the OGeS Mass Spectrometry Database is generated by searching all peptides from transcripts hit by the tandem peptides using a tolerance based on the mass accuracy of the mass spectrometer, typically 20 ppm.
4. All tandem and mass-matched peptides are combined in the form of "protein clusters". This is done using a recursive process which groups sequences into clusters based on common peptide hits. Biological sequences are considered to belong to the same cluster if they share one or more tandem or mass-matched peptide.

5. After initial filtering to screen out incorrectly identified peptides, the resulting clusters are then mapped on the human genome.
6. The protein clusters are then aggregated into regions that define preliminary gene boundaries using their proximity and the co-observation of peptides within protein clusters. Proximity is defined as the peptide being within 80,000 nucleotides on the same strand of the same chromosome. Various elimination rules, based on cluster observation scoring and multiple mapping to the genome are used to refine the output. The resulting "confirmed genes" are those which best account for the peptides and masses observed by mass spectrometry in each cluster. Nominal co-ordinates for the gene are also an output of this stage.
7. The best set of transcripts for each confirmed gene are created from the protein clusters, peptides, ESTs, candidate exons and molecular weight of the original protein spot.
8. Each identified transcript was linked to the sample providing the observed peptides.
9. Use of an application for viewing and mining the data. The result of steps 1-8 was a database containing genes, each of which consisted of a number of exons and one or more transcripts. An application was written to display & search this integrated genome/proteome data. Any features (OMIM disease locus, InterPro etc.) that had been mapped to the same Golden Path co-ordinate system by Ensembl could be cross-referenced to these genes by coincidence of location and fine structure.

Results

The process was used to generate approximately 1 million peptide sequences to identify protein-coding genes and their exons resulted in the identification of protein sequences for 18083 genes across 67 different tissues and 57 diseases including 2,025 genes in acute T-cell leukaemia, 501 genes in B-cell non-Hodgkin's lymphoma, 4,713 genes in breast cancer, 949 genes in colorectal cancer, 524 genes in gastric cancer, 1,782 genes in hepatocellular carcinoma, 978 genes in lung cancer, 373 genes in lymphoid leukaemia (unspecified), 1,764 genes in melanoma, 1,324 genes in osteosarcoma, 1,033 genes in ovarian cancer, 2,961 genes in pancreatic cancer, 3,307 genes in prostate cancer and 1005 genes in renal cell cancer, illustrated here by OGTA014, OGTA020, OGTA067, OGTA116 and OGTA194 isolated and identified from B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer samples. Following comparison of the experimentally determined sequences with sequences in the OGAP® database, OGTA014, OGTA020, OGTA067, OGTA116 and OGTA194 showed a high degree of specificity to one or more of B-cell non-Hodgkin's lymphoma, breast cancer, colorectal cancer, gastric cancer, hepatocellular carcinoma, lung cancer, lymphoid leukaemia (particularly acute T-cell leukaemia), melanoma, osteosarcoma, ovarian cancer, pancreatic cancer, prostate cancer and renal cell cancer indicative of the prognostic and diagnostic nature.

1.2 Results

These experiments identified OGTA014, OGTA020, OGTA067, OGTA116 and OGTA194, as further described herein.

The full-length OGTA014 was detected in the plasma membrane of B-cell non-Hodgkin's lymphoma, breast cancer, colorectal cancer, hepatocellular carcinoma, lung cancer, lymphoid leukaemia (particularly acute T-cell leukaemia), melanoma, osteosarcoma, ovarian cancer, pancreatic cancer and renal cell cancer samples. The full-length OGTA020 was detected in the plasma membrane of colorectal cancer, hepatocellular carcinoma, lung cancer, melanoma, pancreatic cancer and renal cell cancer samples. The full-length OGTA067 was detected in the plasma membrane of colorectal cancer, kidney cancer and ovarian cancer samples. The full-length OGTA116 was detected in the plasma membrane of gastric cancer, hepatocellular carcinoma and pancreatic cancer samples. The full-length OGTA194 was detected in the plasma membrane of B-cell non-Hodgkin's lymphoma, breast cancer, colorectal cancer, hepatocellular carcinoma, lung cancer, melanoma, ovarian cancer, pancreatic cancer, prostate cancer and renal cell cancer samples.

EXAMPLE 2

Identification of Membrane Proteins Expressed in Colorectal Cancer, Liver Cancer, Kidney Cancer, Lung Cancer or Ovarian Cancer Blood and Tissue Samples Using Isotope Tagging for Absolute and Relative Quantitation (iTRAQ)

Using the following Reference Protocols, membrane proteins extracted from colorectal cancer, liver cancer, kidney cancer, lung cancer and ovarian cancer tissue and normal adjacent colorectal, liver, kidney, lung and ovarian tissue samples were digested, labelled with Isotope Tagging for Absolute & Relative Quantitation reagents (iTRAQ; Applied Biosystems, Foster City, Calif., USA) and resulting peptides sequenced by tandem mass spectrometry.

2.1 Materials and Methods 2.1.1—Plasma Membrane Fractionation

The cells recovered from a colorectal cancer, liver cancer, kidney cancer, lung cancer or ovarian cancer or normal adjacent colorectal, liver, kidney, lung or ovarian tissue were lysed and submitted to centrifugation at 1000 G. The supernatant was taken, and it was subsequently centrifuged at 3000 G. Once again, the supernatant was taken, and it was then centrifuged at 100 000 G.

The resulting pellet was recovered and put on 15-60% sucrose gradient.

A Western blot was used to identify sub cellular markers, and the Plasma Membrane fractions were pooled.

The pooled solution was then analysed directly by iTRAQ (see section 2.1.2 below).

2.1.2—iTRAQ Methodology

Membrane protein pellets from colorectal cancer, liver cancer, kidney cancer, lung cancer or ovarian cancer and normal adjacent colorectal, liver, kidney, lung or ovarian tissue were solubilised in sample buffer (2-4 μg/μl in 0.5% SDS) by the addition of buffer and then heating to 95° C. for 3 min.

To a volume of each protein solution equating to 50 μg, 150 μl of 0.5M triethylammonium bicarbonate (TEAB) solution was added. To each sample, 3 1 of 50 mM tris-(2-carboxyethyl)phosphine was added and the mixture was incubated at 60° C. for 1 hour. 1 μl of cysteine blocking reagent, 200 mM methyl methanesulphonate (MMTS) in isopropanol, was then added. After incubation at room temperature for 10 minutes, 15 µl of 1 µg/µl trypsin was added to each sample followed by incubation at 37° C. overnight.

The digested samples were dried under a vacuum and re-constituted with 30 µl of 0.5M TEAB solution. 70 µl ethanol was added to each of the four iTRAQ reagents (114/115/116/117) and one reagent added to each of the four samples analysed (two colorectal cancer, liver cancer, kidney cancer, lung cancer or ovarian cancer samples and two corresponding normal adjacent tissue samples) and left at room temperature for 1 hour. The specific reagent added to each sample was recorded. The four labeled samples were combined & vortexed.

The combined sample was reduced to dryness under a vacuum and de-salted by loading onto a C18 spin column, washing with aqueous solvent and then eluting with 70% acetonitrile. The sample fraction was again reduced to dryness and then re-dissolved in 40 µl of solvent A (97.9 water, 2% acetonitrile, 0.1% formic acid) prior to ion exchange fractionation.

2.1.3—Fractionation and Analysis of Labeled Peptides

The sample was fractionated by strong cation exchange chromatography using an Agilent 1200 chromatograph (Agilent, Santa Clara, Calif., USA). Samples were eluted off an Agilent Zorbax Bio-SCXII column (3.5 µm; 50×0.8 mm) using a 200 min gradient of 0-100 mM sodium acetate over 20 minutes and then to 1M over 10 minutes. 1 minute fractions were collected over the 30 minute run.

Each fraction was analysed by liquid chromatography/mass spectrometry using an Agilent 1200 chromatograph fitted with a Zorbax 300SB-C18 (150 mm×75 µm) and an Agilent 6510 quadrupole—time-of-flight instrument (Agilent, Santa Clara, Calif., USA). Peptides were eluted with a 300 nl/min gradient increasing from 15% to 45% acetonitrile in 60 minutes. Data was acquired in auto MS/MS mode such that up to 3 precursor ions above the intensity threshold were selected and product ion spectra accumulated to facilitate the sequencing of the labeled peptides. Raw was processed to create peak lists using Spectrum Mill software (Agilent, Santa Clara, Calif., USA).

2.1.4—Amino Acid Sequence Analysis of Labeled Peptides

For partial amino acid sequencing and identification of OGTA014, OGTA020, OGTA067, OGTA116 and OGTA194, uninterpreted tandem mass spectra of tryptic peptides were searched using the SEQUEST search program (Eng et al., 1994, J. Am. Soc. Mass Spectrom. 5:976-989). Criteria for database identification included: the cleavage specificity of trypsin; the detection of a suite of a, b and y ions in peptides returned from the database, and a mass increment for all cysteine residues to account for modification with methyl methanesulphonate and the addition of iTRAQ labels to free amines (N-terminus & lysine). The data was searched through IPI Human v3.23 (www.ebi.ac.uk/IPI/IPI-human.html).

2.1.5—Discrimination of Colorectal Cancer, Kidney Cancer, Liver Cancer, Lung Cancer and Ovarian Cancer Associated Proteins The process described in Example 1 section 1.1.6 was employed to discriminate the colorectal cancer, liver cancer, kidney cancer, lung cancer and ovarian cancer associated proteins in the experimental samples.

2.2 Results

These experiments identified OGTA014, OGTA020, OGTA067 and OGTA194, as further described herein. The full-length OGTA014 was detected in the plasma membrane of colorectal cancer and lung cancer samples. The full-length OGTA020 was detected in the plasma membrane of kidney cancer samples. The full-length OGTA067 was detected in the plasma membrane of kidney cancer samples. The full-length OGTA194 was detected in the plasma membrane of ovarian cancer and lung cancer samples. The iTRAQ analysis showed that levels of the proteins of the invention in the cancer samples were higher than in the matched normal adjacent tissue samples.

All references referred to in this application, including patent and patent applications, are incorporated herein by reference to the fullest extent possible.

Embodiments of the invention are described herein, which comprise certain elements. The invention also extends to separate embodiments consisting of or consisting essentially of the same elements, and vice versa.

Throughout the specification and the claims which follow, unless the context requires otherwise, the word "comprise", and variations such as "comprises" and "comprising", will be understood to imply the inclusion of a stated integer, step, group of integers or group of steps but not to the exclusion of any other integer, step, group of integers or group of steps.

The application of which this description and claims form part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A method comprising administering to a patient having a cancer expressing increased levels of OGTA014, OGTA020, OGTA067, OGTA116 or OGTA194 as compared to a healthy control a composition comprising an antibody capable of specific binding to OGTA014, OGTA020, OGTA067, OGTA116 or OGTA194 as defined in SEQ ID NO: 1, SEQ ID NO: 2, SEQ ID NO: 3, SEQ ID NO: 4 or SEQ ID NO: 5 respectively, or a fragment thereof, and a pharmaceutically acceptable diluent or carrier, wherein the antibody is conjugated to a therapeutic moiety.

2. The method according to claim 1, said patient has B-cell non-Hodgkin's lymphoma, breast cancer, colorectal cancer, gastric cancer, hepatocellular carcinoma, lung cancer, lymphoid leukemia, acute T-cell leukemia, melanoma, osteosarcoma, ovarian cancer, pancreatic cancer, prostate cancer or renal cell cancer, or has increased likelihood of developing B-cell non-Hodgkin's lymphoma, breast cancer, colorectal cancer, gastric cancer, hepatocellular carcinoma, lung cancer, lymphoid leukemia, acute T-cell leukemia, melanoma, osteosarcoma, ovarian cancer, pancreatic cancer, prostate cancer or renal cell cancer.

3. The method of claim 2, wherein said antibody comprises a label.

4. The method according to claim 3, wherein said label is a detectable label or therapeutic moiety.

5. The method according to claim 4, wherein said therapeutic moiety is selected from the group consisting of a cytotoxic moiety and a radioactive isotope.

6. The method of claim 1, wherein said antibody comprises a label.

7. The method according to claim 6, wherein said label is a detectable label or therapeutic moiety.

8. The method according to claim 7, wherein said therapeutic moiety is selected from the group consisting of a cytotoxic moiety and a radioactive isotope .

9. The method of claim 1, wherein said antibody is a monoclonal antibody, a humanized antibody, a bispecific antibody, a non-fucosylated antibody, an antibody fragment, or an antibody mimetic.

10. The method of claim 1, wherein said antibody has cytotoxicity against OGTA014, OGTA020, OGTA067, OGTA116 or OGTA194 antigen expressing cells in the presence of a human complement or in the presence of human immune effector cells.

* * * * *

UNITED STATES PATENT AND TRADEMARK OFFICE
CERTIFICATE OF CORRECTION

PATENT NO. : 8,084,034 B2
APPLICATION NO. : 12/547789
DATED : December 27, 2011
INVENTOR(S) : Rohlff et al.

It is certified that error appears in the above-identified patent and that said Letters Patent is hereby corrected as shown below:

On the Title page, left column, Item (75) under Inventors, after the name Christian Rohlff, delete "Oxford (GB)", and insert --Abingdon (GB)--.

Signed and Sealed this
Twenty-seventh Day of March, 2012

David J. Kappos
*Director of the United States Patent and Trademark Office*

SEQUENCE LISTING

<160> NUMBER OF SEQ ID NOS: 87

<210> SEQ ID NO 1
<211> LENGTH: 660
<212> TYPE: PRT
<213> ORGANISM: Homo Sapiens
<220> FEATURE:
<221> NAME/KEY: MISC_FEATURE
<222> LOCATION: (1)..(660)
<223> OTHER INFORMATION: Swissprot Accession no: Q01650 - Large neutral
      amino acid transporter small subunit 1: designated in application
      as OGTA014

<400> SEQUENCE: 1

-continued

```
Arg Arg Ala Ala Arg Thr Leu Leu Ala Gly Pro Arg Leu Pro Gly Val
 1               5                  10                 15

Pro Gly Pro Ala Gly Ala Gln Ser Met Ala Gly Ala Gly Pro Lys Arg
            20                  25                  30

Arg Ala Leu Ala Ala Pro Ala Ala Glu Glu Lys Glu Glu Ala Arg Glu
             35                  40                  45

Lys Met Leu Ala Ala Lys Ser Ala Asp Gly Ser Ala Pro Ala Gly Glu
 50                  55                  60

Gly Glu Gly Val Thr Leu Gln Arg Asn Ile Thr Leu Leu Asn Gly Val
 65                  70                  75                  80

Ala Ile Ile Val Gly Thr Ile Ile Gly Ser Gly Ile Phe Val Thr Pro
                 85                  90                  95

Thr Gly Val Leu Lys Glu Ala Gly Ser Pro Gly Leu Ala Leu Val Val
                100                 105                 110

Trp Ala Ala Cys Gly Val Phe Ser Ile Val Gly Ala Leu Cys Tyr Ala
            115                 120                 125

Glu Leu Gly Thr Thr Ile Ser Lys Ser Gly Gly Asp Tyr Ala Tyr Met
            130                 135                 140

Leu Glu Val Tyr Gly Ser Leu Pro Ala Phe Leu Lys Leu Trp Ile Glu
145                 150                 155                 160

Leu Leu Ile Ile Arg Pro Ser Ser Gln Tyr Ile Val Ala Leu Val Phe
                165                 170                 175

Ala Thr Tyr Leu Leu Lys Pro Leu Phe Pro Thr Cys Pro Val Pro Glu
            180                 185                 190

Glu Ala Ala Lys Leu Val Ala Cys Leu Cys Val Leu Leu Leu Thr Ala
            195                 200                 205

Val Asn Cys Tyr Ser Val Lys Ala Ala Thr Arg Val Gln Asp Ala Phe
210                 215                 220

Ala Ala Ala Lys Leu Leu Ala Leu Ala Leu Ile Ile Leu Leu Gly Phe
225                 230                 235                 240

Val Gln Ile Gly Lys Gly Asp Val Ser Asn Leu Asp Pro Asn Phe Ser
                245                 250                 255

Phe Glu Gly Thr Lys Leu Asp Val Gly Asn Ile Val Leu Ala Leu Tyr
            260                 265                 270

Ser Gly Leu Phe Ala Tyr Gly Gly Trp Asn Tyr Leu Asn Phe Val Thr
            275                 280                 285

Glu Glu Met Ile Asn Pro Tyr Arg Asn Leu Pro Leu Ala Ile Ile Ile
            290                 295                 300

Ser Leu Pro Ile Val Thr Leu Val Tyr Val Leu Thr Asn Leu Ala Tyr
305                 310                 315                 320

Phe Thr Thr Leu Ser Thr Glu Gln Met Leu Ser Ser Glu Ala Val Ala
                325                 330                 335

Val Asp Phe Gly Asn Tyr His Leu Gly Val Met Ser Trp Ile Ile Pro
            340                 345                 350

Val Phe Val Gly Leu Ser Cys Phe Gly Ser Val Asn Gly Ser Leu Phe
            355                 360                 365

Thr Ser Ser Arg Leu Phe Phe Val Gly Ser Arg Glu Gly His Leu Pro
            370                 375                 380

Ser Ile Leu Ser Met Ile His Pro Gln Leu Leu Thr Pro Val Pro Ser
385                 390                 395                 400

Leu Val Phe Thr Cys Val Met Thr Leu Leu Tyr Ala Phe Ser Lys Asp
                405                 410                 415

Ile Phe Ser Val Ile Asn Phe Phe Ser Phe Phe Asn Trp Leu Cys Val
            420                 425                 430
```

```
Ala Leu Ala Ile Ile Gly Met Ile Trp Leu Arg His Arg Lys Pro Glu
            435                 440                 445

Leu Glu Arg Pro Ile Lys Val Asn Leu Ala Leu Pro Val Phe Phe Ile
450                 455                 460

Leu Ala Cys Leu Phe Leu Ile Ala Val Ser Phe Trp Lys Thr Pro Val
465                 470                 475                 480

Glu Cys Gly Ile Gly Phe Thr Ile Ile Leu Ser Gly Leu Pro Val Tyr
                485                 490                 495

Phe Phe Gly Val Trp Trp Lys Asn Lys Pro Lys Trp Leu Leu Gln Gly
            500                 505                 510

Ile Trp Ile Arg His Thr Ala Gln His Gln Leu Ile Ser Gln Asp Glu
515                 520                 525

Gly Phe Arg Lys Thr Arg Leu Leu Leu Pro Ser Asn Lys Ile Leu Leu
        530                 535                 540

Ala Ala Thr Ser Gly His Ser Arg Leu Thr Gln Lys Gly Arg Lys Arg
545                 550                 555                 560

Gln Arg Gln Ala Asp His Leu Ser Gln Arg Trp Ser Gln Val Val Gln
                565                 570                 575

Arg His Ser Ser Ala Gln Leu Trp Leu Glu Leu Ala Cys Gly Thr
            580                 585                 590

Ala Leu Ser Val Pro Ser Arg Glu Pro Thr Lys Pro Asp Thr Ala Ser
                595                 600                 605

Leu Thr Ser Gly Cys Ser Ser Arg Lys Leu Ser Ala Ser Ala Gln Trp
610                 615                 620

Ser Leu Pro Pro Pro Gly His Arg Asp Pro Leu Thr Ile Gln Trp
625                 630                 635                 640

Ala Arg Arg Asn Leu Met Asn Ser Leu Gly Thr Gln Asp Gln Met Ser
                645                 650                 655

Val Ser Leu Ala
            660

<210> SEQ ID NO 2
<211> LENGTH: 669
<212> TYPE: PRT
<213> ORGANISM: Homo Sapiens
<220> FEATURE:
<221> NAME/KEY: MISC_FEATURE
<222> LOCATION: (1)..(669)
<223> OTHER INFORMATION: Swissprot Accession no: P42892 - Endothelin
      converting enzyme 1: designated in application as OGTA020

<400> SEQUENCE: 2

Met Arg Gly Val Trp Pro Pro Val Ser Ala Leu Leu Ser Ala Leu
1               5                   10                  15

Gly Met Ser Thr Tyr Lys Arg Ala Thr Leu Asp Glu Glu Asp Leu Val
                20                  25                  30

Asp Ser Leu Ser Glu Gly Asp Ala Tyr Pro Asn Gly Leu Gln Val Asn
        35                  40                  45

Phe His Ser Pro Arg Ser Gly Gln Arg Cys Trp Ala Ala Arg Thr Gln
    50                  55                  60

Val Glu Lys Arg Leu Val Val Leu Val Leu Ala Ala Gly Leu
65                  70                  75                  80

Val Ala Cys Leu Ala Ala Leu Gly Ile Gln Tyr Gln Thr Arg Ser Pro
                85                  90                  95

Ser Val Cys Leu Ser Glu Ala Cys Val Ser Val Thr Ser Ser Ile Leu
            100                 105                 110
```

-continued

Ser Ser Met Asp Pro Thr Val Asp Pro Cys His Asp Phe Ser Tyr
    115                 120                 125

Ala Cys Gly Gly Trp Ile Lys Ala Asn Pro Val Pro Asp Gly His Ser
130                 135                 140

Arg Trp Gly Thr Phe Ser Asn Leu Trp Glu His Asn Gln Ala Ile Ile
145                 150                 155                 160

Lys His Leu Leu Glu Asn Ser Thr Ala Ser Val Ser Glu Ala Glu Arg
                165                 170                 175

Lys Ala Gln Val Tyr Tyr Arg Ala Cys Met Asn Glu Thr Arg Ile Glu
            180                 185                 190

Glu Leu Arg Ala Lys Pro Leu Met Glu Leu Ile Glu Arg Leu Gly Gly
        195                 200                 205

Trp Asn Ile Thr Gly Pro Trp Ala Lys Asp Asn Phe Gln Asp Thr Leu
210                 215                 220

Gln Val Val Thr Ala His Tyr Arg Thr Ser Pro Phe Phe Ser Val Tyr
225                 230                 235                 240

Val Ser Ala Asp Ser Lys Asn Ser Asn Ser Asn Val Ile Gln Val Asp
                245                 250                 255

Gln Ser Gly Leu Gly Leu Pro Ser Arg Asp Tyr Tyr Leu Asn Lys Thr
            260                 265                 270

Glu Asn Glu Lys Val Leu Thr Gly Tyr Leu Asn Tyr Met Val Gln Leu
        275                 280                 285

Gly Lys Leu Leu Gly Gly Gly Asp Glu Glu Ala Ile Arg Pro Gln Met
290                 295                 300

Gln Gln Ile Leu Asp Phe Glu Thr Ala Leu Ala Asn Ile Thr Ile Pro
305                 310                 315                 320

Gln Glu Lys Arg Arg Asp Glu Glu Leu Ile Tyr His Lys Val Thr Ala
                325                 330                 335

Ala Glu Leu Gln Thr Leu Ala Pro Ala Ile Asn Trp Leu Pro Phe Leu
            340                 345                 350

Asn Thr Ile Phe Tyr Pro Val Glu Ile Asn Glu Ser Glu Pro Ile Val
        355                 360                 365

Val Tyr Asp Lys Glu Tyr Leu Glu Gln Ile Ser Thr Leu Ile Asn Thr
370                 375                 380

Thr Asp Arg Cys Leu Leu Asn Asn Tyr Met Ile Trp Asn Leu Val Arg
385                 390                 395                 400

Lys Thr Ser Ser Phe Leu Asp Gln Arg Phe Gln Asp Ala Asp Glu Lys
                405                 410                 415

Phe Met Glu Val Met Tyr Gly Thr Lys Lys Gly Thr Thr Asn Ser Ile
            420                 425                 430

Thr Ser Ser Pro Glu Thr Gln Thr Pro Glu Gly Ala Glu Arg Ile Gly
        435                 440                 445

Gly Pro Gln Thr Ser Gly Val Gly Trp Ser Met Thr Pro Pro Met Val
450                 455                 460

Asn Ala Tyr Tyr Ser Pro Thr Lys Asn Glu Ile Val Phe Pro Ala Gly
465                 470                 475                 480

Ile Leu Gln Ala Pro Phe Tyr Thr Arg Ser Ser Pro Lys Ala Leu Asn
                485                 490                 495

Phe Gly Gly Ile Gly Val Val Gly His Glu Leu Thr His Ala Phe
            500                 505                 510

Asp Asp Gln Gly Arg Glu Tyr Asp Lys Asp Gly Asn Leu Arg Pro Trp
        515                 520                 525

Trp Lys Asn Ser Ser Val Glu Ala Phe Lys Arg Gln Thr Glu Cys Met
530                 535                 540

```
Val Glu Gln Tyr Ser Asn Tyr Ser Val Asn Gly Pro Val Asn Gly
545                 550                 555                 560

Arg His Thr Leu Gly Glu Asn Ile Ala Asp Asn Gly Gly Leu Lys Ala
                565                 570                 575

Ala Tyr Arg Ala Tyr Gln Asn Trp Val Lys Lys Asn Gly Ala Glu His
            580                 585                 590

Ser Leu Pro Thr Leu Gly Leu Thr Asn Asn Gln Leu Phe Phe Leu Gly
        595                 600                 605

Phe Ala Gln Val Trp Cys Ser Val Arg Thr Pro Glu Ser Ser His Glu
    610                 615                 620

Gly Leu Ile Thr Asp Pro His Ser Pro Ser Arg Phe Arg Val Ile Gly
625                 630                 635                 640

Ser Leu Ser Asn Ser Lys Glu Phe Ser Glu His Phe Arg Cys Pro Pro
                645                 650                 655

Gly Ser Pro Met Asn Pro Pro His Lys Cys Glu Val Trp
            660                 665

<210> SEQ ID NO 3
<211> LENGTH: 1075
<212> TYPE: PRT
<213> ORGANISM: Homo Sapiens
<220> FEATURE:
<221> NAME/KEY: MISC_FEATURE
<222> LOCATION: (1)..(1075)
<223> OTHER INFORMATION: Swissprot Accession no: Q9NR17 - Procadherin
      beta 16: designated in application as OGTA067

<400> SEQUENCE: 3

Val Gln Ile Ser Glu Asp Ser Pro Ile Ser Phe Leu Val Val Lys Val
1               5                   10                  15

Ser Ala Thr Asp Val Asp Thr Gly Val Asn Gly Glu Ile Ser Tyr Ser
            20                  25                  30

Leu Phe Gln Ala Ser Asp Glu Ile Ser Lys Thr Phe Lys Val Asp Phe
        35                  40                  45

Leu Thr Gly Glu Ile Arg Leu Lys Lys Gln Leu Asp Phe Glu Lys Phe
    50                  55                  60

Gln Ser Tyr Glu Val Asn Ile Glu Ala Arg Asp Ala Gly Gly Phe Ser
65                  70                  75                  80

Gly Lys Cys Thr Val Leu Ile Gln Val Ile Asp Val Asn Asp His Ala
                85                  90                  95

Pro Glu Val Thr Met Ser Ala Phe Thr Ser Pro Ile Pro Glu Asn Ala
            100                 105                 110

Pro Glu Thr Val Val Ala Leu Phe Ser Val Ser Asp Leu Asp Ser Gly
        115                 120                 125

Glu Asn Gly Lys Ile Ser Cys Ser Ile Gln Glu Asp Leu Pro Phe Leu
    130                 135                 140

Leu Lys Ser Ser Val Gly Asn Phe Tyr Thr Leu Leu Thr Glu Thr Pro
145                 150                 155                 160

Leu Asp Arg Glu Ser Arg Ala Glu Tyr Asn Val Thr Ile Thr Val Thr
                165                 170                 175

Asp Leu Gly Thr Pro Arg Leu Thr Thr His Leu Asn Met Thr Val Leu
            180                 185                 190

Val Ser Asp Val Asn Asp Asn Ala Pro Ala Phe Thr Gln Thr Ser Tyr
        195                 200                 205

Thr Leu Phe Val Arg Glu Asn Asn Ser Pro Ala Leu His Ile Gly Ser
    210                 215                 220
```

```
Val Ser Ala Thr Asp Arg Asp Ser Gly Thr Asn Ala Gln Val Thr Tyr
225                 230                 235                 240

Ser Leu Leu Pro Pro Gln Asp Pro His Leu Pro Leu Ala Ser Leu Val
            245                 250                 255

Ser Ile Asn Thr Asp Asn Gly His Leu Phe Ala Leu Arg Ser Leu Asp
        260                 265                 270

Tyr Glu Ala Leu Gln Ala Phe Glu Phe Arg Val Gly Ala Ser Asp Arg
    275                 280                 285

Gly Ser Pro Ala Leu Ser Ser Glu Ala Leu Val Arg Val Leu Val Leu
290                 295                 300

Asp Ala Asn Asp Asn Ser Pro Phe Val Leu Tyr Pro Leu Gln Asn Gly
305                 310                 315                 320

Ser Ala Pro Cys Thr Glu Leu Val Pro Arg Ala Ala Glu Pro Gly Tyr
            325                 330                 335

Leu Val Thr Lys Val Ala Val Asp Gly Asp Ser Gly Gln Asn Ala
        340                 345                 350

Trp Leu Ser Tyr Gln Leu Leu Lys Ala Thr Glu Pro Gly Leu Phe Gly
    355                 360                 365

Val Trp Ala His Asn Gly Glu Val Arg Thr Ala Arg Leu Leu Ser Glu
370                 375                 380

Arg Asp Ala Ala Lys Gln Arg Leu Val Val Leu Val Lys Asp Asn Gly
385                 390                 395                 400

Glu Pro Pro Cys Ser Ala Thr Ala Thr Leu His Leu Leu Val Asp
            405                 410                 415

Gly Phe Ser Gln Pro Tyr Leu Pro Leu Pro Glu Ala Ala Pro Ala Gln
        420                 425                 430

Gly Gln Ala Asp Ser Leu Thr Val Tyr Leu Val Val Ala Leu Ala Ser
        435                 440                 445

Val Ser Ser Leu Phe Leu Phe Ser Val Leu Leu Phe Val Ala Val Leu
450                 455                 460

Leu Cys Arg Arg Ser Arg Ala Ala Ser Val Gly Arg Cys Ser Val Pro
465                 470                 475                 480

Glu Gly Pro Phe Pro Gly His Leu Val Asp Val Arg Gly Thr Gly Ser
            485                 490                 495

Leu Ser Gln Asn Tyr His Leu Ser Gly Ala Gly Ala Glu Leu Gly Ser
        500                 505                 510

Tyr Ser Val Val Glu Glu Thr Glu Arg Gly Ser Phe Val Ala Asn Leu
    515                 520                 525

Gly Lys Asp Leu Gly Leu Gly Leu Thr Glu Met Ser Thr Arg Lys Ala
530                 535                 540

Arg Ile Ile Ser Gln Gly Asn Lys Gln His Leu Gln Leu Lys Ala Gln
545                 550                 555                 560

Thr Gly Asp Leu Leu Ile Asn Glu Lys Leu Asp Arg Glu Glu Leu Cys
            565                 570                 575

Gly Pro Thr Glu Pro Cys Ile Leu His Phe Gln Val Leu Met Glu Asn
        580                 585                 590

Pro Leu Glu Ile Phe Gln Ala Glu Leu Arg Val Ile Asp Ile Asn Asp
        595                 600                 605

His Ser Pro Met Phe Thr Glu Lys Glu Met Ile Leu Lys Ile Pro Glu
610                 615                 620

Asn Ser Pro Leu Gly Thr Glu Phe Pro Leu Asn His Ala Leu Asp Leu
625                 630                 635                 640

Asp Val Gly Ser Asn Asn Val Gln Asn Tyr Lys Ile Ser Pro Ser Ser
            645                 650                 655
```

```
His Phe Arg Val Leu Ile His Glu Phe Arg Asp Gly Arg Lys Tyr Pro
            660                 665                 670

Glu Leu Val Leu Asp Lys Glu Leu Asp Arg Glu Glu Pro Gln Leu
    675                 680                 685

Arg Leu Thr Leu Thr Ala Leu Asp Gly Gly Ser Pro Arg Ser Gly
690                 695                 700

Thr Ala Gln Val Arg Ile Glu Val Val Asp Ile Asn Asp Asn Ala Pro
705                 710                 715                 720

Glu Phe Glu Gln Pro Ile Tyr Lys Val Gln Ile Pro Glu Asn Ser Pro
                725                 730                 735

Leu Gly Ser Leu Val Ala Thr Val Ser Ala Arg Asp Leu Asp Gly Gly
            740                 745                 750

Ala Asn Gly Lys Ile Ser Tyr Thr Leu Phe Gln Pro Ser Glu Asp Ile
            755                 760                 765

Ser Lys Thr Leu Glu Val Asn Pro Met Thr Gly Gly Thr Pro Arg Leu
    770                 775                 780

Lys Thr Glu His Asn Ile Thr Val Gln Ile Ser Asp Val Asn Asp Asn
785                 790                 795                 800

Ala Pro Thr Phe Thr Gln Thr Ser Tyr Thr Leu Phe Val Arg Glu Asn
                805                 810                 815

Asn Ser Pro Ala Leu His Ile Gly Ser Val Ser Ala Thr Asp Arg Asp
            820                 825                 830

Ser Gly Thr Asn Ala Gln Val Thr Tyr Ser Leu Leu Pro Pro Gln Asp
            835                 840                 845

Pro His Leu Pro Leu Ala Ser Leu Val Ser Ile Asn Ala Asp Asn Gly
850                 855                 860

His Leu Phe Ala Leu Arg Ser Leu Asp Tyr Glu Ala Leu Arg Glu Phe
865                 870                 875                 880

Glu Phe Arg Val Ser Ala Thr Asp Arg Gly Ser Pro Ala Leu Ser Ser
                885                 890                 895

Glu Ala Leu Val Arg Val Leu Val Asp Ala Asn Asp Asn Ser Pro
            900                 905                 910

Phe Val Leu Tyr Pro Leu Gln Asn Gly Ser Ala Pro Cys Thr Glu Leu
            915                 920                 925

Val Pro Arg Ala Ala Glu Pro Gly Tyr Leu Val Thr Lys Val Val Ala
    930                 935                 940

Val Asp Gly Asp Ser Gly Gln Asn Ala Trp Leu Ser Tyr Gln Leu Leu
945                 950                 955                 960

Lys Ala Thr Glu Pro Gly Leu Phe Gly Val Trp Ala His Asn Gly Glu
                965                 970                 975

Val Arg Thr Ala Arg Leu Leu Ser Glu Arg Asp Ala Ala Lys Gln Arg
            980                 985                 990

Leu Val Val Leu Val Lys Asp Asn Gly Glu Pro Pro Arg Ser Ala Thr
            995                 1000                1005

Ala Thr Leu His Val Leu Leu Val Asp Gly Phe Ser Gln Pro Phe
    1010                1015                1020

Leu Pro Leu Pro Glu Ala Ala Pro Gly Gln Thr Gln Ala Asn Ser
    1025                1030                1035

Leu Thr Val Tyr Leu Val Val Ala Ile Ser Leu Cys Leu Ile Cys
    1040                1045                1050

Ile Ser Cys Leu Leu Tyr Val Lys Leu Ser Phe Phe Leu Asp Ile
    1055                1060                1065

Arg Pro Leu Asn Lys Ile Leu
```

<210> SEQ ID NO 4
<211> LENGTH: 471
<212> TYPE: PRT
<213> ORGANISM: Homo Sapiens
<220> FEATURE:
<221> NAME/KEY: MISC_FEATURE
<222> LOCATION: (1)..(471)
<223> OTHER INFORMATION: Swissprot Accession no: P30825 - High affinity
cationic acid transporter 1: designated in application as OGTA116

<400> SEQUENCE: 4

```
Pro Phe Pro Gly Asp Gly Gly Thr Arg Gln Gln Ser Arg His Leu Ala
1               5                  10                  15
Gln Leu Glu Pro Trp Gly Pro Trp Gly Ser Cys Ala Gly Thr Trp Pro
            20                  25                  30
Val Ser Gly Ala Ala Leu Asn Ser Asn Met Gly Cys Lys Val Leu Leu
        35                  40                  45
Asn Ile Gly Gln Gln Met Leu Arg Arg Lys Val Val Asp Cys Ser Arg
    50                  55                  60
Glu Glu Thr Arg Leu Ser Arg Cys Leu Asn Thr Phe Asp Leu Val Ala
65                  70                  75                  80
Leu Gly Val Gly Ser Thr Leu Gly Ala Gly Val Tyr Val Leu Ala Gly
                85                  90                  95
Ala Val Ala Arg Glu Asn Ala Gly Pro Ala Ile Val Ile Ser Phe Leu
            100                 105                 110
Ile Ala Ala Leu Ala Ser Val Leu Ala Gly Leu Cys Tyr Gly Glu Phe
        115                 120                 125
Gly Ala Arg Val Pro Lys Thr Gly Ser Ala Tyr Leu Tyr Ser Tyr Val
    130                 135                 140
Thr Val Gly Glu Leu Trp Ala Phe Ile Thr Gly Trp Asn Leu Ile Leu
145                 150                 155                 160
Ser Tyr Ile Ile Gly Thr Ser Ser Val Ala Arg Ala Trp Ser Ala Thr
                165                 170                 175
Phe Asp Glu Leu Ile Gly Arg Pro Ile Gly Glu Phe Ser Arg Thr His
            180                 185                 190
Met Thr Leu Asn Ala Pro Gly Val Leu Ala Glu Asn Pro Asp Ile Phe
        195                 200                 205
Ala Val Ile Ile Ile Leu Ile Leu Thr Gly Leu Leu Thr Leu Gly Val
    210                 215                 220
Lys Glu Ser Ala Met Val Asn Lys Ile Phe Thr Cys Ile Asn Val Leu
225                 230                 235                 240
Val Leu Gly Phe Ile Met Val Ser Gly Phe Val Lys Gly Ser Val Lys
                245                 250                 255
Asn Trp Gln Leu Thr Glu Glu Asp Phe Gly Asn Thr Ser Gly Arg Leu
            260                 265                 270
Cys Leu Asn Asn Asp Thr Lys Glu Gly Lys Pro Gly Val Gly Gly Phe
        275                 280                 285
Met Pro Phe Gly Phe Ser Gly Val Leu Ser Gly Ala Ala Thr Cys Phe
    290                 295                 300
Tyr Ala Phe Val Gly Phe Asp Cys Ile Ala Thr Thr Gly Glu Glu Val
305                 310                 315                 320
Lys Asn Pro Gln Lys Ala Ile Pro Val Gly Ile Val Ala Ser Leu Leu
                325                 330                 335
Ile Cys Phe Ile Ala Tyr Phe Gly Val Ser Ala Ala Leu Thr Leu Met
            340                 345                 350
```

```
Met Pro Tyr Phe Cys Leu Asp Asn Asn Ser Pro Leu Pro Asp Ala Phe
        355                 360                 365

Lys His Val Gly Trp Glu Gly Ala Lys Tyr Ala Val Ala Val Gly Ser
    370                 375                 380

Leu Cys Ala Leu Ser Ala Ser Leu Leu Gly Ser Met Phe Pro Met Pro
385                 390                 395                 400

Arg Val Ile Tyr Ala Met Ala Glu Asp Gly Leu Leu Lys Phe Leu
                405                 410                 415

Ala Asn Val Asn Asp Arg Thr Lys Thr Pro Ile Ile Ala Thr Leu Ala
            420                 425                 430

Ser Gly Ala Val Ala Val Met Ala Phe Leu Phe Asp Leu Lys Asp
            435                 440                 445

Leu Val Asp Leu Met Ser Ile Gly Thr Leu Leu Ala Tyr Ser Leu Val
    450                 455                 460

Ala Ala Cys Val Leu Val Leu
465                 470

<210> SEQ ID NO 5
<211> LENGTH: 523
<212> TYPE: PRT
<213> ORGANISM: Homo Sapiens
<220> FEATURE:
<221> NAME/KEY: MISC_FEATURE
<222> LOCATION: (1)..(523)
<223> OTHER INFORMATION: Swissprot Accession no: Q8WTV0 - Scavenger
      receptor class B member 1: designated in application as OGTA194

<400> SEQUENCE: 5

Met Gly Cys Ser Ala Lys Ala Arg Trp Ala Ala Gly Ala Leu Gly Val
1               5                   10                  15

Ala Gly Leu Leu Cys Ala Val Leu Gly Ala Val Met Ile Val Met Val
            20                  25                  30

Pro Ser Leu Ile Lys Gln Gln Val Leu Lys Asn Val Arg Ile Asp Pro
        35                  40                  45

Ser Ser Leu Ser Phe Asn Met Trp Lys Glu Ile Pro Ile Pro Phe Tyr
    50                  55                  60

Leu Ser Val Tyr Phe Phe Asp Val Met Asn Pro Ser Glu Ile Leu Lys
65                  70                  75                  80

Gly Glu Lys Pro Gln Val Arg Glu Arg Gly Pro Tyr Val Tyr Arg Glu
                85                  90                  95

Phe Arg His Lys Ser Asn Ile Thr Phe Asn Asn Asn Asp Thr Val Ser
            100                 105                 110

Phe Leu Glu Tyr Arg Thr Phe Gln Phe Gln Pro Ser Lys Ser His Gly
        115                 120                 125

Ser Glu Ser Asp Tyr Ile Val Met Pro Asn Ile Leu Val Leu Gly Ala
    130                 135                 140

Ala Val Met Met Glu Asn Lys Pro Met Thr Leu Lys Leu Ile Met Thr
145                 150                 155                 160

Leu Ala Phe Thr Thr Leu Gly Glu Arg Ala Phe Met Asn Arg Thr Val
                165                 170                 175

Gly Glu Ile Met Trp Gly Tyr Lys Asp Pro Leu Val Asn Leu Ile Asn
            180                 185                 190

Lys Tyr Phe Pro Gly Met Phe Pro Phe Lys Asp Lys Phe Gly Leu Phe
        195                 200                 205

Ala Glu Leu Asn Asn Ser Asp Ser Gly Leu Phe Thr Val Phe Thr Gly
    210                 215                 220
```

Val Gln Asn Ile Ser Arg Ile His Leu Val Asp Lys Trp Asn Gly Leu
225                 230                 235                 240

Ser Lys Val Asp Phe Trp His Ser Asp Gln Cys Asn Met Ile Asn Gly
            245                 250                 255

Thr Ser Gly Gln Met Trp Pro Pro Phe Met Thr Pro Glu Ser Ser Leu
        260                 265                 270

Glu Phe Tyr Ser Pro Glu Ala Cys Arg Ser Met Lys Leu Met Tyr Lys
    275                 280                 285

Glu Ser Gly Val Phe Glu Gly Ile Pro Thr Tyr Arg Phe Val Ala Pro
290                 295                 300

Lys Thr Leu Phe Ala Asn Gly Ser Ile Tyr Pro Pro Asn Glu Gly Phe
305                 310                 315                 320

Cys Pro Cys Leu Glu Ser Gly Ile Gln Asn Val Ser Thr Cys Arg Phe
            325                 330                 335

Ser Ala Pro Leu Phe Leu Ser His Pro His Phe Leu Asn Ala Asp Pro
        340                 345                 350

Val Leu Ala Glu Ala Val Thr Gly Leu His Pro Asn Gln Glu Ala His
    355                 360                 365

Ser Leu Phe Leu Asp Ile His Pro Val Thr Gly Ile Pro Met Asn Cys
370                 375                 380

Ser Val Lys Leu Gln Leu Ser Leu Tyr Met Lys Ser Val Ala Gly Ile
385                 390                 395                 400

Gly Gln Thr Gly Lys Ile Glu Pro Val Val Leu Pro Leu Leu Trp Phe
            405                 410                 415

Ala Glu Ser Gly Ala Met Glu Gly Glu Thr Leu His Thr Phe Tyr Thr
        420                 425                 430

Gln Leu Val Leu Met Pro Lys Val Met His Tyr Ala Gln Tyr Val Leu
    435                 440                 445

Leu Ala Leu Gly Cys Val Leu Leu Val Pro Val Ile Cys Gln Ile
450                 455                 460

Arg Ser Gln Pro Pro Asn Gln His Pro Thr Leu Lys Ser Ser Lys Asn
465                 470                 475                 480

Ala Thr Ile Gly Ser Val Ala Pro Ser Leu Gln Val Ser Leu Glu Ala
            485                 490                 495

Thr Arg Asn Ala Ile Tyr Phe Gly Val Val Val Lys Arg Ala Gln Arg
        500                 505                 510

Ile Arg Arg Pro Phe Arg Pro Ile Leu Asn Pro
        515                 520

<210> SEQ ID NO 6
<211> LENGTH: 10
<212> TYPE: PRT
<213> ORGANISM: Homo Sapiens

<400> SEQUENCE: 6

Ala Lys Pro Leu Met Glu Leu Ile Glu Arg
1               5                   10

<210> SEQ ID NO 7
<211> LENGTH: 10
<212> TYPE: PRT
<213> ORGANISM: Homo Sapiens

<400> SEQUENCE: 7

Ala Leu Ala Ala Pro Ala Ala Glu Glu Lys
1               5                   10

```
<210> SEQ ID NO 8
<211> LENGTH: 10
<212> TYPE: PRT
<213> ORGANISM: Homo Sapiens

<400> SEQUENCE: 8

Ala Asn Pro Val Pro Asp Gly His Ser Arg
1               5                   10

<210> SEQ ID NO 9
<211> LENGTH: 6
<212> TYPE: PRT
<213> ORGANISM: Homo Sapiens

<400> SEQUENCE: 9

Ala Gln Val Tyr Tyr Arg
1               5

<210> SEQ ID NO 10
<211> LENGTH: 17
<212> TYPE: PRT
<213> ORGANISM: Homo Sapiens

<400> SEQUENCE: 10

Ala Thr Glu Pro Gly Leu Phe Gly Val Trp Ala His Asn Gly Glu Val
1               5                   10                  15

Arg

<210> SEQ ID NO 11
<211> LENGTH: 7
<212> TYPE: PRT
<213> ORGANISM: Homo Sapiens

<400> SEQUENCE: 11

Ala Tyr Gln Asn Trp Val Lys
1               5

<210> SEQ ID NO 12
<211> LENGTH: 8
<212> TYPE: PRT
<213> ORGANISM: Homo Sapiens

<400> SEQUENCE: 12

Ala Tyr Gln Asn Trp Val Lys Lys
1               5

<210> SEQ ID NO 13
<211> LENGTH: 13
<212> TYPE: PRT
<213> ORGANISM: Homo Sapiens

<400> SEQUENCE: 13

Cys Leu Leu Asn Asn Tyr Met Ile Trp Asn Leu Val Arg
1               5                   10

<210> SEQ ID NO 14
<211> LENGTH: 14
<212> TYPE: PRT
<213> ORGANISM: Homo Sapiens

<400> SEQUENCE: 14

Cys Leu Leu Asn Asn Tyr Met Ile Trp Asn Leu Val Arg Lys
1               5                   10

<210> SEQ ID NO 15
```

```
<211> LENGTH: 12
<212> TYPE: PRT
<213> ORGANISM: Homo Sapiens

<400> SEQUENCE: 15

Cys Pro Pro Gly Ser Pro Met Asn Pro His Lys
1               5                   10

<210> SEQ ID NO 16
<211> LENGTH: 16
<212> TYPE: PRT
<213> ORGANISM: Homo Sapiens

<400> SEQUENCE: 16

Cys Ser Val Pro Glu Gly Pro Phe Pro Gly His Leu Val Asp Val Arg
1               5                   10                  15

<210> SEQ ID NO 17
<211> LENGTH: 9
<212> TYPE: PRT
<213> ORGANISM: Homo Sapiens

<400> SEQUENCE: 17

Asp Gly Asn Leu Arg Pro Trp Trp Lys
1               5

<210> SEQ ID NO 18
<211> LENGTH: 12
<212> TYPE: PRT
<213> ORGANISM: Homo Sapiens

<400> SEQUENCE: 18

Asp Leu Gly Leu Gly Leu Thr Glu Met Ser Thr Arg
1               5                   10

<210> SEQ ID NO 19
<211> LENGTH: 15
<212> TYPE: PRT
<213> ORGANISM: Homo Sapiens

<400> SEQUENCE: 19

Asp Asn Phe Gln Asp Thr Leu Gln Val Val Thr Ala His Tyr Arg
1               5                   10                  15

<210> SEQ ID NO 20
<211> LENGTH: 9
<212> TYPE: PRT
<213> ORGANISM: Homo Sapiens

<400> SEQUENCE: 20

Asp Pro Leu Thr Ile Gln Trp Ala Arg
1               5

<210> SEQ ID NO 21
<211> LENGTH: 10
<212> TYPE: PRT
<213> ORGANISM: Homo Sapiens

<400> SEQUENCE: 21

Asp Pro Leu Thr Ile Gln Trp Ala Arg Arg
1               5                   10

<210> SEQ ID NO 22
<211> LENGTH: 9
<212> TYPE: PRT
<213> ORGANISM: Homo Sapiens
```

```
<400> SEQUENCE: 22

Asp Pro Leu Val Asn Leu Ile Asn Lys
1               5

<210> SEQ ID NO 23
<211> LENGTH: 7
<212> TYPE: PRT
<213> ORGANISM: Homo Sapiens

<400> SEQUENCE: 23

Glu Phe Ser Glu His Phe Arg
1               5

<210> SEQ ID NO 24
<211> LENGTH: 12
<212> TYPE: PRT
<213> ORGANISM: Homo Sapiens

<400> SEQUENCE: 24

Glu Ser Gly Val Phe Glu Gly Ile Pro Thr Tyr Arg
1               5                   10

<210> SEQ ID NO 25
<211> LENGTH: 8
<212> TYPE: PRT
<213> ORGANISM: Homo Sapiens

<400> SEQUENCE: 25

Phe Leu Ala Asn Val Asn Asp Arg
1               5

<210> SEQ ID NO 26
<211> LENGTH: 10
<212> TYPE: PRT
<213> ORGANISM: Homo Sapiens

<400> SEQUENCE: 26

Phe Met Glu Val Met Tyr Gly Thr Lys Lys
1               5                   10

<210> SEQ ID NO 27
<211> LENGTH: 7
<212> TYPE: PRT
<213> ORGANISM: Homo Sapiens

<400> SEQUENCE: 27

Phe Gln Asp Ala Asp Glu Lys
1               5

<210> SEQ ID NO 28
<211> LENGTH: 16
<212> TYPE: PRT
<213> ORGANISM: Homo Sapiens

<400> SEQUENCE: 28

Gly Asp Val Ser Asn Leu Asp Pro Asn Phe Ser Phe Glu Gly Thr Lys
1               5                   10                  15

<210> SEQ ID NO 29
<211> LENGTH: 7
<212> TYPE: PRT
<213> ORGANISM: Homo Sapiens

<400> SEQUENCE: 29
```

```
Gly Glu Lys Pro Gln Val Arg
1               5

<210> SEQ ID NO 30
<211> LENGTH: 6
<212> TYPE: PRT
<213> ORGANISM: Homo Sapiens

<400> SEQUENCE: 30

Gly Pro Tyr Val Tyr Arg
1               5

<210> SEQ ID NO 31
<211> LENGTH: 21
<212> TYPE: PRT
<213> ORGANISM: Homo Sapiens

<400> SEQUENCE: 31

Gly Val Trp Pro Pro Val Ser Ala Leu Leu Ser Ala Leu Gly Met
1               5                   10                  15

Ser Thr Tyr Lys Arg
            20

<210> SEQ ID NO 32
<211> LENGTH: 15
<212> TYPE: PRT
<213> ORGANISM: Homo Sapiens

<400> SEQUENCE: 32

His Leu Leu Glu Asn Ser Thr Ala Ser Val Ser Glu Ala Glu Arg
1               5                   10                  15

<210> SEQ ID NO 33
<211> LENGTH: 16
<212> TYPE: PRT
<213> ORGANISM: Homo Sapiens

<400> SEQUENCE: 33

His Leu Leu Glu Asn Ser Thr Ala Ser Val Ser Glu Ala Glu Arg Lys
1               5                   10                  15

<210> SEQ ID NO 34
<211> LENGTH: 14
<212> TYPE: PRT
<213> ORGANISM: Homo Sapiens

<400> SEQUENCE: 34

His Thr Leu Gly Glu Asn Ile Ala Asp Asn Gly Gly Leu Lys
1               5                   10

<210> SEQ ID NO 35
<211> LENGTH: 12
<212> TYPE: PRT
<213> ORGANISM: Homo Sapiens

<400> SEQUENCE: 35

Ile Asp Pro Ser Ser Leu Ser Phe Asn Met Trp Lys
1               5                   10

<210> SEQ ID NO 36
<211> LENGTH: 6
<212> TYPE: PRT
<213> ORGANISM: Homo Sapiens

<400> SEQUENCE: 36
```

```
Ile His Leu Val Asp Lys
1               5

<210> SEQ ID NO 37
<211> LENGTH: 15
<212> TYPE: PRT
<213> ORGANISM: Homo Sapiens

<400> SEQUENCE: 37

Ile Ser Leu Cys Leu Ile Cys Ile Ser Cys Leu Leu Tyr Val Lys
1               5                   10                  15

<210> SEQ ID NO 38
<211> LENGTH: 7
<212> TYPE: PRT
<213> ORGANISM: Homo Sapiens

<400> SEQUENCE: 38

Lys Ala Gln Val Tyr Tyr Arg
1               5

<210> SEQ ID NO 39
<211> LENGTH: 9
<212> TYPE: PRT
<213> ORGANISM: Homo Sapiens

<400> SEQUENCE: 39

Lys Pro Glu Leu Glu Arg Pro Ile Lys
1               5

<210> SEQ ID NO 40
<211> LENGTH: 9
<212> TYPE: PRT
<213> ORGANISM: Homo Sapiens

<400> SEQUENCE: 40

Lys Thr Ser Ser Phe Leu Asp Gln Arg
1               5

<210> SEQ ID NO 41
<211> LENGTH: 7
<212> TYPE: PRT
<213> ORGANISM: Homo Sapiens

<400> SEQUENCE: 41

Leu Phe Phe Val Gly Ser Arg
1               5

<210> SEQ ID NO 42
<211> LENGTH: 13
<212> TYPE: PRT
<213> ORGANISM: Homo Sapiens

<400> SEQUENCE: 42

Leu Ile Met Thr Leu Ala Phe Thr Thr Leu Gly Glu Arg
1               5                   10

<210> SEQ ID NO 43
<211> LENGTH: 19
<212> TYPE: PRT
<213> ORGANISM: Homo Sapiens

<400> SEQUENCE: 43

Leu Pro Gly Val Pro Gly Pro Ala Gly Ala Gln Ser Met Ala Gly Ala
1               5                   10                  15
```

Gly Pro Lys

<210> SEQ ID NO 44
<211> LENGTH: 21
<212> TYPE: PRT
<213> ORGANISM: Homo Sapiens

<400> SEQUENCE: 44

Leu Pro Gly Val Pro Gly Pro Ala Gly Ala Gln Ser Met Ala Gly Ala
1               5                   10                  15

Gly Pro Lys Arg Arg
            20

<210> SEQ ID NO 45
<211> LENGTH: 8
<212> TYPE: PRT
<213> ORGANISM: Homo Sapiens

<400> SEQUENCE: 45

Leu Gln Leu Ser Leu Tyr Met Lys
1               5

<210> SEQ ID NO 46
<211> LENGTH: 8
<212> TYPE: PRT
<213> ORGANISM: Homo Sapiens

<400> SEQUENCE: 46

Met Ala Gly Ala Gly Pro Lys Arg
1               5

<210> SEQ ID NO 47
<211> LENGTH: 9
<212> TYPE: PRT
<213> ORGANISM: Homo Sapiens

<400> SEQUENCE: 47

Met Ala Gly Ala Gly Pro Lys Arg Arg
1               5

<210> SEQ ID NO 48
<211> LENGTH: 17
<212> TYPE: PRT
<213> ORGANISM: Homo Sapiens

<400> SEQUENCE: 48

Asn Glu Ile Val Phe Pro Ala Gly Ile Leu Gln Ala Pro Phe Tyr Thr
1               5                   10                  15

Arg

<210> SEQ ID NO 49
<211> LENGTH: 17
<212> TYPE: PRT
<213> ORGANISM: Homo Sapiens

<400> SEQUENCE: 49

Asn Leu Met Asn Ser Leu Gly Thr Gln Asp Gln Met Ser Val Ser Leu
1               5                   10                  15

Ala

<210> SEQ ID NO 50
<211> LENGTH: 19
<212> TYPE: PRT
<213> ORGANISM: Homo Sapiens -continued

<400> SEQUENCE: 50

Asn Ser Asn Ser Asn Val Ile Gln Val Asp Gln Ser Gly Leu Gly Leu
1               5                   10                  15

Pro Ser Arg

<210> SEQ ID NO 51
<211> LENGTH: 8
<212> TYPE: PRT
<213> ORGANISM: Homo Sapiens

<400> SEQUENCE: 51

Asn Ser Ser Val Glu Ala Phe Lys
1               5

<210> SEQ ID NO 52
<211> LENGTH: 9
<212> TYPE: PRT
<213> ORGANISM: Homo Sapiens

<400> SEQUENCE: 52

Asn Ser Ser Val Glu Ala Phe Lys Arg
1               5

<210> SEQ ID NO 53
<211> LENGTH: 9
<212> TYPE: PRT
<213> ORGANISM: Homo Sapiens

<400> SEQUENCE: 53

Pro Phe Pro Gly Asp Gly Gly Thr Arg
1               5

<210> SEQ ID NO 54
<211> LENGTH: 22
<212> TYPE: PRT
<213> ORGANISM: Homo Sapiens

<400> SEQUENCE: 54

Gln Thr Glu Cys Met Val Glu Gln Tyr Ser Asn Tyr Ser Val Asn Gly
1               5                   10                  15

Glu Pro Val Asn Gly Arg
            20

<210> SEQ ID NO 55
<211> LENGTH: 8
<212> TYPE: PRT
<213> ORGANISM: Homo Sapiens

<400> SEQUENCE: 55

Gln Thr Pro Glu Gly Ala Glu Arg
1               5

<210> SEQ ID NO 56
<211> LENGTH: 9
<212> TYPE: PRT
<213> ORGANISM: Homo Sapiens

<400> SEQUENCE: 56

Arg Asp Glu Glu Leu Ile Tyr His Lys
1               5

<210> SEQ ID NO 57
<211> LENGTH: 18

```
<212> TYPE: PRT
<213> ORGANISM: Homo Sapiens

<400> SEQUENCE: 57

Arg Asn Leu Met Asn Ser Leu Gly Thr Gln Asp Gln Met Ser Val Ser
1               5                   10                  15

Leu Ala

<210> SEQ ID NO 58
<211> LENGTH: 23
<212> TYPE: PRT
<213> ORGANISM: Homo Sapiens

<400> SEQUENCE: 58

Arg Gln Thr Glu Cys Met Val Glu Gln Tyr Ser Asn Tyr Ser Val Asn
1               5                   10                  15

Gly Glu Pro Val Asn Gly Arg
            20

<210> SEQ ID NO 59
<211> LENGTH: 12
<212> TYPE: PRT
<213> ORGANISM: Homo Sapiens

<400> SEQUENCE: 59

Arg Arg Ala Leu Ala Ala Pro Ala Ala Glu Glu Lys
1               5                   10

<210> SEQ ID NO 60
<211> LENGTH: 10
<212> TYPE: PRT
<213> ORGANISM: Homo Sapiens

<400> SEQUENCE: 60

Arg Arg Asp Glu Glu Leu Ile Tyr His Lys
1               5                   10

<210> SEQ ID NO 61
<211> LENGTH: 18
<212> TYPE: PRT
<213> ORGANISM: Homo Sapiens

<400> SEQUENCE: 61

Ser Ala Asp Gly Ser Ala Pro Ala Gly Glu Gly Glu Gly Val Thr Leu
1               5                   10                  15

Gln Arg

<210> SEQ ID NO 62
<211> LENGTH: 20
<212> TYPE: PRT
<213> ORGANISM: Homo Sapiens

<400> SEQUENCE: 62

Ser Gly Gly Asp Tyr Ala Tyr Met Leu Glu Val Tyr Gly Ser Leu Pro
1               5                   10                  15

Ala Phe Leu Lys
            20

<210> SEQ ID NO 63
<211> LENGTH: 7
<212> TYPE: PRT
<213> ORGANISM: Homo Sapiens

<400> SEQUENCE: 63
```

```
Ser Gly Thr Ala Gln Val Arg
1               5
```

<210> SEQ ID NO 64
<211> LENGTH: 17
<212> TYPE: PRT
<213> ORGANISM: Homo Sapiens

<400> SEQUENCE: 64

```
Ser Asn Ile Thr Phe Asn Asn Asn Asp Thr Val Ser Phe Leu Glu Tyr
1               5                   10                  15

Arg
```

<210> SEQ ID NO 65
<211> LENGTH: 11
<212> TYPE: PRT
<213> ORGANISM: Homo Sapiens

<400> SEQUENCE: 65

```
Ser Gln Pro Pro Asn Gln His Pro Thr Leu Lys
1               5                   10
```

<210> SEQ ID NO 66
<211> LENGTH: 8
<212> TYPE: PRT
<213> ORGANISM: Homo Sapiens

<400> SEQUENCE: 66

```
Thr Phe Gln Phe Gln Pro Ser Lys
1               5
```

<210> SEQ ID NO 67
<211> LENGTH: 18
<212> TYPE: PRT
<213> ORGANISM: Homo Sapiens

<400> SEQUENCE: 67

```
Thr Pro Glu Ser Ser His Glu Gly Leu Ile Thr Asp Pro His Ser Pro
1               5                   10                  15

Ser Arg
```

<210> SEQ ID NO 68
<211> LENGTH: 6
<212> TYPE: PRT
<213> ORGANISM: Homo Sapiens

<400> SEQUENCE: 68

```
Thr Gln Val Glu Lys Arg
1               5
```

<210> SEQ ID NO 69
<211> LENGTH: 14
<212> TYPE: PRT
<213> ORGANISM: Homo Sapiens

<400> SEQUENCE: 69

```
Thr Ser Pro Phe Phe Ser Val Tyr Val Ser Ala Asp Ser Lys
1               5                   10
```

<210> SEQ ID NO 70
<211> LENGTH: 8
<212> TYPE: PRT
<213> ORGANISM: Homo Sapiens

```
<400> SEQUENCE: 70

Thr Ser Ser Phe Leu Asp Gln Arg
1               5

<210> SEQ ID NO 71
<211> LENGTH: 10
<212> TYPE: PRT
<213> ORGANISM: Homo Sapiens

<400> SEQUENCE: 71

Thr Val Gly Glu Ile Met Trp Gly Tyr Lys
1               5                   10

<210> SEQ ID NO 72
<211> LENGTH: 13
<212> TYPE: PRT
<213> ORGANISM: Homo Sapiens

<400> SEQUENCE: 72

Val Ile Tyr Ala Met Ala Glu Asp Gly Leu Leu Phe Lys
1               5                   10

<210> SEQ ID NO 73
<211> LENGTH: 11
<212> TYPE: PRT
<213> ORGANISM: Homo Sapiens

<400> SEQUENCE: 73

Val Leu Leu Asn Ile Gly Gln Gln Met Leu Arg
1               5                   10

<210> SEQ ID NO 74
<211> LENGTH: 14
<212> TYPE: PRT
<213> ORGANISM: Homo Sapiens

<400> SEQUENCE: 74

Val Leu Thr Gly Tyr Leu Asn Tyr Met Val Gln Leu Gly Lys
1               5                   10

<210> SEQ ID NO 75
<211> LENGTH: 9
<212> TYPE: PRT
<213> ORGANISM: Homo Sapiens

<400> SEQUENCE: 75

Val Gln Asp Ala Phe Ala Ala Ala Lys
1               5

<210> SEQ ID NO 76
<211> LENGTH: 16
<212> TYPE: PRT
<213> ORGANISM: Homo Sapiens

<400> SEQUENCE: 76

Trp Gly Thr Phe Ser Asn Leu Trp Glu His Asn Gln Ala Ile Ile Lys
1               5                   10                  15

<210> SEQ ID NO 77
<211> LENGTH: 6
<212> TYPE: PRT
<213> ORGANISM: Homo Sapiens

<400> SEQUENCE: 77

Trp Asn Gly Leu Ser Lys
1               5
```

<210> SEQ ID NO 78
<211> LENGTH: 9
<212> TYPE: PRT
<213> ORGANISM: Homo Sapiens

<400> SEQUENCE: 78

Tyr Phe Pro Gly Met Phe Pro Phe Lys
1               5

<210> SEQ ID NO 79
<211> LENGTH: 1983
<212> TYPE: DNA
<213> ORGANISM: Homo Sapiens
<220> FEATURE:
<221> NAME/KEY: misc_feature
<222> LOCATION: (1)..(1983)
<223> OTHER INFORMATION: Nucleotide encoding Swissprot Accession no:
      Q01650 - Large neutral amino acid transporter small subunit 1:
      designated in application as OGTA014

<400> SEQUENCE: 79

```
cggcgggcgg cgcgcacact gctcgctggg ccgcggctcc cgggtgtccc aggcccggcc      60
ggtgcgcaga gcatggcggg tgcgggcccg aagcggcgcg cgctagcggc gccggcggcc     120
gaggagaagg aagaggcgcg ggagaagatg ctggccgcca agagcgcgga cggctcggcg     180
ccggcaggcg agggcgaggg cgtgaccctg cagcggaaca tcacgctgct caacggcgtg     240
gccatcatcg tgggaccat tatcggctcg ggcatcttcg tgacgccac gggcgtgctc       300 aaggaggcag gctcgccggg gctggcgctg gtggtgtggg ccgcgtgcgg cgtcttctcc     360
atcgtgggcg cgctctgcta cgcggagctc ggcaccacca tctccaaatc gggcggcgac     420
tacgcctaca tgctggaggt ctacggctcg ctgcccgcct tcctcaagct ctggatcgag     480
ctgctcatca tccggccttc atcgcagtac atcgtggccc tggtcttcgc cacctacctg     540
ctcaagccgc tcttccccac ctgcccggtg cccgaggagg cagccaagct cgtggcctgc     600
ctctgcgtgc tgctgctcac ggccgtgaac tgctacagcg tgaaggccgc cacccgggtc     660
caggatgcct ttgccgccgc caagctcctg gccctggccc tgatcatcct gctgggcttc     720
gtccagatcg ggaagggtga tgtgtccaat ctagatccca acttctcatt tgaaggcacc     780
aaactggatg tggggaacat tgtgctggca ttatacagcg gcctctttgc ctatggagga     840
tggaattact tgaatttcgt cacagaggaa atgatcaacc cctacagaaa cctgccctg     900 gccatcatca tctccctgcc catcgtgacg ctggtgtacg tgctgaccaa cctggcctac     960
ttcaccaccc tgtccaccga gcagatgctg tcgtccgagg ccgtggccgt ggacttcggg    1020
aactatcacc tgggcgtcat gtcctggatc atccccgtct tcgtgggcct gtcctgcttc    1080
ggctccgtca atgggtccct gttcacatcc tccaggctct tcttcgtggg gtcccgggaa    1140
ggccacctgc cctccatcct ctccatgatc caccccacagc tcctcacccc cgtgccgtcc    1200
ctcgtgttca cgtgtgtgat gacgctgctc tacgccttct ccaaggacat cttctccgtc    1260
atcaacttct tcagcttctt caactggctc tgcgtggccc tggccatcat cggcatgatc    1320
tggctgcgcc acagaaagcc tgagcttgag cggcccatca ggtgaacct ggccctgcct    1380 gtgttcttca tcctggcctg cctcttcctg atcgccgtct ccttctggaa gacacccgtg    1440
gagtgtggca tcggcttcac catcatcctg agcggctgc ccgtctactt cttcggggtc    1500
tggtggaaaa acaagcccaa gtggctcctc agggcatct ggataagaca cacagcgcag    1560
caccagctaa tctctcagga cgagggattc cggaaaacca ggctactgct gccaagtaac    1620
```

-continued

```
aaaatcctgc tggctgccac cagcggacac agcagactta cccagaaagg cagaaagagg     1680
cagaggcagg cggatcactt gagccagagg tggagccaag tggtccagcg tcactccagt     1740
gctcagctgt ggctggagga gctggcctgt ggcacagccc tgagtgtccc aagccgggag     1800
ccaacgaagc cggacacggc ttcactgacc agcggctgct caagccgcaa gctctcagca     1860
agtgcccagt ggagcctgcc gccccgcct gggcaccggg accccctcac catccagtgg      1920
gcccggagaa acctgatgaa cagtttgggg actcaggacc agatgtccgt ctctcttgct     1980
tga                                                                   1983
```

<210> SEQ ID NO 80
<211> LENGTH: 2383
<212> TYPE: DNA
<213> ORGANISM: Homo Sapiens
<220> FEATURE:
<221> NAME/KEY: misc_feature
<222> LOCATION: (1)..(2383)
<223> OTHER INFORMATION: Nucleotide encoding Swissprot Accession no:
P42892 - Endothelin converting enzyme 1: designated in
application as OGTA020

<400> SEQUENCE: 80

```
atgcggggcg tgtggccgcc cccggtgtcc gccctgctgt cggcgctggg gatgtcgacg       60
tacaagcggg ccacgctgga cgaggaggac ctggtggact cgctctccga gggcgacgca      120
taccccaacg gcctgcaggt gaacttccac agccccggga gtggccagag gtgctgggct      180
gcacggaccc aggtggagaa gcggctggtg gtgttggtgg tacttctggc ggcaggactg      240
gtggcctgct tggcagcact gggcatccag taccagacaa gatccccctc tgtgtgcctg      300
agcgaagctt gtgtctcagt gaccagctcc atcttgagct ccatggaccc cacagtggac      360
ccctgccatg acttcttcag ctacgcctgt gggggctgga tcaaggccaa cccagtccct      420
gatggccact cacgctgggg gaccttcagc aacctctggg aacacaacca agcaatcatc      480
aagcacctcc tcgaaaactc cacggccagc gtgagcgagg cagagagaaa ggcgcaagta      540
tactaccgtg cgtgcatgaa cgagaccagg atcgaggagc tcagggccaa acctctaatg      600
gagttgattg agaggctcgg gggctggaac atcacaggtc cctgggccaa ggacaacttc      660
caggacaccc tgcaggtggt caccgcccac taccgcacct cacccttctt ctctgtctat      720
gtcagtgccg attccaagaa ctccaacagc aacgtgatcc aggtggacca gtctggcctg      780
ggcttgccct cgagagacta ttacctgaac aaaactgaaa acgagaaggt gctgaccgga      840
tatctgaact acatggtcca gctggggaag ctgctgggcg gcggggacga ggaggccatc      900
cggccccaga tgcagcagat cttggacttt gagacggcac tggccaacat caccatccca      960
caggagaagc gccgtgatga ggagctcatc taccacaaag tgacggcagc cgagctgcag      1020
accttggcac ccgccatcaa ctggttgcct tttctcaaca ccatcttcta ccccgtggag      1080
atcaatgaat ccgagcctat tgtggtctat gacaaggaat accttgagca gatctccact      1140
ctcatcaaca ccaccgacag atgcctgctc aacaactaca tgatctggaa cctggtgcgg      1200
aaaacaagct ccttccttga ccagcgcttt caggacgccg atgagaagtt catggaagtc      1260
atgtacggga ccaagaaggg gaccaccaat agtattactt cttccccgga aacacagacc      1320
ccagaaggtg cagagagaat tggtggccct cagacatcag gggtggggtg agcatgacc      1380 ccgcccatgg tgaacgccta ctactcgccc accaagaatg agattgtgtt tccggccggg      1440
atcctgcagg caccattcta cacacgctcc tcacccaagg ccttaaactt tggtggcata      1500
ggtgtcgtcg tgggccatga gctgactcat gcttttgatg atcaaggacg ggagtatgac      1560
```

-continued

```
aaggacggga acctccggcc atggtggaag aactcatccg tggaggcctt caagcgtcag    1620
accgagtgca tggtagagca gtacagcaac tacagcgtga acggggagcc ggtgaacggg    1680
cggcacaccc tggggagaa catcgccgac aacgggggtc tcaaggcggc ctatcgggct     1740
taccagaact gggtgaagaa gaacgggggct gagcactcgc tccccaccct gggcctcacc   1800
aataaccagc tcttcttcct gggctttgca caggtctggt gctccgtccg cacacctgag    1860
agctcccacg aaggcctcat caccgatccc cacagccccc ctcgcttccg ggtcatcggc    1920
tccctctcca attccaagga gttctcagaa cacttccgct gcccacctgg ctcacccatg    1980
aacccgcctc acaagtgcga agtctggtaa ggacgaagcg gagagagcca agacggagga    2040
ggggaagggg ctgaggacga gacccccatc cagcctccag ggcattgctc agcccgcttg    2100
gccacccggg gccctgcttc ctcacactgg cgggttttca gccggaaccg agcccatggt    2160
gttggctctc aacgtgaccc gcagtctgat ccctgtgaa gagccggaca tcccaggcac     2220
acgtgtgcgc caccttcagc aggcattcgg gtgctgggct ggtggctcat caggcctggg    2280
ccccacactg acaagcgcca gatacgccac aaataccact gtgtcaaatg ctttcaagat    2340
atatttttgg ggaaactatt ttttaaacac tgtggaatac act                      2383
```

<210> SEQ ID NO 81
<211> LENGTH: 3227
<212> TYPE: DNA
<213> ORGANISM: Homo Sapiens
<220> FEATURE:
<221> NAME/KEY: misc_feature
<222> LOCATION: (1)..(3227)
<223> OTHER INFORMATION: Nucleotide encoding Swissprot Accession no:
      Q9NR17 - Procadherin beta 16: designated in application as OGTA067

<400> SEQUENCE: 81

```
ggtgcagatc tctgaggaca gtccaataag cttcctggtt gtgaaggtct ctgccacgga     60
tgtagacaca ggagtcaacg gagagatttc ctattcactt ttccaagctt cagatgagat    120
aagcaaaact tttaaggtcg atttcttgac aggagaaatt cgactaaaga aacaacttga    180
tttcgaaaaa tttcagtcct atgaagtcaa tatcgaggcg agagatgctg gaggcttttc    240
tggaaaatgc accgttctga ttcaagtgat agatgtgaac gaccatgccc cagaagttac    300
catgtctgca tttaccagcc caatacctga gaatgcgcct gaaactgtgg ttgcacttttt   360 cagtgttttca gaccttgatt caggagaaaa tgggaaaata agttgctcca ttcaggagga   420 tctaccctc ctcctgaaat cttctgtggg gaactttttac accctactaa cagagacacc    480
actagacaga gaaagcagag ccgagtacaa cgtcactatc accgtcactg acttagggac    540
acccaggctg acaacacatc tcaatatgac cgtgctggtg tcggacgtca atgacaacgc    600
ccccgccttc acccaaacct cctacaccct gttcgtccgc gagaacaaca gccccgccct    660
gcacatcggc agcgtcagcg ccacagacag agactcgggc accaacgccc aggtcaccta    720
ctcgctgctg ccgccccagg atccgcacct gcccctcgcc tccctggtct ccatcaacac    780
agacaacggc cacctgttcg ccctcaggtc gctggactac gagggccctgc aggcgttcga   840 gttccgggtg ggcgcttcag accgcggctc cccggctttg agcagcgagg cgctggtgcg   900
cgtgctggtg ctggacgcca acgacaactc gcccttcgtg ctgtacccgc tgcagaatgg   960
ctccgcgccc tgcaccgagc tggtgcccccg gcggccgag ccgggctacc tggtgaccaa   1020
ggtggtggcg gtgacggcg actcgggcca gaacgcctgg ctgtcgtacc agctgctcaa   1080
ggccacggag cccgggctgt tcggtgtgtg ggcgcacaat ggcgaggtgc gcaccgccag   1140
```

```
gctgctgagc gagcgcgacg cggccaagca gaggctggtg gtgctggtca aggacaatgg      1200
cgagcctccg tgctcggcca ccgccacgct gcacttgctc ctggtggacg gcttctccca      1260
gccctacctg ccgcttccgg aggctgcccc agcccagggc caggccgact ctctcaccgt      1320
ctacctggtg gtggcgttgg cctcggtgtc ttcgctcttc ctcttctcgg tgctcctgtt      1380
cgtggcggtg ctgctgtgta ggaggagcag ggcggcctcg gtgggtcgct gctcagtgcc      1440
tgagggcccc tttccagggc atctggtgga cgtgaggggc accggagcc tgtctcagaa       1500 ctatcacttg tctggggcgg gcgccgagtt ggggtcctat tccgtagtgg aagaaacgga      1560
gagaggctct tttgtggcaa atctaggaaa agacctgggg ttggggttga cagagatgtc      1620
cacccgcaag gccaggatca tttcccaggg gaacaaacag catttgcagc tcaaggctca      1680
aactggggat tgctcataa atgagaagct agatcgagag gagctatgcg gtcccactga       1740
gccttgcata ctacatttcc aagtgttaat ggaaaaccct ttagaaatat ttcaggctga      1800
actgagggtg atagatataa atgaccattc tcccatgttc actgaaaagg aaatgattct      1860
aaaaataccg gaaaacagtc ctctaggaac tgagttccct ctgaatcatg ctttggactt      1920
ggacgtagga agcaataatg ttcaaaacta taaaatcagc ccaagctctc atttccgggt      1980
tctaatccat gaattcagag atggcaggaa atacccctgag ctagtgttgg ataaagagct     2040
ggatcgggag gaggagcctc aactaagatt aaccctgaca gcgctggatg gtggctctcc      2100
accgcgatct ggaactgctc aggtccgtat tgaagtggtg gacatcaatg ataacgctcc      2160
tgagtttgag cagcccatct acaaagtgca gattccagag aacagtcctc ttggctccct      2220
ggttgccacc gtctccgcca gggatttaga cggcggagcc aatggaaaaa tatcatacac      2280
actctttcag ccttcggagg atattagtaa aactttggag gtaaatccta tgacaggggg      2340
gactccaagg ctgaaaacgg agcacaacat aacagtgcag atatcagatg tcaatgataa      2400
cgcccccact ttcacccaaa cctcctacac cctgttcgtc cgcgagaaca acagccccgc      2460
cctgcacatc ggcagcgtca gcgccacaga cagagactca ggcaccaacg cccaggtcac      2520
ctactcgctg ctgccgcccc aggacccgca cctgccccct gcctccctgg tctccatcaa      2580
cgcagacaac ggccacctgt tcgccctcag gtcgctggac tacgaggccc tgcgggagtt      2640
cgagttccgc gtgagcgcca cagaccgcgg ctcccccggct ttgagcagcg aggcgctggt     2700
gcgcgtgctg gtgctggacg ccaacgacaa ctcgcccttc gtgctgtacc cgctgcagaa      2760
cggctccgcg ccctgcactg agctggtgcc ccgggcggcc gagccgggct acctggtgac      2820
caaggtggtg gcggtggacg cgactcgggg ccagaatgcc tggctgtcgt accagctgct      2880
caaggccacg gagcccgggc tgttcggtgt gtgggcgcac aatggcgagg tgcgcaccgc      2940
caggctgctg agcgagcgcg acgcagccaa gcagaggctg gtggtgctgg tcaaggacaa      3000
tggcgagcct ccgcgctcgg ccaccgccac gctgcacgtg ctcctggtgg acggcttctc      3060
ccagcccttc ctgccgctcc cagaggcggc ccccggccag acccaggcca actcgctcac      3120
tgtctacctg gtggtggcaa tatccctatg tttaatctgt atttcttgct tattatatgt      3180
aaagttgagc ttctttctag atattaggcc tttgaataaa attctat                    3227
```

<210> SEQ ID NO 82
<211> LENGTH: 1415
<212> TYPE: DNA
<213> ORGANISM: Homo Sapiens
<220> FEATURE:
<221> NAME/KEY: misc_feature
<222> LOCATION: (1)..(1415)
<223> OTHER INFORMATION: Nuecleotide encoding Swissprot Accession no:
      P30825 - High affinity cationic acid transporter 1: designated in application as OGTA116

<400> SEQUENCE: 82

| | | | | | |
|---|---|---|---|---|---|
| cccctttccag | gggatggggg | aaccagacag | cagtccaggc | acctggcaca | gctggagccc | 60 |
| tggggtcctt | gggcagctg | cgctgggacg | tggccagtgt | caggagccgc | tctgaacagc | 120 |
| aacatggggt | gcaaagtcct | gctcaacatt | gggcagcaga | tgctgcggcg | aaggtggtg | 180 |
| gactgtagcc | gggaggagac | gcggctgtct | cgctgcctga | cactttga | tctggtggcc | 240 |
| ctcggggtgg | gcagcacact | gggtgctggt | gtctacgtcc | tggctggagc | tgtggcccgt | 300 |
| gagaatgcag | gccctgccat | tgtcatctcc | ttcctgatcg | ctgcgctggc | ctcagtgctg | 360 |
| gctggcctgt | gctatggcga | gtttggtgct | cgggtcccca | agacgggctc | agcttacctc | 420 |
| tacagctatg | tcaccgttgg | agagctctgg | gccttcatca | ccggctggaa | cttaatcctc | 480 |
| tcctacatca | tcggtacttc | aagcgtagcg | agggcctgga | gcgccacctt | cgacgagctg | 540 |
| ataggcagac | ccatcgggga | gttctcacgg | acacacatga | ctctgaacgc | ccccggcgtg | 600 |
| ctggctgaaa | accccgacat | attcgcagtg | atcataattc | tcatcttgac | aggacttta | 660 |
| actcttggtg | tgaaagagtc | ggccatggtc | aacaaaatat | tcacttgtat | taacgtcctg | 720 |
| gtcctgggct | tcataatggt | gtcaggattt | gtgaaaggat | cggttaaaaa | ctggcagctc | 780 |
| acggaggagg | attttgggaa | cacatcaggc | cgtctctgtt | tgaacaatga | cacaaaagaa | 840 |
| gggaagcccg | tgttggtgg | attcatgccc | ttcgggttct | ctggtgtcct | gtcggggca | 900 |
| gcgacttgct | tctatgcctt | cgtgggcttt | gactgcatcg | ccaccacagg | tgaagaggtg | 960 |
| aagaacccac | agaaggccat | ccccgtgggg | atcgtggcgt | ccctcttgat | ctgcttcatc | 1020 |
| gcctactttg | gggtgtcggc | tgccctcacg | ctcatgatgc | cctacttctg | cctggacaat | 1080 |
| aacagccccc | tgcccgacgc | ctttaagcac | gtgggctggg | aaggtccaa | gtacgcagtg | 1140 |
| gccgtgggct | ccctctgcgc | tctttccgcc | agtcttctag | gttccatgtt | tcccatgcct | 1200 |
| cgggttatct | atgccatggc | tgaggatgga | ctgctattta | aattcttagc | caacgtcaat | 1260 |
| gataggacca | aaacaccaat | aatcgccaca | ttagcctcgg | gtgccgttgc | tgctgtgatg | 1320 |
| gccttcctct | ttgacctgaa | ggacttggtg | gacctcatgt | ccattggcac | tctcctggct | 1380 |
| tactcgttgg | tggctgcctg | tgtgttggtc | ttacg | | | 1415 |

<210> SEQ ID NO 83
<211> LENGTH: 2644
<212> TYPE: DNA
<213> ORGANISM: Homo Sapiens
<220> FEATURE:
<221> NAME/KEY: misc_feature
<222> LOCATION: (1)..(2644)
<223> OTHER INFORMATION: Nucleotide encoding Swissprot Accession no:
    Q8WTV0 - Scavenger receptor class B member 1: designated in
    application as OGTA194

<400> SEQUENCE: 83

| | | | | | |
|---|---|---|---|---|---|
| gtcgccgtcc | ccgtctcctg | ccaggcgcgg | agccctgcga | gccgcgggtg | ggccccaggc | 60 |
| gcgcagacat | gggctgctcc | gccaaagcgc | gctgggctgc | cggggcgctg | gcgtcgcgg | 120 |
| ggctactgtg | cgctgtgctg | ggcgctgtca | tgatcgtgat | ggtgccgtcg | ctcatcaagc | 180 |
| agcaggtcct | taagaacgtg | cgcatcgacc | ccagtagcct | gtccttcaac | atgtggaagg | 240 |
| agatccctat | ccccttctat | ctctccgtct | acttctttga | cgtcatgaac | cccagcgaga | 300 |
| tcctgaaggg | cgagaagccg | caggtgcggg | agcgcgggcc | ctacgtgtac | agggagttca | 360 |
| ggcacaaaag | caacatcacc | ttcaacaaca | acgacaccgt | gtccttcctc | gagtaccgca | 420 |

-continued

```
ccttccagtt ccagccctcc aagtcccacg gctcggagag cgactacatc gtcatgccca    480
acatcctggt cttgggtgcg gcggtgatga tggagaataa gcccatgacc ctgaagctca    540
tcatgacctt ggcattcacc accctcggcg aacgtgcctt catgaaccgc actgtgggtg    600
agatcatgtg gggctacaag gaccccttg  tgaatctcat caacaagtac tttccaggca    660 tgttccccctt caaggacaag ttcggattat tgctgagct  caacaactcc gactctgggc    720
tcttcacggt gttcacgggg gtccagaaca tcagcaggat ccacctcgtg acaagtgga     780 acgggctgag caaggttgac ttctggcatt ccgatcagtg caacatgatc aatggaactt    840
ctgggcaaat gtgccgccc  ttcatgactc ctgagtcctc gctggagttc tacagcccgg    900
aggcctgccg atccatgaag ctaatgtaca aggagtcagg ggtgtttgaa ggcatcccca    960
cctatcgctt cgtggctccc aaaaccctgt tgccaacgg  gtccatctac ccacccaacg    1020
aaggcttctg cccgtgcctg gagtctggaa ttcagaacgt cagcacctgc aggttcagtg    1080
cccccttgtt tctctcccat cctcacttcc tcaacgctga cccggttctg gcagaagcgg    1140
tgactggcct gcaccctaac caggaggcac actccttgtt cctggacatc cacccggtca    1200
cgggaatccc catgaactgc tctgtgaaac tgcagctgag cctctacatg aaatctgtcg    1260
caggcattgg acaaactggg aagattgagc ctgtggtcct gccgctgctc tggtttgcag    1320
agagcggggc catggagggg gagactcttc acacattcta cactcagctg gtgttgatgc    1380
ccaaggtgat gcactatgcc cagtacgtcc tcctggcgct gggctgcgtc ctgctgctgg    1440
tccctgtcat ctgccaaatc cggagccaac ccccaaatca gcatcccacc ctcaaatcca    1500
gtaagaatgc tacgatcggc agtgtggctc cctccctgca ggtttcactg gaggccacga    1560
gaaatgctat ttattttgga gtagtagtaa aaagggctca aaggataagg aggccattca    1620
ggcctattct gaatccctga tgacatcagc tcccaagggc tctgtgctgc aggaagcaaa    1680
actgtagggt cctgaggaca ccgtgagcca gccaggcctg gccgctgggc ctgaccggcc    1740
ccccagcccc tacaccccgc ttctcccgga ctctcccagc ggacagcccc ccagcccac     1800 agcctgagcc tcccagctgc catgtgcctg ttgcacacct gcacacacg  cctggcacac    1860 atacacacat gcgtgcaggc ttgtgcagac actcagggat ggagctgctg ctgaagggac    1920
ttgtagggag aggctcgtca acaagcactg ttctggaacc ttctctccac gtggcccaca    1980
ggcctgacca caggggctgt gggtcctgcg tccccttcct cgggtgagcc tggcctgtcc    2040
cgttcagccg ttgggcccag gcttcctccc ctccaaggtg aaacactgca gtcccggtgt    2100
ggtggctccc catgcaggac gggccaggct gggagtgccg ccttcctgtg ccaaattcag    2160
tggggactca gtgcccaggc cctggccacg agctttggcc ttggtctacc tgccaggca    2220 ggcaaagcgc ctttacacag gcctcggaaa acaatggagt gagcacaaga tgccctgtgc    2280
agctgcccga gggtctccgc ccaccccggc cggactttga tcccccgaa  gtcttcacag    2340 gcactgcatc gggttgtctg cgcccctttt cctccagcct aaactgacat catcctatgg    2400
actgagccgg ccactctctg gccgaagtgg ccgcaggctg tgccccgag  ctgcccccac    2460 cccctcacag ggtccctcag attataggtg cccaggctga ggtgaagagg cctggggcc     2520 ctgccttccg ggcgctcctg gaccctgggg caaacctgtg accctttct  actggaatag    2580 aaatgagttt tatcatcttt gaaaataat  tcactcttga agtaataaac gtttaaaaaa    2640
atgg                                                                  2644
```

<210> SEQ ID NO 84
<211> LENGTH: 23
<212> TYPE: PRT

```
<213> ORGANISM: Homo Sapiens

<400> SEQUENCE: 84

Met Leu Ala Ala Lys Ser Ala Asp Gly Ser Ala Pro Ala Gly Glu Gly
1               5                   10                  15

Glu Gly Val Thr Leu Gln Arg
            20

<210> SEQ ID NO 85
<211> LENGTH: 6
<212> TYPE: PRT
<213> ORGANISM: Homo Sapiens

<400> SEQUENCE: 85

Leu Val Val Leu Val Lys
1               5

<210> SEQ ID NO 86
<211> LENGTH: 5
<212> TYPE: PRT
<213> ORGANISM: Homo Sapiens

<400> SEQUENCE: 86

Gln Gln Val Leu Lys
1               5

<210> SEQ ID NO 87
<211> LENGTH: 9
<212> TYPE: PRT
<213> ORGANISM: Homo Sapiens

<400> SEQUENCE: 87

Arg Asp Glu Glu Leu Ile Tyr His Lys
1               5
```